(12) United States Patent
Lin et al.

(10) Patent No.: US 6,656,958 B2
(45) Date of Patent: Dec. 2, 2003

(54) SUBSTITUTED PYRIDINE COMPOUNDS USEFUL FOR CONTROLLING CHEMICAL SYNAPTIC TRANSMISSION

(75) Inventors: Nan-Horng Lin, Vernon Hills, IL (US); Liming Dong, San Diego, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/775,227

(22) Filed: Feb. 1, 2001

(65) Prior Publication Data

US 2002/0058646 A1 May 16, 2002

Related U.S. Application Data

(60) Provisional application No. 60/179,677, filed on Feb. 2, 2000.

(51) Int. Cl.[7] ...................... A01N 43/40; C07D 213/84; C07D 213/54; C07D 213/70; C07D 213/78
(52) U.S. Cl. ...................... 514/332; 514/334; 514/335; 514/348; 514/349; 514/350; 514/351; 514/357; 546/255; 546/257; 546/261; 546/262; 546/264; 546/290; 546/291; 546/296; 546/298; 546/300; 546/304; 546/314; 546/329; 546/334; 546/337
(58) Field of Search .................. 546/329, 334, 546/337, 255, 257, 261, 262, 264, 290, 291, 296, 298, 300, 304, 314; 514/332, 334, 335, 345, 348, 349, 350, 351, 357

(56) References Cited

U.S. PATENT DOCUMENTS 5,616,707 A   4/1997   Crooks et al. .............. 544/242

FOREIGN PATENT DOCUMENTS

| EP | 0 287 908 | 11/2000 | ................. 546/329 |
| WO | 00 71520  | 4/1988  | ................. 546/329 |
| WO | 96 40682  | 12/1996 | ................. 546/329 |
| WO | 97 46544  | 12/1997 | ................. 546/329 |
| WO | 00 62767  | 10/2000 | ................. 546/329 |

*Primary Examiner*—Alan L. Rotman
*Assistant Examiner*—Raymond Covington
(74) *Attorney, Agent, or Firm*—Portia Chen

(57) ABSTRACT

The present invention is directed to a series of substituted pyridine compounds, a method for selectively controlling neurotransmitter release in mammals using these compounds, and pharmaceutical compositions containing these compounds. Preferred compounds are 3'-(5'- and/or 6'-substituted) pyridyl ethers.

10 Claims, No Drawings

SUBSTITUTED PYRIDINE COMPOUNDS USEFUL FOR CONTROLLING CHEMICAL SYNAPTIC TRANSMISSION

This application claims priority to the provisional application Ser. No. 60/179,677 filed on Feb. 2, 2000.

FIELD OF THE INVENTION

The present invention is directed to a series of substituted pyridine compounds, a method for selectively controlling neurotransmitter release in mammals using these compounds, and pharmaceutical compositions containing these compounds. Preferred compounds are 3'-(5'- and/or 6'-substituted) pyridyl ethers.

BACKGROUND OF THE INVENTION

Compounds that selectively control chemical synaptic transmission offer therapeutic utility in treating disorders that are associated with dysfunctions in synaptic transmission. This utility may arise from controlling either presynaptic or post-synaptic chemical transmission. The control of synaptic chemical transmission is, in turn, a direct result of a modulation of the excitability of the synaptic membrane. Presynaptic control of membrane excitability results from the direct effect an active compound has upon the organelles and enzymes present in the nerve terminal for synthesizing, storing, and releasing the neurotransmitter, as well as the process for active re-uptake. Postsynaptic control of membrane excitability results from the influence an active compound has upon the cytoplasmic organelles that respond to neurotransmitter action.

An explanation of the processes involved in chemical synaptic transmission will help to illustrate more fully the potential applications of the invention. (For a fuller explanation of chemical synaptic transmission refer to Hoffman et al., "Neuro-transmission: The autonomic and somatic motor nervous systems." In: *Goodman and Gilman's, The Pharmacological Basis of Therapeutics,* 9th ed., J. G. Hardman, L. E. Limbird, P. B. Molinoff, R. W. Ruddon, and A. Goodman Gilman, eds., Pergamon Press, New York, 1996, pp. 105–139).

Typically, chemical synaptic transmission begins with a stimulus that depolarizes the transmembrane potential of the synaptic junction above the threshold that elicits an all-or-none action potential in a nerve axon. The action potential propagates to the nerve terminal where ion fluxes activate a mobilization process leading to neurotransmitter secretion and "transmission" to the postsynaptic cell. Those cells which receive communication from the central and peripheral nervous systems in the form of neurotransmitters are referred to as "excitable cells." Excitable cells are cells such as nerves, smooth muscle cells, cardiac cells and glands. The effect of a neurotransmitter upon an excitable cell may be to cause either an excitatory or an inhibitory postsynaptic potential (EPSP or IPSP, respectively) depending upon the nature of the postsynaptic receptor for the particular neurotransmitter and the extent to which other neurotransmitters are present. Whether a particular neurotransmitter causes excitation or inhibition depends principally on the ionic channels that are opened in the postsynaptic membrane (i.e., in the excitable cell).

EPSPs typically result from a local depolarization of the membrane due to a generalized increased permeability to cations (notably $Na^+$ and $K^+$), whereas IPSPs are the result of stabilization or hyperpolarization of the membrane excitability due to a increase in permeability to primarily smaller ions (including $K^+$ and $Cl^-$). For example, the neurotransmitter acetylcholine excites at skeletal muscle junctions by opening permeability channels for $Na^+$ and $K^+$. At other synapses, such as cardiac cells, acetylcholine can be inhibitory, primarily resulting from an increase in $K^+$ conductance.

The biological effects of the compounds of the present invention result from modulation of a particular subtype of acetylcholine receptor. It is, therefore, important to understand the differences between two receptor subtypes. The two distinct subfamilies of acetylcholine receptors are defined as nicotinic acetylcholine receptors and muscarinic acetylcholine receptors. (See *Goodman and Gilman's, The Pharmacological Basis of Therapeutics,* op. cit.).

The responses of these receptor subtypes are mediated by two entirely different classes of second messenger systems. When the nicotinic acetylcholine receptor is activated, the response is an increased flux of specific extracellular ions (e.g. $Na^+$, $K^+$ and $Ca^{++}$) through the neuronal membrane. In contrast, muscarinic acetylcholine receptor activation leads to changes in intracellular systems that contain complex molecules such as G-proteins and inositol phosphates. Thus, the biological consequences of nicotinic acetylcholine receptor activation are distinct from those of muscarinic receptor activation. In an analogous manner, inhibition of nicotinic acetylcholine receptors results in still other biological effects, which are distinct and different from those arising from muscarinic receptor inhibition.

As indicated above, the two principal sites to which drug compounds that affect chemical synaptic transmission may be directed are the presynaptic membrane and the postsynaptic membrane. Actions of drugs directed to the presynaptic site may be mediated through presynaptic receptors that respond to the neurotransmitter which the same secreting structure has released (i.e., through an autoreceptor), or through a presynaptic receptor that responds to another neurotransmitter (i.e., through a heteroreceptor). Actions of drugs directed to the postsynaptic membrane mimic the action of the endogenous neurotransmitter or inhibit the interaction of the endogenous neurotransmitter with a postsynaptic receptor.

Classic examples of drugs that modulate postsynaptic membrane excitability are the neuromuscular blocking agents which interact with nicotinic acetylcholine-gated channel receptors on skeletal muscle, for example, competitive (stabilizing) agents, such as curare, or depolarizing agents, such as succinylcholine.

In the central nervous system, postsynaptic cells can have many neurotransmitters impinging upon them. This makes it difficult to know the precise net balance of chemical synaptic transmission required to control a given cell. Nonetheless, by designing compounds that selectively affect only one pre- or postsynaptic receptor, it is possible to modulate the net balance of all the other inputs. Obviously, the more that is understood about chemical synaptic transmission in CNS disorders, the easier it would be to design drugs to treat such disorders.

Knowing how specific neurotransmitters act in the CNS allows one to predict the disorders that may be treatable with certain CNS-active drugs. For example, dopamine is widely recognized as an important neurotransmitter in the central nervous systems in humans and animals. Many aspects of the pharmacology of dopamine have been reviewed by Roth and Elsworth, "Biochemical Pharmacology of Midbrain Dopamine Neurons", In: *Psychopharmacology: The Fourth Generation of Progress,* F. E. Bloom and D. J. Kupfer, Eds., Raven Press, NY, 1995, pp 227–243). Patients with Parkinson's disease have a primary loss of dopamine containing neurons of the nigrostriatal pathway, which results in profound loss of motor control. Therapeutic strategies to replace the dopamine deficiency with dopamine mimetics, as well as administering pharmacologic agents that modify dopamine release and other neurotransmitters have been found to have therapeutic benefit ("Parkinson's Disease", In: *Psychopharmacology: The Fourth Generation of Progress*, op. cit., pp 1479–1484).

New and selective neurotransmitter controlling agents are still being sought, in the hope that one or more will be useful in important, but as yet poorly controlled, disease states or behavior models. For example, dementia, such as is seen with Alzheimer's disease or Parkinsonism, remains largely untreatable. Symptoms of chronic alcoholism and nicotine withdrawal involve aspects of the central nervous system, as does the behavioral disorder Attention-Deficit Disorder (ADD). Specific agents for the treatment of these and related disorders are few in number or non-existent.

A more complete discussion of the possible utility as CNS-active agents of compounds with activity as cholinergic ligands selective for neuronal nicotinic receptors, (i.e., for controlling chemical synaptic transmission) may be found in U.S. Pat. No. 5,472,958, to Gunn et al., issued Dec. 5, 1995, which is incorporated herein by reference.

Existing acetylcholine agonists are therapeutically suboptimal in treating the conditions discussed above. For example, such compounds have unfavorable pharmacokinetics (e.g., arecoline and nicotine), poor potency and lack of selectivity (e.g., nicotine), poor CNS penetration (e.g., carbachol) or poor oral bioavailability (e.g., nicotine). In addition, other agents have many unwanted central agonist actions, including hypothermia, hypolocomotion and tremor and peripheral side effects, including miosis, lachrymation, defecation and tachycardia (Benowitz et al., in: *Nicotine Psychopharmacology*, S. Wonnacott, M. A. H. Russell, & I. P. Stolerman, eds., Oxford University Press, Oxford, 1990, pp. 112–157; and M. Davidson, et al., in *Current Research in Alzheimer Therapy*, E. Giacobini and R. Becker, ed.; Taylor & Francis: New York, 1988; pp 333–336).

Williams et al. reports the use of cholinergic channel modulators to treat Parkinson's and Alzheimer's Diseases. M. Williams et al., "Beyond the Tobacco Debate: Dissecting Out the Therapeutic Potential of Nicotine", *Exp. Opin. Invest. Drugs* 5, pp. 1035–1045 (1996). Salin-Pascual et al. reports short-term improvement of non-smoking patients suffering from depression by treatment with nicotine patches. R. J. Salin-Pascual et al., "Antidepressant Effect of Transdernal Nicotine Patches in Non-Smoking Patients with Major Depression", *J. Clin. Psychiatry*, v. 57, pp. 387–389 (1996).

Ethers which are useful as antagonists of specific 5-hydroxy tryptamine (5-HT) receptors are disclosed in GB 2 208 510A; U.S. Pat. No. 4,929,625; U.S. Pat. No. 5,082,843 and U.S. Pat. No. 4,997,839. However, these references disclose a 2-pyridyl moiety linked by oxygen to a saturated azabicyclic ring such as quinuclidyl or tropanyl.

Analgesic pyridine-2-ethers are also disclosed in U.S. Pat. Nos. 4,946,836 and 4,643,995.

In these references, a 2-pyridyl moiety is linked to a nitrogen-containing cycloaliphatic ring through an —O—$(CH_2)_n$— linkage.

3-Pyridyloxymethyl heterocyclic ether compounds useful in controlling chemical synaptic transmission are disclosed in U.S. Pat. No. 5,629,325; wherein a 3-pyridyl moiety is linked to a nitrogen-containing cycloaliphatic ring through an —O—$CH_2$— linkage. PCT Patent Application WO 94/08992 discloses various 3-pyridyloxy-heterocyclic compounds that are either unsubstituted or mono-substituted on the pyndine rings with groups such as Br, Cl, F, hydroxyl, $C_1$–$C_3$ alkyl or $C_1$–$C_3$ alkoxy, such compounds also described as having utility in enhancing cognitive function.

1,3-disubstituted pyrrolidines which have pharmacological action on the central nervous system wherein the pyrrolidine nitrogen is substituted by an —$(CH_2)_n$—B group, and ether-linked to a substituted pyridyl, among others are disclosed in U.S. Pat. No. 5,037,841.

Cyclic amine compounds effective against senile dementia wherein the ring is ether-linked to a substituted 3-pyridyl among others are disclosed in European Patent Application No. 0 673 927 A1.

Aza ring ether derivatives and their use as nicotinic ACH receptor modulators are disclosed in WO 99/24422.

U.S. Pat. No. 4,206,117 discloses 3-pyridyl aminoalkyl ether derivatives.

U.S. Pat. No. 5,852,041 discloses a class of pyridine compounds which are modulators of acetylcholine receptors.

However, there is still a need for improved compounds for controlling chemical synaptic transmission.

It is therefore an object of this invention to provide novel substituted pyridine compounds. It is a further object of this invention to provide such compounds which selectively control neurotransmitter release.

SUMMARY OF THE INVENTION

The present invention is directed to a series of substituted pyridine compounds, a method for selectively controlling neurotransmitter release in mammals using these compounds, and pharmaceutical compositions including these compounds. More particularly, the present invention is directed to compounds of the formula I Formula I

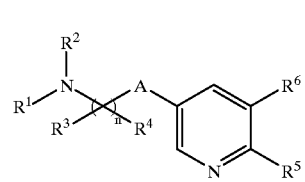

wherein n is an integer of 1 to 4;

$R^1$ and $R^2$ are independently selected from the group consisting of hydrogen, lower alkyl, alkenyl, alkynyl, aralkyl and cyanomethyl;

$R^3$, at each occurrence, is selected from the group consisting of hydrogen, haloalkyl and lower alkyl;

$R^4$, at each occurrence, is independently selected from the group consisting of hydrogen, hydroxyl, lower alkyl, lower alkenyl, lower alkynyl, lower alkoxy, alkenoxy, alkynoxy, thioalkoxy, aliphatic acyl, —$CF_3$, nitro, cyano, —$N(C_1$–$C_3$ alkyl)-C(O)($C_1$–$C_3$ alkyl), —$C_1$–$C_3$ alkylamino, alkenylamino, alkynylamino, di($C_1$–$C_3$ alkyl)amino, amino, halogen, —C(O)O—($C_1$–$C_3$ alkyl), —C(O)NH—($C_1$–$C_3$ alkyl), aliphatic acyl, —CH=NOH, —$PO_3H_2$, —$OPO_3H_2$, heterocyclylalkyl, —C(O)N($C_1$–$C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, aralkenyl, alkylheterocyclyl, sulfonyl, sulfonamido, carbamate, aryloxyalkyl, carboxyl and —C(O)NH(benzyl);

$R^5$ is selected from the group consisting of hydrogen, halogen, lower alkyl, nitro, lower alkylamino and lower alkoxy;

$R^6$ is selected from the group consisting of hydrogen, halogen, hydroxyl, lower alkyl, lower alkenyl, lower alkynyl, lower alkoxy, alkenoxy, alkynoxy, thioalkoxy, aliphatic acyl, —$CF_3$, nitro, amino, cyano, —N($C_1$-$C_3$ alkyl)-C(O)($C_1$-$C_3$ alkyl), —$C_1$-$C_3$ alkylamino, alkenylamino, alkynylamino, di($C_1$-$C_3$ alkyl)amino, —CH=NOH, —C(O)O—($C_1$-$C_3$ alkyl), —C(O)NH—($C_1$-$C_3$ alkyl), —C(O)N($C_1$-$C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, aralkenyl, alkylheterocyclyl, sulfonyl, sulfonamido, carbamate, aliphatic acyl, —CH=NOH, —$PO_3H_2$, —$OPO_3H_2$, heterocyclylalkyl, aryloxyalkyl, carboxyl and —C(O)NH(benzyl); and A is selected from the group consisting of —O—, —S—, —N($R^1$)—, —$SO_2$N($R^1$)— and —$NR^1SO_2$—;

wherein $R^1$, $R^2$, $R^3$, $R^4$, $R^5$ and $R^6$ are unsubstituted or substituted with at least one electron donating or electron withdrawing group;

and pharmaceutically acceptable salts thereof; with the proviso that when A=O, at least one of $R^5$ or $R^6$ is halogen; and with the further proviso that when $R^3$ and $R^4$ are attached to a carbon which is alpha to a heteroatom, $R^4$ is not halogen, hydroxyl or amino.

Presently preferred compounds are of formula II shown below:

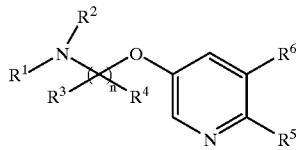

Formula II wherein n is an integer of 1 to 4;

$R^1$ and $R^2$ are independently selected from the group consisting of hydrogen, lower alkyl, alkenyl, alkynyl, aralkyl and cyanomethyl;

$R^3$, at each occurrence, is selected from the group consisting of hydrogen, haloalkyl and lower alkyl;

$R^4$, at each occurrence, is independently selected from the group consisting of hydrogen, hydroxyl, lower alkyl, lower alkenyl, lower alkynyl, lower alkoxy, alkenoxy, alkynoxy, thioalkoxy, aliphatic acyl, —$CF_3$, nitro, cyano, —N($C_1$-$C_3$ alkyl)-C(O)($C_1$-$C_3$ alkyl), —$C_1$-$C_3$ alkylamino, alkenylamino, alkynylamino, di($C_1$-$C_3$ alkyl)amino, amino, halogen, —C(O)O—($C_1$-$C_3$ alkyl), —C(O)NH—($C_1$-$C_3$ alkyl), aliphatic acyl, —CH=NOH, —$PO_3H_2$, —$OPO_3H_2$, heterocyclylalkyl, —C(O)N($C_1$-$C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, aralkenyl, alkylheterocyclyl, sulfonyl, sulfonamido, carbamate, aryloxyalkyl, carboxyl and —C(O)NH(benzyl);

$R^5$ is selected from the group consisting of hydrogen, halogen, lower alkyl, nitro, lower alkylamino and lower alkoxy; and $R^6$ is selected from the group consisting of hydrogen, halogen, hydroxyl, lower alkyl, lower alkenyl, lower alkynyl, lower alkoxy, alkenoxy, alkynoxy, thioalkoxy, aliphatic acyl, —$CF_3$, nitro, amino, cyano, —N($C_1$-$C_3$ alkyl)-C(O)($C_1$-$C_3$ alkyl), —$C_1$-$C_3$ alkylamino, alkenylamino, alkynylamino, di($C_1$-$C_3$ alkyl)amino, —C(O)O—($C_1$-$C_3$ alkyl), —C(O)NH—($C_1$-$C_3$ alkyl), —CH=NOH, —C(O)N($C_1$-$C_3$ alkyl)$_2$, haloalkyl, alkoxylcarbonyl, alkoxyalkoxy, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, aralkenyl, alkylheterocyclyl, sulfonyl, sulfonamido, carbamate, aliphatic acyl, —CH=NOH, —$PO_3H_2$, —$OPO_3H_2$, heterocyclylalkyl, aryloxyalkyl, carboxyl and —C(O)NH(benzyl);

wherein $R^1$, $R^2$, $R^3$, $R^4$, $R^5$ and $R^6$ are unsubstituted or substituted with at least one electron donating or electron withdrawing group;

and pharmaceutically acceptable salts thereof;

with the proviso that when $R^3$ and $R^4$ are attached to a carbon
    which is alpha to a heteroatom, $R^4$ is not halogen, hydroxyl or amino;

and with the further proviso that at least one of $R^5$ or $R^6$ is halogen.

Presently preferred are compounds of formula II wherein n=2, $R^5$ is halogen and $R^6$ is selected from the group consisting of hydrogen, lower alkyl and halogen.

Presently most preferred compounds are of formula III shown below:

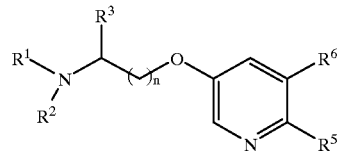

Formula III wherein n is an integer of 1 to 4;

$R^1$ and $R^2$ are independently selected from the group consisting of hydrogen and lower alkyl;

$R^3$ is selected from the group consisting of hydrogen, haloalkyl and lower alkyl;

$R^5$ is selected from the group consisting of hydrogen, halogen, lower alkyl, nitro, lower alkylamino and lower alkoxy; and $R^6$ is selected from the group consisting of hydrogen, halogen, hydroxyl, lower alkyl, lower alkenyl, lower alkynyl, lower alkoxy, alkenoxy, alkynoxy, thioalkoxy, aliphatic acyl, —$CF_3$, nitro, amino, cyano, —N($C_1$—$C_3$ alkyl)-C(O)($C_1$-$C_3$ alkyl), —$C_1$-$C_3$ alkylamino, alkenylamino, alkynylamino, di($C_1$-$C_3$ alkyl)amino, CH=NOH, —C(O)O—($C_1$-$C_3$ alkyl), —C(O)NH—($C_1$-$C_3$ alkyl), —C(O)N($C_1$-$C_3$ alkyl)$_2$, haloalkyl, alkoxylcarbonyl, alkoxyalkoxy, aliphatic acyl, —CH=NOH, —$PO_3H_2$, —$OPO_3H_2$, heterocyclylalkyl, carboxaldehyde, carboxamide, cycloalkyl, cycloalkenyl, cycloalkynyl, aryl, aroyl, aryloxy, arylamino, biaryl, thioaryl, heterocyclyl, heterocycloyl, alkylaryl, aralkyl, aralkenyl, alkylheterocyclyl, sulfonyl, sulfonamido, carbamate, aryloxyalkyl, carboxyl and —C(O)NH(benzyl);

wherein $R^1$, $R^2$, $R^3$, $R^5$ and $R^6$ are unsubstituted or substituted with at least one electron donating or electron withdrawing group;

and pharmaceutically acceptable salts thereof;

with the proviso that at least one of $R^5$ or $R^6$ is halogen.

Presently preferred compounds of formula III have $R^5$ and $R^6$ each independently selected from the group consisting of lower alkyl, —F, —Cl and —Br; n=1 or 2 and $R^3$ as lower alkyl or haloalkyl.

Presently preferred compounds include 5-[(S)-2-amino-1-propyloxy]-2-chloro pyridine, 5-[(S)-2-methylamino-1-propyloxy]-2-chloro pyridine, 5-[(S)-2-amino-1-propyloxy]-2-fluoro pyridine, 5-[(S)-2-methylamino-1-propyloxy]-2-fluoro pyridine, 5-[(S)-2-methylamino-1-propyloxy]-2-chloro-3-bromo pyridine, 5-[(S)-2-methylamino-1-propyloxy]-2-chloro-3-methyl pyridine and pharmaceutically acceptable salts thereof including, but not limited to p-toluene sulfonic acid.

DETAILED DESCRIPTION OF THE INVENTION

Definitions of Terms

The term "alkyl" as used herein alone or in combination refers to $C_1$–$C_{12}$ straight or branched, substituted or unsubstituted saturated chain radicals derived from saturated hydrocarbons by the removal of one hydrogen atom, unless the term alkyl is preceded by a $C_x$–$C_y$ designation. Representative examples of alkyl groups include methyl, ethyl, n-propyl, iso-propyl, n-butyl, sec-butyl, iso-butyl, and tert-butyl among others.

The term "alkenyl", alone or in combination, refers to a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl", alone or in combination, refers to a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" refers to a $C_1$–$C_6$ unit for a particular functionality. For example lower alkyl means $C_1$–$C_6$ alkyl.

The term "aliphatic acyl" alone or in combination, refers to radicals of formula alkyl-C(O)—, alkenyl-C(O)— and alkynyl-C(O)— derived from an alkane-, alkene- or alkyn-carboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl and methylpropiolyl, among others.

The term "cycloalkyl" as used herein refers to an aliphatic ring system having 3 to 10 carbon atoms and 1 to 3 rings including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

"Cycloalkyl" includes cis or trans forms. Furthermore, the substituents may either be in endo or exo positions in the bridged bicyclic systems.

The term "cycloalkenyl" as used herein alone or in combination refers to a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" as used herein refers to a cycloalkyl group appended to a lower alkyl radical, including, but not limited to cyclohexylmethyl.

The term "halo" or "halogen" as used herein refers to I, Br, Cl or F.

The term "haloalkyl" as used herein refers to a lower alkyl radical, to which is appended at least one halogen substituent, for example chloromethyl, fluoroethyl, trifluoromethyl and pentafluoroethyl among others.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy", alone or in combination, refers to a radical of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy", alone or in combination, refers to a radical of formula alkynyl-O—, provided that the radical is not an -ynol ether. Examples of suitable alkynoxy radicals include, but are not limited to, propargyloxy, 2-butynyloxy and the like.

The term "carboxyl" as used herein refers to a carboxylic acid radical, —C(O)OH.

The term "thioalkoxy", refers to a thioether radical of formula alkyl-S—, wherein "alkyl" is as defined above.

The term "carboxaldehyde" as used herein refers to —C(O)R wherein R is hydrogen.

The term "carboxamide" as used herein refers to —C(O)NR$_a$R$_b$, wherein R$_a$ and R$_b$ are each independently hydrogen, alkyl or any other suitable substituent.

The term "alkoxyalkoxy" as used herein refers to R$_c$O—R$_d$O— wherein R$_c$ is lower alkyl as defined above and RF is alkylene wherein alkylene is —(CH$_2$)$_{n'}$— wherein n' is an integer from 1 to 6. Representative examples of alkoxyalkoxy groups include methoxymethoxy, ethoxyinethoxy, t-butoxymethoxy among others.

The term "alkylamino" as used herein refers to R$_e$NH— wherein R$_e$ is a lower alkyl group, for example, ethylamino, butylamino, among others.

The term "alkenylamino" alone or in combination, refers to a radical of formula alkenyl-NH— or (alkenyl)$_2$N—, wherein the term "alkenyl" is as defined above, provided that the radical is not an enamine. An example of such alkenylamino radical is the allylamino radical.

The term "alkynylamino", alone or in combination, refers to a radical of formula alkynyl-NH— or (alkynyl)$_2$N— wherein the term "alkynyl" is as defined above, provided that the radical is not an amine. An example of such alkynylamino radicals is the propargyl amino radical.

The term "dialkylamino" as used herein refers to R$_f$R$_g$N— wherein R$_f$ and R$_g$ are independently selected from lower alkyl, for example diethylamino, and methyl propylamino, among others.

The term "amino" as used herein refers to H₂N—.

The term "alkoxycarbonyl" as used herein refers to an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" as used herein alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted.

The term "aralkyl", alone or in combination, refers to an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aralkenyl", alone or in combination, refers to an aryl substituted alkenyl radical, wherein the terms "aryl" and "alkenyl" are as defined above.

The term "arylamino", alone or in combination, refers to a radical of formula aryl-NH—, wherein "aryl" is as defined above. Examples of arylamino radicals include, but are not limited to, phenylamino(anilido), naphthlamino, 2-, 3-, and 4- pyridylamino and the like.

The term "biaryl", alone or in combination, refers to a radical of formula aryl-aryl, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aroyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl", alone or in combination, refers to a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, carboxyalkyl, oxo, arylsulfonyl and aralkylaminocarbonyl among others.

The term "alkylheterocyclyl" as used herein refers to an alkyl group as previously defined appended to the parent molecular moiety through a heterocyclyl group.

The term "heterocyclylalkyl" as used herein refers to a heterocyclyl group as previously defined appended to the parent molecular moiety through an alkyl group.

The term "aminal" as used herein refers to the structure $R_hC(NR_iR_j)(NR_kR_l)$— wherein $R_h$, $R_i$, $R_j$, $R_k$ and $R_l$ are each independently hydrogen, alkyl or any other suitable substituent.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1–3 atoms containing any combination of —C—, —C(O)—, —NH—, —S—, —S(O)—, —O—, —C(O)O— or —S(O) O—. Rings may be substituted multiple times.

The terms "electron-withdrawing" or "electron-donating" refer to the ability of a substituent to withdraw or donate electrons relative to that of hydrogen if hydrogen occupied the same position in the molecule. These terms are well-understood by one skilled in the art and are discussed in *Advanced Organic Chemistry* by J. March, 1985, pp. 16–18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the aforesaid substituents may have electron donating or electron withdrawing properties under different chemical conditions. Moreover, the present invention contemplates any combination of substituents selected from the above-identified groups.

The most preferred electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

As used herein, the term "composition" is intended to encompass a product comprising the specified ingredients in the specified amounts, as well as any product which results, directly or indirectly, from a combination of the specified ingredients in the specified amounts.

The term "heteroatom" as used herein encompasses nitrogen, sulfur and oxygen.

The term "alpha" as used herein indicates the position immediately adjacent to the position described.

Abbreviations

Abbreviations which have been used in the reaction schemes and the examples that follow have the following meanings: BOC for t-butyloxycarbonyl, Et₂O for diethyl ether, EtOAc for ethyl acetate, MeOH for methanol, EDC for ethylene dichloride, FMOC for 9-fluorenyl methoxy carbonyl, DMF for dimethylformamide, LAH for lithium aluminum hydride, DEAD for diethylazodicarboxylate and TFA for trifluoroacetic acid.

The compounds of the present invention can be used in the form of pharmaceutically acceptable salts derived from inorganic or organic acids. The phrase "pharmaceutically acceptable salts" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences,* 1977, 66: p. 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quatemized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology,* Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, "Pro-drugs as Novel Delivery Systems", V. 14 of the *A.C.S. Symposium Series,* and in Edward B. Roche, ed., *Bioreversible Carriers in Drug Design,* American Pharmaceutical Association and Pergamon Press (1987), hereby incorporated by reference.

The present invention contemplates both synthetic compounds of formulae I–III of the present invention, as well as compounds formed by in vivo conversion to compounds of the present invention.

Compounds of the present invention may exist as stereoisomers wherein asymmetric or chiral centers are present. These stereoisomers are "R" or "S" depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The present compounds may have activity against disorders which are mediated through the central nervous system. The following references describe various disorders affected by nicotinic acetylcholine receptors: 1) Williams, M.; Arneric, S. P.: "Beyond the Tobacco Debate: dissecting out the therapeutic potential of nicotine" *Exp. Opin. Invest. Drugs* (1996) 5 (8) pp. 1035–1045; 2) Arneric, S. P.; Sullivan, J. P.; Williams, W.: "*Neuronal nicotinic acetylcholine receptors. Novel targets for central nervous system theraputics.*" In: *Psychopharmacology: The Fourth Generation of Progress.* Bloom FE, Kupfer DJ (Eds.), Raven Press, New York (1995): 95–109; 3) Arneric, S. P.; Holladay, M. W.; Sullivan, J. P.: "Cholinergic channel modulators as a novel therapeutic strategy for Alzheimer's disease." *Exp. Opin. Invest. Drugs* (1996) 5 (1): 79–100; 4) Lindstrom, J.: "Nicotinic Acetylchloline Receptors in Health and Disease." *Molecular Neurobiology* (1997) 15: pp. 193–222; and 5) Lloyd, G K; Menzaghi, F; Bontempi B; Suto, C; Siegel, R; Akong, M; Stauderman, K; Velicelebi, G; Johnson, E; Harpold, M M; Rao, T S; Sacaan, A I; Chavez-Noriega, L E; Washburn, M S; Vernier, J M; Cosford, N D P; McDonald, L A: "The potential of subtype-selective neuronal nicotinic acetylcholine receptor agonists as therapeutic agents." *Life Sciences* (1998) 62 (17/18):pp. 1601–1606. These disorders include, but are not limited to the following: pain (references 1 and 2), Alzheimer's disease (references 1–5), Parkinson's disease (references 1, 4 and 5), memory disfunction, Tourette's syndrome (references 1, 2 and 4), sleep disorders (reference 1), attention deficit hyperactivity disorder (references 1 and 3), neurodegeneration, inflammation, neuroprotection (references 2 and 3), amyotrophic atral sclerosis, anxiety (references 1, 2 and 3), depression (reference 2), mania, schizophrenia (references 1, 2 and 4), anorexia and other eating disorders, AIDS-induced dementia, epilepsy (references 1,2 and 4), urinary incontinence (reference 1), Crohn's disease, migraines, PMS, erectile disfunction, substance abuse, smoking cessation (references 1 and 2) and inflammatory bowel syndrome (references 1 and 4) among others.

The compounds and processes of the present invention will be better understood in connection with the following synthetic schemes which illustrate the methods by which the compounds of the invention may be prepared.

The compounds and processes of the present invention will be better understood in connection with the following synthetic schemes which illustrate the methods by which the compounds of the invention may be prepared. As indicated in Scheme 1, a suitably N-protected amino acid may be converted to the corresponding alcohol, by the action of one of several appropriate reducing agents, including for example $BH_3$—THF, $BH_3$—$SMe_2$, DiBAl—H, $LiAlH_4$, and the like. The t-butoxycarbonyl (Boc) group is illustrated, but other standard N-protecting groups can also be used, including for example benzyloxycarbonyl, benzyl, toluenesulfonyl, FMOC, and phthalimido among others. The starting amino acids are chiral, and generally available from commercial sources in either R or S-configuration, as well as in the racemic modification. Since the reduction and subsequent transformations can be achieved while maintaining optical purity, the methods outlined below provide access to individual enantiomers, as well as racemates of the final compounds.

Scheme 1

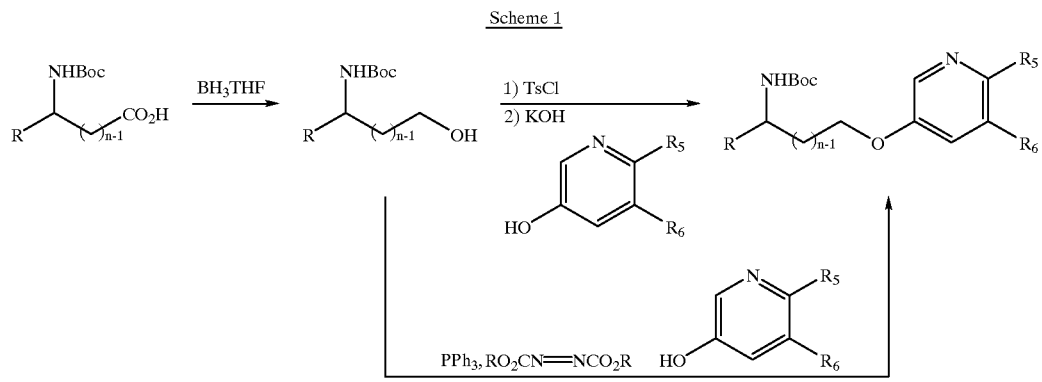

n = 1–4

Formation of the pyridyl ether may be accomplished in two distinct ways. One construct involves activation of the hydroxyl group of the amino alcohol and its subsequent displacement by a substituted hydroypyridine. Thus, as illustrated in Scheme 1, conversion of the alcohol to a good leaving group, such as a sulfonate ester (tosylate, mesylate, etc.) or halides provides suitable activation so that reaction with an hydroxypyridine under basic conditions will produce the ether. Alternatively, activation of the alcohol with triphenylphosphine and a dialkyl azodicarboxylate allows ether formation under neutral conditions.

An alternate mode for pyridyl ether formation is illustrated in Scheme 2.

Scheme 2

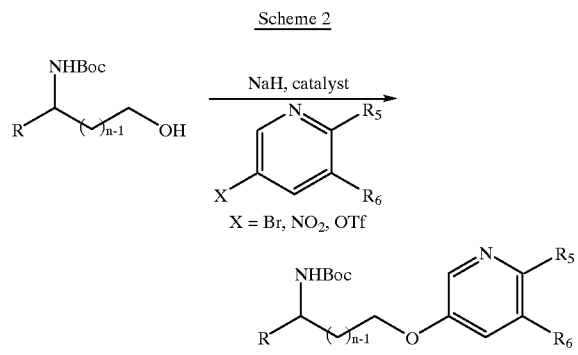

n = 1–4

In this process, the alcohol is engaged in aromatic substitution of a substituted pyridine. Suitable leaving groups on the pyridine include halide, nitro, and trifluoromethanesulfonate. In favorable cases, substitution can be achieved by reaction of the alkoxide, formed from the alcohol by action of sodium or potassium hydride, directly with the substituted pyridine. For less-reactive pyridines, a suitable transition metal catalyst (e.g, palladium or copper complexes) may be used to facilitate the displacement.

Scheme 3 illustrates that deprotection of the amine may be accomplished in conjunction with alkylation to provide a primary, secondary, or tertiary amine, as desired. Thus, alkylation of the Boc-protected amine with a suitable alkyl halide provides for introduction of one alkyl group. Removal of the protecting group under acidic conditions provides the secondary amine, which can be alkylated again with the same or a different alkyl group. Other standard manipulations of the amine also apply, so that amine alkylations can be accomplished via condensation with an aldehyde or ketone with reduction by $NaBH_3CN$, $NaBH_4$, or $H_2$ (reductive amination), or acylation with, e.g., an acyl halide followed by reduction with $LiAlH_4$.

In this manner, the range of nitrogen substituents represented in the invention may be introduced.

Scheme 3

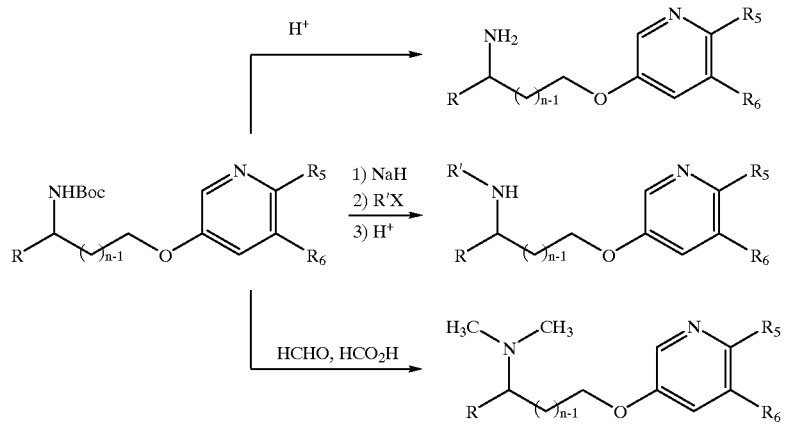

Further elaboration of the pyridine substituents may be accomplished after ether formation as illustrated in Scheme 4. A halide substituent may be activated by palladium catalysis to C—C bond formation with aryl, vinyl and alkynyl tin of boronate derivatives. Likewise, alkenes can be added via the Heck reaction, and a similar process allows incorporation of a nitrile. The products of these initial transformations may be further elaborated according to standard, well-known methods of organic synthesis to provide further compounds of the invention. Another useful method involves lithiation of the halopyridine with trapping of the organolithium intermediate by a suitable electrophile, for example N,N-dimethylformamide for introduction of the formyl group. This can in turn be elaborated in a variety of ways familiar to one skilled in the art, including reduction and addition of suitable organometallic reagents.

The following examples are presented to describe the preferred embodiements and utilities of the invention, and are not meant to limit the invention unless otherwise stated in the claims appended hereto.

EXAMPLE 1

5-[(S)-2-amino-1-propyloxy]-2-chloro pyridine p-toluenesulfonic acid 1 was prepared as follows.

First, 2-[(S)-N-BOC]-propanol 1A was prepared in the following manner. A solution of N-(tert-butoxycarbonyl)-L-alanine (25 g, 132 mmol) in anhydrous THF (150 mL) at 0° C. was treated with borane (1M solution in THF, 200 mL) over a period of 45 minutes. The ice bath was then removed and the reaction mixture was stirred at room temperature for 3 hours. Saturated NaHCO$_3$ solution was added slowly to quench the reaction. The resultant solution was then stirred overnight. Next, solvent was removed under reduced pressure. The remaining water phase was extracted 4× with ethyl

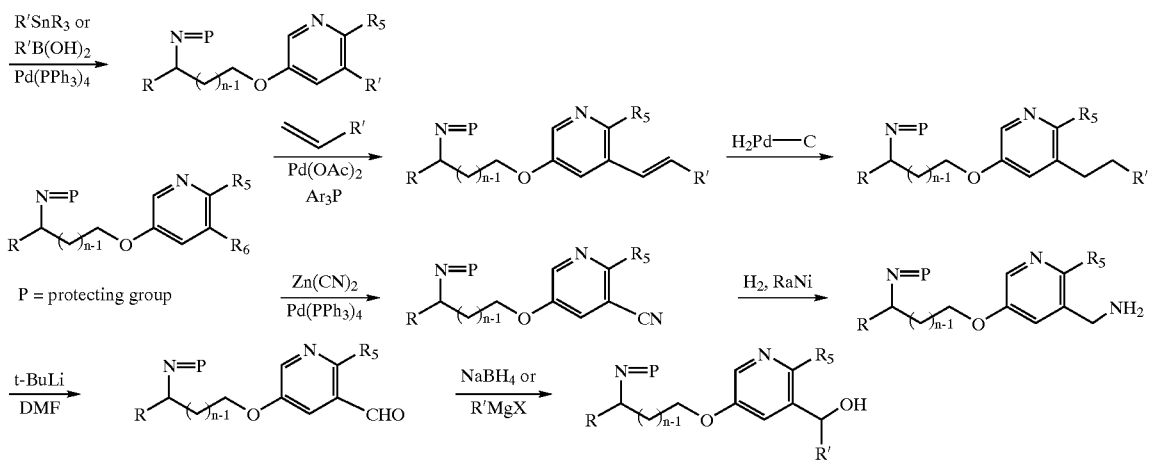

Scheme 4 where R' is H or alkyl ether. The combined ether extract was washed with brine, dried (MgSO$_4$), filtered, and concentrated. The residue was flash chromatographed on silica gel with 30% ethyl acetate/ hexanes to provide a clear oil 1A (69%, 15.9 g). MS (CI/NH$_3$) m/e 176 (M+H)$^+$, 193 (M+NH$_4$)$^+$; $^1$H NMR (CDCl$_3$, 300 MHz) δ: 1.15 (d, J=7 Hz, 3H), 1.45 (s, 9H), 3.51 (q, J=5 Hz, 1H), 3.65 (dd, J=4, 11 Hz, 1H), 3.78 (bs, 1H).

2-[(S)-N-BOC]-propanol tosylate 1B was prepared next in the following manner. A solution of the product 1A (7.30 g, 41.7 mmol) in CH$_2$Cl$_2$ (100 mL) at room temperature was treated with triethylamine (9.3 mL, 66.7 mmol) and p-toluenesulfonyl chloride (9.54 g, 50.1 mmol), stirred overnight. The reaction mixture was diluted with CH$_2$Cl$_2$ to 300 mL, washed with water, 5% NaHCO$_3$, and brine. It was then dried (MgSO$_4$), filtered and concentrated. The residue was flash chromatographed on silica gel with 30% ethyl acetate/hexanes to provide a white solid 1B (61%, 8.40 g). MS (CI/MH$_3$) m/e 330 (M+H)$^+$, 347 (M+NH$_4$)$^+$; $^1$H NMR (CDCl$_3$, 300 MHz) δ: 1.16 (d, J=7 Hz, 3H), 1.40 (s, 9H), 2.45 (s, 3H), 3.92–4.07 (m, 3H), 4.57 (bs, 1H), 7.35 (d, J=8 Hz, 2H), 7.79 (d, J=6 Hz, 2H).

5-[(S)-2-N-BOC-amino-1-propyloxy]-2-chloro pyridine 1C was prepared next in the following manner. A solution of the product 1B (2.35 g, 7.14 mmol) in DMF (47 mL) was treated with potassium hydroxide (1.00 g, 17.9 mmol) and 2-chloro-5-hydroxyl pyridine (1.16 g, 8.93 mmol), stirred at 85° C. overnight. DMF was removed under reduced pressure at 60° C. The residue was dissolved in a mixture of H$_2$O and CH$_2$Cl$_2$. The organic layer was washed with water, and brine. It was then dried (MgSO$_4$), filtered and concentrated. The residue was flash chromatographed on silica gel with 20% ethyl acetate/hexanes to provide a light yellow solid 1C (53%, 1.07 g). MS (CI/MH$_3$) m/e 287 (M+H)$^+$, 304 (M+NH$_4$)$^+$; $^1$H NMR (CDCl$_3$, 300 MHz) δ: 1.30 (d, J=7 Hz, 3H), 1.45 (s, 9H), 3.92–4.14 (m, 3H), 4.68 (bs, 1H), 7.22–7.25 (m, 2H), 8.07 (m, 1H).

5-[(S)-2-amino-1-propyloxy]-2-chloro pyridine p-toluenesulfonic acid 1 was next prepared as follows. A solution of the product 1C (198 mg, 0.691 mmol) in CH$_2$Cl$_2$ (5 mL) was treated with p-toluenesulfonic acid monohydrate (138 mg, 0.726 mmol) and refluxed at 60° C. overnight. Solvent was removed by bubbling nitrogen into the solution. Ethyl ether (30 mL) was added next and stirred for 5 minutes. The ether was then decanted and the procedure was repeated. The residue was then dried under vacuum to provide a white solid 1. mp 110–112° C.; MS (APCI$^+$) m/e 187 (M+H)$^+$; $^1$H NMR (D$_2$O, 500 MHz) δ: 1.42 (d, J=5 Hz, 3H), 2.38 (s, 3H), 3.83 (bs, 1H), 4.11 (t, J=8 Hz, 1H), 4.29 (dd, J=5, 10 Hz, 1H), 7.33 (d, J=5 Hz, 2H), 7.40–7.50 (m, 2H), 7.67 (d, J=10 Hz, 2H), 8.05 (s, 1H); Analysis calculated for C$_8$H$_{11}$ClN$_2$O.1.2C$_7$H$_8$O$_3$S.0.4H$_2$O: C, 49.18; H, 5.39; N, 6.99; Found: C, 49.13; H, 5.55; N, 6.74; [α]$_D^{25}$=+6.1° (c=1.4, MeOH).

EXAMPLE 2

5-[(S)-2-dimethylamino-1-propyloxy]-2-chloro pyridine p-toluenesulfonic acid 2 was synthesized as follows.

5-[(S)-2-dimethylamino-1-propyloxy]-2-chloro-pyridine 2A was prepared as follows. A solution of the product from Example 1C (220 mg, 0.768 mmol) in a mixture of formaldehyde (37 wt. % in water, 8 mL) and formic acid (6 mL) was stirred at 65° C. overnight. The excess reagents were removed under reduced pressure at 45° C. Aqueous NaOH solution (1N) was added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 95/5/0.5 CH$_2$Cl$_2$/MeOH/NH$_4$OH to provide the title compound (65%, 113 mg). MS (CI/NH$_3$) m/e 215 (M+H)$^+$.

5-[(S)-2-dimethylamino-1-propyloxy]-2-chloro pyridine p-toluenesulfonic acid 2 was prepared next as follows.

A solution of the product 2A (100 mg, 0.466 mmol) in ethyl acetate (1 mL) at room temperature was treated with p-toluenesulfonic acid monohydrate (93 mg, 0.489 mmol) and stirred for 5 minutes. Ethyl ether (30 mL) was added next and stirred for additional 5 minutes. The ether was decanted and the procedure was repeated. The residue was then dried under vacuum to provide 2 as a white hygroscopic solid. mp 54–56° C.; MS (APCI$^+$) m/e 215 (M+H)$^+$; $^1$H NMR (D$_2$O, 500 MHz) δ: 1.42 (d, J=5 Hz, 3H), 2.38 (s, 3H), 2.85 (s, 3H), 2.95 (s, 3H), 3.84 (m, 1H), 4.25 (m, 1H), 4.35–4.41 (m, 1H), 7.35 (d, J=5 Hz, 2H), 7.44–7.68 (m, 2H), 7.68 (d, J=15 Hz, 2H), 8.08 (m, 1H); Analysis calculated for C$_{10}$H$_{15}$N$_2$ClO.1.2C$_7$H$_8$O$_3$S.0.4H$_2$O: C, 51.57; H, 5.97; N, 6.54; Found: C, 51.31; H, 5.99; N, 6.55; [α]$^{25}$D=+2.9° (c=2.5, MeOH).

EXAMPLE 3

5-[(S)-2-methylamino-1-propyloxy]-2-chloro pyridine p-toluenesulfonic acid 3 was synthesized as follows.

First, 5-[(S)-2-N-BOC-methylamino-1-propyloxy]-2-chloro pyridine 3A was prepared according to the following procedure.

A solution of the product 1C (190 mg, 0.663 mmol) in THF (10 mL) at room temperature was treated with sodium hydride (60% dispersion in mineral oil, 80 mg, 1.99 mmol) and stirred for 20 minutes. Iodomethane (0.33 mL, 5.31 mmol) was added and stirred at room temperature overnight. The reaction was quenched by adding saturated ammonium chloride solution (6 mL). Saturated sodium carbonate (10 mL) was also added. THF and the excess iodomethane were removed under reduced pressure. Next, the water phase was extracted 3× with CH$_2$Cl$_2$. The combined CH$_2$Cl$_2$ extract was washed with brine, dried (MgSO$_4$), filtered and concentrated. The residue was flash chromatographed on silica gel with 20% ethyl acetate/hexane to provide a light yellow oil as the title compound (80%, 160 mg). MS (CI/NH$_3$) m/e 301 (M+H)$^+$, 318 (M+NH$_4$)$^+$; $^1$H NMR (CDCl$_3$, 300 MHz) δ: 1.25 (d, J=7 Hz, 3H), 1.46 (s, 9H), 2.80 (s, 3H), 3.93 (bs, 1H), 4.01 (m, 1H), 4.56 (bs, 1H), 7.21 (m, 2H), 8.05 (d, J=3 Hz, 1H).

5-[(S)-2-methylamino-1-propyloxy]-2-chloro pyridine p-toluenesulfonic acid 3 was prepared next.

A solution of the product from Example 3A (160 mg, 0.532 numol) in CH$_2$Cl$_2$ (5 mL) was treated with p-toluenesulfonic acid monohydrate (121 mg, 0.639 mmol) and refluxed at 60° C. overnight. Solvent was removed by bubbling nitrogen into the solution. Ethyl ether (30 mL) was added next and stirred for 5 minutes. The ether was decanted and the procedure was repeated. The residue was then dried under vacuum to provide 3 as a white solid. mp 56–58° C.; MS (CI/NH$_3$) m/e 201 (M+H)$^+$; $^1$H NMR (D$_2$O, 500 MHz)

δ: 1.44 (d, J=7 Hz, 3H), 2.37 (s, 3H), 2.77 (s, 3H), 3.72 (m, 1H), 4.17 (m, 1H), 4.34 (m, 1H), 7.33 (d, J=8 Hz, 2H), 7.40–7.47 (m, 2H), 7.67 (d, J=8 Hz, 2H), 8.05 (d, J=3 Hz, 1H); Analysis calculated for $C_9H_{13}N_2ClO.1.4C_7H_8O_3S.0.4H_2O$: C, 50.30; H, 5.61; N, 6.24; Found: C, 50.49; H, 5.90; N, 6.09; $[\alpha]^{25}D=+6.6°$ (c=1.1, MeOH).

EXAMPLE 4

5-[(S)-2-amino-1-propyloxy]-2-fluoro pyridine p-toluenesulfonic acid 4 was synthesized according to the following procedure.

5-[(S)-2-N-BOC-amino-1-propyloxy]-2-fluoro pyridine 4A was first prepared as follows.

A solution of the product 1B (2.25 g, 6.84 mmol) in DMF (40 mL) was treated with potassium hydroxide (960 mg, 17.1 mmol) and 2-fluoro-5-hydroxyl pyridine (970 mg, 8.55 mmol), and stirred at 85° C. overnight. DMF was removed under reduced pressure at 60° C. Next, the residue was dissolved in a mixture of $H_2O$ and $CH_2Cl_2$. The organic layer was washed with water, and brine, then dried ($MgSO_4$), filtered and concentrated. The residue was flash chromatographed on silica gel with 20% ethyl acetate/ hexane to provide a white solid 4A (27%, 500 mg). MS ($CI/NH_3$) m/e 271 $(M+H)^+$, 288 $(M+NH_4)^+$; $^1H$ NMR ($CDCl_3$, 300 MHz) δ: 1.31 (d, J=7 Hz, 3H), 1.46 (s, 9H), 3.97–4.23 (m, 3H), 4.68 (bs, 1H), 6.76 (m, 1H), 7.35(m, 1H), 7.86 (s, 1H).

5-[(S)-2-amino-1-propyloxy]-2-fluoro pyridine 4B was prepared next.

A solution of the product 4A (500 mg, 1.85 mmol) in $CH_2Cl_2$ (15 mL) was treated with trifluoroacetic acid (5 mL) and stirred at room temperature overnight. Solvent and excess reagent were removed under reduced pressure. The residue was then dissolved in saturated sodium carbonate solution and extracted 3× with $CH_2Cl_2$ The combined $CH_2Cl_2$ extract was dried ($MgSO_4$), filtered and concentrated. The residue was flash chromatographed on silica gel with 95/5/0.5 $CH_2Cl_2/CH_3OH/NH_4OH$ to provide a light yellow oil 4B (270 mg, 86%). MS ($CI/NH_3$) m/e 171 $(M+H)^+$, 188 $(M+NH_4)^+$; $^1H$ NMR ($CDCl_3$, 300 MHz) δ: 1.20 (d, J=7 Hz, 3H), 3.38 (m, 1H), 3.73 (dd, J=7, 8 Hz, 1H), 3.91 (dd, J=4, 9 Hz, 1H), 6.85 (dd, J=3, 9 Hz, 1H), 7.34(m, 1H), 7.83 (m, 1H).

5-[(S)-2-amino-1-propyloxy]-2-fluoro pyridine p-toluenesulfonic acid 4 was prepared as follows.

A solution of 4B (87 mg, 0.512 mmol) in ethyl acetate (1 mL) was treated with p-toluenesulfonic acid monohydrate (102 mg, 0.537 mmol) and stirred for 5 minutes. Ethyl ether (30 ml) was added and stirred for an additional 5 minutes. The ether was decanted and the procedure was repeated. The residue was then dried under vacuum to provide 4 as a white solid. mp 139–141° C.; MS ($CI/NH_3$) m/e 171 $(M+H)^+$, 188 $(M+NH_4)^+$; $^1H$ NMR ($D_2O$, 300 MHz) δ: 1.43 (d, J=7 Hz, 3H), 2.41 (s, 3H), 3.84 (m, 1H), 4.12 (dd, J=7, 11 Hz, 1H), 4.32 (dd, J=4, 11 Hz, 1H), 7.09 (dd, J=3, 9 Hz, 1H), 7.38 (d, J=8 Hz, 2H), 7.64 (m, 1H), 7.70 (d, J=8 Hz, 2H), 7.89 (m, 1H). Analysis calculated for $C_8H_{11}N_2FO.C_7H_8O_3S$: C, 52.62; H, 5.59; N, 8.81; Found: C, 52.61; H, 5.79; N, 8.01; $[\alpha]^{25}D=+7.0°$ (c=1.3, MeOH).

EXAMPLE 5

5-[(S)-2-dimethylamino-1-propyloxy]-2-fluoro pyridine p-toluenesulfonic acid 5 was synthesized according to the following procedure.

First, 5-[(S)-2-dimethylamino-1-propyloxy]-2-fluoro pyridine 5A was prepared as follows. A solution of the product 4A (180 mg, 1.06 mmol) in the mixture of formaldehyde (37 wt. % in water, 7 mL) and formic acid (4 mL) was stirred at 65° C. overnight. The excess reagents were removed under reduced pressure at 45° C. Aqueous NaOH solution (1N) was added to the residue and extracted 3× with $CH_2Cl_2$. The combined $CH_2Cl_2$ extract was washed with brine, dried ($MgSO_4$), filtered, and concentrated. The residue was flash chromatographed on silica gel with 95/5/0.5 $CH_2Cl_2/MeOH/NH_4OH$ to provide a light yellow oil 5A (42%, 88 mg). MS ($CI/NH_3$) m/e 199 $(M+H)^+$.

5-[(S)-2-dimethylamino-1-propyloxy]-2-fluoro pyridine p-toluenesulfonic acid 5 was made next as follows.

A solution of 5A (88 mg, 0.444 mmol) in ethyl acetate (1 mL) was treated with p-toluenesulfonic acid monohydrate (89 mg, 0.467 mmol) and stirred for 5 minutes. Ethyl ether (30 mL) was added and stirred for an additional 5 minutes. The ether was decanted and the procedure was repeated. It was then dried under vacuum to provide 5 as a white solid. mp 81–83° C.; MS ($CI/NH_3$) m/e 199 $(M+H)^+$; $^1H$ NMR ($D_2O$, 500 MHz) δ: 1.43 (d, J=7 Hz, 3H), 2.40 (s, 3H), 2.91 (s, 6H), 3.90 (m, 1H), 4.26 (dd, J=8, 11 Hz, 1H), 4.49 (dd, J=4, 11 Hz, 1H), 7.10 (dd, J=2, 9 Hz, 1H), 7.38 (d, J=8 Hz, 2H), 7.65 (m, 1H), 7.70 (d, J=9 Hz, 2H), 8.90 (dd, J=1, 3 Hz, 1H); Analysis calculated for $C_{10}H_{15}N_2FO.1.1C_7H_8O_3S$: C, 54.84; H, 6.19; N, 7.23; Found: C, 54.48; H, 6.35; N, 7.20; $[\alpha]^{25}D=+5.1°$ (c=0.85, MeOH).

EXAMPLE 6

5-[(S)-2-methylamino-1-propyloxy]-2-fluoro pyridine p-touenesulfonic acid 6 was synthesized according to the following procedure. First 5-[(S)-2-N-BOC-methylamino-1-propyloxy]-2-fluoro pyridine 6A was first prepared as follows. A solution of the product 4A (510 mg, 1.89 mmol) in THF (15 mL) was treated with sodium hydride (60% dispersion in mineral oil, 227 mg, 5.67 mmol) and stirred for 20 minutes. Iodomethane (0.94 mL, 15.1 mmol) was added and stirred at room temperature for overnight. The reaction was quenched by adding saturated ammonium chloride solution (6 mL). Saturated sodium carbonate (10 mL) was also added. THF and the excess iodomethane were removed under reduced pressure. The water phase was extracted 3× with $CH_2Cl_2$. The combined $CH_2Cl_2$ extract was washed with brine, dried ($MgSO_4$), filtered and concentrated. The residue was flash chromatographed on silica gel with 10% ethyl acetate/hexane to provide a light yellow oil as the title compound (80%, 320 mg). MS ($CILNH_3$) m/e 285 $(M+H)^+$, 302 $(M+NH_4)^+$; $^1H$ NMR ($CDCl_3$, 300 MHz) δ: 1.25 (d, J=7 Hz, 3H), 1.46 (s, 9H), 2.80 (s, 3H), 3.98 (bs, 2H), 4.53 (bs, 1H), 6.86 (dd, J=3, 9 Hz, 1H), 7.32 (m, 1H), 7.82 (s, 1H).

Next, 5-[(S)-2-methylamino-1-propyloxy]-2-fluoro pyridine p-toluenesulfonic acid 6 was prepared in the following manner.

A solution of the product 6A (320 mg, 1.13 mmol) in $CH_2Cl_2$ (5 mL) was treated with p-toluenesulfonic acid monohydrate (236 mg, 1.24 mmol) and refluxed at 60° C. overnight. Then solvent was removed by bubbling nitrogen into the solution. Ethyl ether (30 mL) was added and stirred for 5 minutes. The ether was decanted and the procedure was repeated. The residue was then dried under vacuum to provide 6 as a white solid. mp 85–87° C.; MS (CI/NH$_3$) m/e 185 (M+H)$^+$, 202 (M+NH$_4$)$^+$; $^1$H NMR (D$_2$O, 500 MHz) δ: 1.45 (d, J=7 Hz, 3H), 2.39 (s, 3H), 2.78 (s, 3H), 3.73 (m, 1H), 4.18 (dd, J=7, 11 Hz, 1H), 4.35 (dd, J=3, 7 Hz, 1H), 7.08 (dd, J=3, 9 Hz, 1H), 7.35 (d, J=8 Hz, 2H), 7.62 (m, 1H), 7.69 (d, J=8 Hz, 2H), 7.87 (dd, J=1, 3 Hz, 1H); Analysis calculated for C$_9$H$_{13}$N$_2$FO.C$_7$H$_8$O$_3$S: C, 53.92; H, 5.94; N, 7.86; Found: C, 53.82; H, 5.79; N, 7.63; [α]$^{25}$D=+8.2° (c=3.5, MeOH).

EXAMPLE 7

5-[(S)-2-amino-1-propyloxy]-2-chloro-3-bromo pyridine p-toluenesulfonic acid 7 was prepared according to the following procedure.

First, 5-[(S)-2-N-BOC-amino-1-propyloxy]-2-chloro-3-bromo pyridine 7A was made as follows. A solution of the product 1B (2.40 g, 7.30 mmol) in DMF (30 mL) was treated with potassium hydroxide (1.02 g, 18.3 mmol) and 2-chloro-3-bromo-5-hydroxyl pyridine (1.90 g, 9.13 mmol) and stirred at 85° C. overnight. DMF was removed under reduced pressure at 60° C. The residue was then dissolved in a mixture of H$_2$O and CH$_2$Cl$_2$. The organic layer was washed 2× with water, and 1× with brine, dried (MgSO$_4$), filtered, and concentrated. It was flash chromatographed on silica gel with 15% ethyl acetate/hexane to provide a white solid 7A (59%, 1.5 g). MS (CI/NH$_3$) m/e 365 (M+H)$^+$, 382 (M+NH$_4$)$^+$; $^1$H NMR (CDCl$_3$, 300 MHz) δ: 1.30 (dd, J=3, 7 Hz, 3H), 1.45 (s, 9H), 3.96–4.11 (mn, 2H), 4.55 (bs, 1H), 7.53(d, J=3 Hz, 1H), 8.06 (m, 1H).

Then 5-[(S)-2-amino-1-propyloxy]-2-chloro-3-bromo pyridine p-toluenesulfonic acid 7 was prepared as follows.

A solution of the product 7A (140 mg, 0.421 mmol) in CH$_2$Cl$_2$ (5 mL) was treated with p-toluenesulfonic acid monohydrate (121 mg, 0.639 mmol) and refluxed at 60° C. overnight. Next, solvent was removed by bubbling nitrogen into the solution. Ethyl ether (30 mL) was then added and stirred for 5 minutes. The ether was decanted and the procedure was repeated. It was then dried under vacuum to provide 7 as a white solid. mp 156–158° C.; MS (CI/NH$_3$) m/e 265 (M+H)$^+$, 282 (M+NH$_4$)$^+$; $^1$H NMR (D$_2$O, 500 MHz) δ: 1.44 (d, J=7 Hz, 3H), 2.39 (s, 3H), 3.85 (m, 1H), 4.14 (dd, J=7, 10 Hz, 1H), 4.32 (dd, J=4, 10 Hz, 1H), 7.36 (d, J=8 Hz, 2H), 7.68 (d, J=8 Hz, 2H), 7.84 (d, J=3 Hz, 1H), 8.09 (d, J=3 Hz, 1H); Analysis calculated for C$_8$H$_{10}$N$_2$BrClO.C$_7$H$_8$O$_3$S: C, 41.16; H, 4.14; N, 6.40; Found: C, 41.15; H, 4.29; N, 6.30; [α]$^{25}$D=+6.9° (c=1.4, MeOH).

EXAMPLE 8

5-[(S)-2-dimethylamino-1-propyloxy]-2-chloro-3-bromo pyridine p-toluenesulfonic acid 8 was prepared according to the following procedure.

First, 5-[(S)-2-dimethylamino-1-propyloxy]-2-chloro-3-bromo pyridine 8A was prepared as follows. A solution of the product 7A (270 mg, 0.739 mmol) in a mixture of formaldehyde (37 wt. % in water, 7 mL) and formic acid (4 mL) was stirred at 65° C. overnight. The excess reagents were removed under reduced pressure at 45° C. Aqueous NaOH solution (1N) was added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 95/5/0.5 CH$_2$Cl$_2$/MeOH/NH$_4$OH to provide 7A as a light yellow oil (61%, 133 mg). MS (CI/NH$_3$) m/e 293 (M+H)$^+$.

Then 5-[(S)-2-dimethylamino-1-propyloxy]-2-chloro-3-bromo pyridine p-toluenesulfonic acid 8 was made as follows.

A solution of 8A (130 mg, 0.442 mmol) in ethyl acetate (1 mL) at room temperature was treated with p-toluenesulfonic acid monohydrate (95 mg, 0.499 mmol) and stirred for 5 minutes. Next, diethyl ether (30 mL) was added and stirred for an additional 5 minutes. The ether was decanted and the procedure was repeated. The residue was then dried under vacuum to provide 8 as a white hygroscopic solid. MS (CI/NH$_3$) m/e 293 (M+H)$^+$; $^1$H NMR (D$_2$O, 500 MHz) δ: 1.44 (d, J=7 Hz, 3H), 2.39 (s, 3H), 2.92 (s, 6H), 3.91 (m, 1H), 4.27 (dd, J=8, 11 Hz, 1H), 4.40 (dd, J=4, 11 Hz, 1H), 7.36 (d, J=8 Hz, 2H), 7.68 (d, J=8 Hz, 2H), 7.86 (d, J=3 Hz, 1H), 8.10 (d, J=3, 1H); Analysis calculated for C$_{10}$H$_{14}$N$_2$BrClO.C$_7$H$_8$O$_3$S: C, 43.84; H, 4.76; N, 6.01; Found: C, 43.93; H, 4.81; N, 5.76; [α]$^{25}$D=+2.5° (c=0.60, MeOH).

EXAMPLE 9

5-[(S)-2-methylamino-1-propyloxy]-2-chloro-3-bromo pyridine p-toluenesulfonic acid 9 was prepared according to the following procedure.

First, 5-[(S)-2-N-BOC-methylamino-1-propyloxy]-2-chloro-3-bromo pyridine 9A was made as follows.

A solution of the product 7A (270 mg, 0.739 mmol) in THF (10 mL) at room temperature was treated with sodium hydride (60% dispersion in mineral oil, 89 mg, 2.22 mmol) and stirred for 20 minutes. Iodomethane (0.37 mL, 5.95 mmol) was then added and stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with CH$_2$Cl$_2$. The combined CH$_2$Cl$_2$ extract was washed with brine, dried (MgSO$_4$), filtered and concentrated. The residue was flash chromatographed on silica gel with 10% ethyl acetate/hexane to provide a light yellow oil 9A (67%, 187 mg). MS (CI/NH$_3$) m/e 379 (M+H)$^+$, 396 (M+NH$_4$)$^+$.

Then 5-[(S)-2-methylamino-1-propyloxy]-2-chloro-3-bromo pyridine p-toluenesulfonic acid 9 was made as follows.

A solution of the product 9A (187 mg, 0.493 mmol) in CH$_2$Cl$_2$ (5 mL) was treated with p-toluenesulfonic acid monohydrate (103 mg, 0.542 mmol) and refluxed at 60° C. overnight. Solvent was removed by bubbling nitrogen into the solution. Next, ethyl ether (30 mL) was added and stirred for 5 minutes. The ether was decanted and the procedure was repeated. The residue was then dried under vacuum to provide 9 as a hygroscopic white solid. mp 48–50° C.; MS (CI/NH$_3$) m/e 279 (M+H)$^+$, 296 (M+NH$_4$)$^+$; $^1$H NMR (D$_2$O, 500 MHz) δ: 1.45 (d, J=7 Hz, 3H), 2.36 (s, 3H), 2.78 (s, 3H), 3.73 (m, 1H), 4.16 (dd, J=7, 11 Hz, 1H), 4.33 (dd, J=3, 11 Hz, 1H), 7.30 (d, J=8 Hz, 2H), 7.65 (d, J=8 Hz, 2H), 7.76 (d, J=3 Hz, 1H), 8.02 (d, J=3 Hz, 1H); Analysis calculated for C$_9$H$_{12}$N$_2$BrClO.C$_7$H$_8$O$_3$S: C, 42.54; H, 4.46; N, 6.20; Found: C, 42.27; H, 4.51; N, 5.95; [α]$^{25}$D=+4.8° (c=4.8, MeOH).

EXAMPLE 10

5-[(S)-2-amino-1-propyloxy]-2-chloro-3-methyl pyridine p-toluenesulfonic acid 10 was synthesized according to the following procedure.

First, 5-[(S)-2-N-BOC-amino-1-propyloxy]-2-chloro-3-methyl pyridine 10A was prepared as follows.

A solution of the product 1B (1.35 g, 4.10 mmol) in DMF (30 mL) was treated with potassium hydroxide (570 mg, 10.2 mmol) and 2-chloro-3-methyl-5-hydroxyl pyridine (730 mg, 5.09 mmol), then stirred at 85° C. overnight. Next, DMF was removed under reduced pressure at 60° C. The residue was dissolved in a mixture of H$_2$O and CH$_2$Cl$_2$. The organic layer was washed with water, and brine. It was then dried (MgSO$_4$), filtered and concentrated. The residue was flash chromatographed on silica gel with 20% ethyl acetate/hexane to provide a white solid 10A (24%, 300 mg). MS (CI/NH$_3$) m/e 301 (M+H)$^+$; $^1$H NMR (CDCl$_3$, 300 MHz) δ: 1.29 (d, J=7 Hz, 3H), 1.45 (s, 9H), 2.35 (s, 3H), 3.95 (d, J=4 Hz, 2H), 4.02 (bs, 1H), 4.68 (bs, 1H), 7.13 (d, J=3 Hz, 1H), 7.92 (d, J×3 Hz, 1H).

5-[(S)-2-amino-1-propyloxy]-2-chloro-3-methyl pyridine p-toluenesulfonic acid 10 was then made as follows. A solution of the product 10A (53 mg, 0.177 mmol) in CH$_2$Cl$_2$ (5 mL) was treated with p-toluenesulfonic acid monohydrate (37 mg, 0.195 mmol) and refluxed at 60° C. overnight. Solvent was removed by bubbling nitrogen into the solution. Ethyl ether (30 mL) was added and stirred for 5 minutes. The ether was decanted and the procedure was repeated. It was then dried under vacuum to provide a white solid 10. mp 181–183° C.; MS (CI/NH$_3$) m/e 201 (M+H)$^+$; $^1$H NMR (D$_2$O, 500 MHz) δ: 1.44 (d, J=7 Hz, 3H), 2.36 (s, 3H), 2.40 (s, 3H), 3.84 (m, 1H), 4.12 (dd, J=7, 11 Hz, 1H), 4.31 (dd, J=3, 11 Hz, 1H), 7.37 (d, J=8 Hz, 2H), 7.44 (d, J=3 Hz, 1H), 7.69 (d, J=8 Hz, 2H), 7.93 (d, J=3 Hz, 1H); Analysis calculated for C$_9$H$_{13}$N$_2$ClO.C$_7$H$_8$O$_3$S: C, 51.54; H, 5.68; N, 7.51; Found: C, 51.53; H, 5.57; N, 7.33; [α]$^{25}$D=+7.0° (c=0.32, MeOH).

EXAMPLE 11

5-[(S)-2-dimethylamino-1-propyloxy]-2-chloro-3-methyl pyridine p-toluenesulfonic acid 11 was synthesized according to the following procedure.

First, 5-[(S)-2-dimethylamino-1-propyloxy]-2-chloro-3-methyl pyridine 11A was made as follows.

A solution of the product 10A (115 mg, 0.383 mmol) in a mixture of formaldehyde (37 wt. % in water, 7 mL) and formic acid (4 mL) was stirred at 65° C. overnight. The excess reagents were removed under reduced pressure at 45° C. Aqueous NaOH solution (1N) was then added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 95/5/0.5 CH$_2$Cl$_2$/MeOH/NH$_4$OH to provide 11A as a light yellow oil (41%, 36 mg). MS (CI/NH$_3$) m/e 229 (M+H)$^+$.

5-[(S)-2-dimethylamino-1-propyloxy]-2-chloro-3-methyl pyridine p-toluenesulfonic acid 11 was then prepared as follows.

A solution of the product 11A (36 mg, 0.158 mmol) in ethyl acetate (1 mL) at room temperature was treated with p-toluenesulfonic acid monohydrate (33 mg, 0.173 mmol) and stirred for 5 minutes. Next, ethyl ether (30 mL) was added and stirred for an additional 5 minutes. The ether was decanted and the procedure was repeated. It was then dried under vacuum to provide 11 as a white hygroscopic solid. mp 58–60° C.; MS (CI/NH$_3$) m/e 229 (M+H)$^+$; $^1$H NMR (D$_2$O, 300 MHz) δ: 1.43 (d, J=7 Hz, 3H), 2.37 (s, 3H), 2.40 (s, 3H), 2.88 (bs, 3H), 2.95 (bs, 3H), 3.87 (m, 1H), 4.25 (m, 1H), 4.41 (m, 1H), 7.38 (d, J=8 Hz, 2H), 7.47 (d, J=3 Hz, 1H), 7.70 (d, J=8 Hz, 2H), 7.95 (d, J=3 Hz, 1H); Analysis calculated for C$_{11}$H$_{17}$N$_2$ClO.1.45C$_7$H$_8$O$_3$S.0.40H$_2$O: C, 52.31; H, 6.10; N, 5.77; Found: C, 52.00; H, 6.12; N, 6.06; [α]$^{25}$D=+3.8° (c=0.21, MeOH).

EXAMPLE 12

5-[(S)-2-methylamino-1-propyloxy]-2-chloro-3-methyl pyridine p-toluenesulfonic acid 12 was synthesized according to the following procedure.

First, 5-[(S)-2-N-BOC-methylamino-1-propyloxy]-2-chloro-3-methyl pyridine 12A was prepared as follows.

A solution of the product 10A (127 mg, 0.423 mmol) in THF (8 mL) at room temperature was treated with sodium hydride (60% dispersion in mineral oil, 51 mg, 1.27 mmol) and stirred for 20 minutes. Iodomethane (0.21 mL, 3.38 mmol) was added and then the solution was stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with CH$_2$Cl$_2$. The combined CH$_2$Cl$_2$ extract was washed with brine, dried (MgSO$_4$), filtered and concentrated. The residue was flash chromatographed on silica gel with 20% ethyl acetate/hexane to provide a light yellow oil 12A (72%, 96 mg). MS (CI/NH$_3$) m/e 315 (M+H)$^+$, 332 (M+NH$_4$)$^+$; $^1$H NMR (CDCl$_3$, 300 MHz) δ: 1.25 (d, J=7 Hz, 3H), 1.46 (s, 9H), 2.35 (s, 3H), 2.80 (s, 3H), 3.89–4.03 (m, 2H), 4.56 (m, 1H), 7.10 (bs, 1H), 7.89 (d, J=3 Hz, 1H).

Next, 5-[(S)-2-methylamino-1-propyloxy]-2-chloro-3-methyl pyridine p-toluenesulfonic acid 12 was prepared as follows.

A solution of the product 12A (96 mg, 0.305 mmol) in CH$_2$Cl$_2$ (5 mL) was treated with p-toluenesulfonic acid monohydrate (64 mg, 0.336 mmol) and then refluxed at 60° C. overnight. Solvent was removed by bubbling nitrogen into the solution. Next, ethyl ether (30 mL) was added and stirred for 5 minutes. The ether was decanted and the procedure was repeated. The residue was then dried under vacuum to provide 12 as a hygroscopic white solid. mp 62–64° C.; MS (CI/NH$_3$) m/e 215 (M+H)$^+$; $^1$H NMR (D$_2$O, 500 MHz) δ: 1.44 (d, J=7 Hz, 3H), 2.37 (s, 3H), 2.41 (s, 3H), 2.77 (s, 3H), 3.72 (m, 1H), 4.19 (dd, J=7, 11 Hz, 1H), 4.37 (dd, J=3, 10 Hz, 1H), 7.33 (d, J=8 Hz, 2H), 7.45 (d, J=3 Hz, 1H), 7.67 (d, J=8 Hz, 2H), 7.94 (d, J=3 Hz, 1H); Analysis calculated for $C_{10}H_{15}N_2ClO.1.25C_7H_8O_3S.0.3H_2O$: C, 51.73; H, 5.93; N, 6.43; Found: C, 51.77; H, 5.68; N, 6.32; $[\alpha]^{25}D=+6.9°$ (c=2.2, MeOH).

EXAMPLE 13

5-[(S)-2-amino-1-propyloxy]-2-chloro-3-(4-vinylpyridinyl)pyridine p-toluenesulfonic acid 13 was synthesized according to the following procedure.

First, 5-[(S)-2-N-BOC-amino-1-propyloxyl-2-chloro-3-(4-vinylpyridinyl)pyridine 13A was prepared as follows.

A solution of the product 7A (620 mg, 1.70 mmol), 4-vinyl pyridine (0.23 mL, 2.12 mmol), palladium (II) acetate (16 mg, 0.071 mmol), tri-o-tolylphosphine (44 mg, 0.145 mmol), and triethylamine (0.85 mL, 6.12 mmol) in acetonitrile (10 mL) was refluxed at 100° C. overnight. The reaction mixture was diluted with ethyl acetate, washed with saturated sodium carbonate, brine, dried (MgSO$_4$), filtered and concentrated. Then residue was flash chromatographed with 30% ethyl acetate/hexane to provide 13A as a white solid (73%, 480 mg); MS (CI/NH$_3$) m/e 390 (M+H)$^+$.

Next, 5-[(S)-2-amino-1-propyloxy]-2-chloro-3-(4-vinylpyridinyl)pyridine 13B was prepared as follows.

A solution of the product 13A (120 mg, 0.308 mmol) in CH$_2$Cl$_2$ (4 mL) was treated with trifluoroacetic acid (1 mL) and then stirred at room temperature overnight. Solvent and the excess reagent were removed under reduced pressure. The residue was dissolved in saturated sodium carbonate solution and extracted 3× with CH$_2$Cl$_2$ The combined CH$_2$Cl$_2$ extract was dried (MgSO$_4$), filtered and concentrated. The residue was flash chromatographed on silica gel with 95/5/0.5 CH$_2$Cl$_2$/CH$_3$OH/NH$_4$OH to provide a light yellow oil 13B (79%, 70 mg). MS (CI/NH$_3$) m/e 290 (M+H)$^+$.

Then 5-[(S)-2-amino-1-propyloxy]-2-chloro-3-(4-vinylpyridinyl)pyridine p-toluenesulfonic acid 13 was prepared as follows. A solution of the product 13B (70 mg, 0.242 mmol) in ethyl acetate (1 mL) was treated with p-toluenesulfonic acid monohydrate (51 mg, 0.266 mmol) and stirred for 5 minutes. Next, ethyl ether (30 mL) was added and stirred for an additional 5 minutes. The ether was decanted and the procedure was repeated. It was then dried under vacuum to provide 13 as a light yellow solid. mp 69–71° C.; MS (CI/NH$_3$) m/e 290 (M+H)$^+$; $^1$H NMR (D$_2$O, 500 MHz) δ: 1.48 (d, J=7 Hz, 3H), 2.35 (s, 3H), 3.87 (m, 1H), 4.14 (m, 1H), 4.31 (dd, J=4, 10 Hz, 1H), 7.10 (d, J=6 Hz, 2H), 7.29 (d, J=8 Hz, 2H), 7.45 (d, J=16 Hz, 2H), 7.64 (d, J=8 Hz, 2H), 7.68 (d, J=3 Hz, 1H), 7.93 (d, J=3 Hz, 1H), 8.45 (d, J=6 Hz, 2H); Analysis calculated for $C_{15}H_{16}N_3ClO.1.65C_7H_8O_3S.1.15H_2O$: C, 53.63; H, 5.34; N, 7.07; Found: C, 53.83; H, 5.25; N, 6.77; $[\alpha]^{25}D=+1.3°$ (c=0.75, MeOH).

EXAMPLE 14

5-[(S)-2-N-dimethylamino-1-propyloxy]-2-chloro-3-(4-vinylpyridinyl)pyridine p-toluenesulfonic acid 14 was prepared according to the following procedure.

First, 5-[(S)-2-N-dimethylamino-1-propyloxy]-2-chloro-3-(4-vinylpyridinyl)pyridine 14A was made as follows.

A solution of the product 13A (220 mg, 0.564 mmol) in a mixture of formaldehyde (37 wt. % in water, 7 mL) and formic acid (4 mL) was stirred at 65° C. overnight. The excess reagents were removed under reduced pressure at 45° C. Aqueous NaOH solution (1N) was added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 95/5/0.5 CH$_2$Cl$_2$/MeOH/NH$_4$OH to provide 14A as a light yellow oil (99%, 163 mg). MS (CI/NH$_3$) m/e 318 (M+H)$^+$.

5-[(S)-2-N-dimethylamino-1-propyloxy]-2-chloro-3-(4-vinylpyridinyl)pyridine p-toluenesulfonic acid 14 was then made as follows.

A solution of the product 14A (133 mg, 0.420 mmol) in ethyl acetate (1 mL) at room temperature was treated with p-toluenesulfonic acid monohydrate (88 mg, 0.462 mmol) and stirred for 5 minutes. Ethyl ether (30 mL) was added and stirred for an additional 5 minutes. The ether was decanted and the procedure was repeated. The residue was then dried under vacuum to provide 14 as a light yellow solid. mp 79–81° C.; MS (CI/NH$_3$) m/e 318 (M+H)$^+$; $^1$H NMR (D$_2$O, 500 MHz) δ: 1.46 (d, J=7 Hz, 3H), 2.33 (s, 3H), 2.90 (s, 3H), 2.98 (s, 3 Hz, 6H) 3.93 (m, 1H), 4.30 (dd, J=8, 11 Hz, 1H), 4.42 (m, 1H), 7.23 (s, 1H), 7.27 (d, J=8 Hz, 2H), 7.62 (d, J=8, 2H), 7.69 (d, J=16 Hz, 1H), 7.75 (d, J=2 Hz, 1H), 7.96 (d, J=7 Hz, 2H), 8.08 (d, J=3 Hz, 1H), 8.59 (d, J=6 Hz, 2H); Analysis calculated for $C_{17}H_{20}N_3ClO.1.5C_7H_8O_3S.0.75H_2O$: C, 56.02; H, 5.73;N, 7.13; Found: C, 56.23; H, 5.72; N, 6.83; $[\alpha]^{25}D=+0.80°$ (c=1.0, MeOH).

EXAMPLE 15

5-[(S)-2-amino-1-butyloxy]-2-chloro pyridine p-toluenesulfonic acid 15 was synthesized according to the following procedure.

First, 2-[(S)-N-BOC]-butanol 15A was prepared as follows. A solution of N-(tert-butoxycarbonyl-L-α-aminobutyric acid (15 g, 73.8 mmol) in anhydrous THF (100 mL) at 0° C. was treated with borane (1M solution in THF, 200 mL) over a period of 45 minutes. The ice bath was then removed and the reaction mixture was stirred at room temperature for 3 hours. Saturated NaHCO$_3$ solution was added slowly to quench the reaction. The resultant solution was then stirred overnight. Next, solvent was removed under reduced pressure. The remaining water phase was extracted 4× with ethyl ether. The combined ether extract was washed with brine, dried (MgSO$_4$), filtered, and concentrated. The residue was flash chromatographed on silica gel with 30% ethyl acetate/hexane to provide a clear oil 15A (55%, 7.73 g). MS (CI/NH$_3$) m/e 190 (M+H)$^+$, 207 (M+NH$_4$)$^+$; $^1$H NMR (CDCl$_3$, 300 MHz) δ: 0.96 (t, J=7 Hz, 3H), 1.45 (s, 9H), 1.39–1.67 (m, 2H), 3.52–3.59 (m, 2H), 3.69 (m, 1H), 4.61 (bs, 1H).

Next, 2-[(S)-N-BOC]-butanol tosylate 15B was prepared as follows.

A solution of the product 15A (7.60 g, 40.2 mmol) in CH$_2$Cl$_2$ (150 mL) at room temperature was treated with triethylamine (8.9 mL, 66.3 mmol) and p-toluenesulfonyl chloride (9.58 g, 50.3 mmol), and then stirred overnight. The reaction mixture was diluted with $CH_2Cl_2$ to 300 mL, washed with water, 5% $NaHCO_3$, and brine. It was then dried ($MgSO_4$), filtered and concentrated. The residue was flash chromatographed on silica gel with 15% ethyl acetate/hexane to provide 15B (58%, 8.01 g). MS ($CI/NH_3$) m/e 344 $(M+H)^+$, 361 $(M+NH_4)^+$; $^1H$ NMR ($CDCl_3$, 300 MHz) δ: 0.88 (t, J=8 Hz, 3H), 1.41 (s, 9H), 1.45–1.55 (m, 2H), 2.45 (s, 3H), 3.65 (bs, 1H), 3.97–4.07 (m, 2H), 4.56 (m, 1H), 7.36 (d, J=8 Hz, 2H), 7.79 (d, J=6 Hz, 2H).

Then 5-[(S)-2-N-BOC-amino-1-butyloxy]-2-chloro pyridine 15C was prepared as follows.

A solution of the product from Example 15B (1.38 g, 4.02 mmol) in DMF (20 mL) was treated with potassium hydroxide (338 mg, 6.03 mmol) and 2-chloro-5-hydroxyl pyridine (651 mg, 5.03 mmol), and then stirred at 85° C. overnight. DMF was removed under reduced pressure at 60° C. The residue was dissolved in a mixture of $H_2O$ and $CH_2Cl_2$. The organic layer was washed with water, and brine. It was then dried ($MgSO_4$), filtered and concentrated. The residue was flash chromatographed on silica gel with 20% ethyl acetate/hexane to provide a light yellow solid 15C (11%, 130 mg). MS ($CI/NH_3$) mn/e 301 $(M+H)^+$, 318 $(M+NH_4)^+$; $^1H$ NMR ($CDCl_3$, 300 MHz) δ: 0.99 (t, J=7 Hz, 3H), 1.45 (s, 9H), 1.59–1.75 (m, 2H), 3.85 (m, 1H), 4.00 (d, J=4 Hz, 2H), 4.67 (bs, 1H), 7.22 (s, 2H), 8.06 (d, J=2 Hz, 1H).

Then, 5-[(S)-2-amino-1-butyloxy]-2-chloro pyridine p-toluenesulfonic acid 15 was prepared as follows.

A solution of the product 15C (127 mg, 0.423 mmol) in $CH_2Cl_2$ (5 mL) was treated with p-toluenesulfonic acid monohydrate (88 mg, 0.463 mmol) and refluxed at 60° C. overnight. Then, solvent was removed by bubbling nitrogen into the solution. Next, ethyl ether (30 mL) was added and stirred for 5 minutes. The ether was decanted and the procedure was repeated. The residue was then dried under vacuum to provide a light yellow solid 15. mp145–147 ° C.; MS ($CI/NH_3$) m/e 201 $(M+H)^+$, 218 $(M+NH_4)^+$; $^1H$ NMR ($D_2O$, 500 MHz) δ: 1.06 (t, J=7 Hz, 3H), 1.78–1.90 (m, 2H), 2.39 (s, 3H), 3.67 (m, 1H), 4.20 (dd, J=7, 11 Hz, 1H), 4.35 (dd, J=3, 12 Hz, 1H), 7.36 (d, J=8 Hz, 2H), 7.44 (d, J=8 Hz, 1H), 7.49 (dd, J=3, 9 Hz, 1H), 7.70 (d, J=8 Hz, 2H), 8.09 (d, J=3 Hz, 1H); Analysis calculated for $C_9H_{13}N_2ClO·1.25C_7H_8O_3S$: C, 51.26; H, 5.57; N, 6.74; Found: C, 51.15; H, 5.29; N, 6.67; $[\alpha]^{25}D$=+11.7° (c=0.60, MeOH).

EXAMPLE 16

5-[(S)-2-amino-1-butyloxy]-2-fluoro pyridine p-toluenesulfonic acid 16 was synthesized according to the following procedure.

First, 5-[(S)-2-N-BOC-amino-1-butyloxy]-2-fluoro pyridine 16A was prepared as follows.

A solution of the product from Example 15B (1.41 g, 4.11 mmol) in DMF (30 mL) was treated with potassium hydroxide (575 mg, 10.3 mmol) and 2-fluoro-5-hydroxyl pyridine (581 mg, 5.14 mmol), stirred at 85° C. for overnight. DMF was removed under reduced pressure at 60° C. The residue was dissolved in a mixture of $H_2O$ and $CH_2Cl_2$. The organic layer was washed with water, and brine. It was then dried ($MgSO_4$), filtered and concentrated. The residue was flash chromatographed on silica gel with 20% ethyl acetate/hexane to provide a light yellow solid 16A (13%, 152 mg). MS ($CI/NH_3$) m/e 285 $(M+H)^+$, 302 $(M+NH_4)^+$; $^1H$ NMR ($CDCl_3$, 300 MHz) δ: 0.99 (t, J=8 Hz, 3H), 1.45 (s, 9H), 1.59–1.78 (m, 2H), 3.85 (m, 1H), 4.00 (d, J=4 Hz, 2H), 4.67 (bs, 1H), 6.86 (dd, J=3, 8 Hz, 1H), 7.39 (m, 1H), 7.82 (s, 1H).

5-[(S)-2-amino-1-butyloxy]-2-fluoro pyridine p-toluenesulfonic acid 16 was then prepared as follows.

A solution of the product 16A (75 mg, 0.264 mmol) in $CH_2Cl_2$ (5 mL) was treated with p-toluenesolfonic acid monohydrate (55 mg, 0.289 mmol) and then refluxed at 60° C. overnight. Next, solvent was removed by bubbling nitrogen into the solution. Ethyl ether (30 mL) was added and stirred for 5 minutes. The ether was decanted and the procedure was repeated. The residue was then dried under vacuum to provide a white solid 16. mp 140–142° C.; MS ($CI/NL_3$) m/e 185 $(M+H)^+$, 202 $(M+NH_4)^+$; $^1H$ NMR ($D_2O$, 500 MHz) δ: 1.06 (t, J=7 Hz, 3H), 1.78–1.90 (m, 2H), 2.40 (s, 3H), 3.65 (m, 1H), 4.18 (dd, J=7, 8 Hz, 1H), 4.35 (m, J=3 Hz, 1H), 7.08 (m, 1H), 7.37 (d, J=8 Hz, 2H), 7.62 (bs, 1H), 7.79 (d, J=8 Hz, 2H), 7.88 (d, J=1 Hz, 1H); Analysis calculated for $C_9H_{13}N_2FO·C_7H_8O_3S$: C, 53.92; H, 5.94; N, 7.86; Found: C, 53.72; H, 5.96; N, 7.65; $[\alpha]^{25}D$=+8.8° (c=0.60, MeOH).

EXAMPLE 17

5-[(S)-2-methylamino-1-butyloxy]-2-fluoro pyridine p-toluenesulfonic acid 17 was synthesized according to the following procedure.

First, 5-[(S)-2-N-BOC-methylamino-1-butyloxy]-2-fluoro pyridine 17A was prepared as follows.

A solution of the product 16A (170 mg, 0.493 mmol) in THF (10 mL) at room temperature was treated with sodium hydride (60% dispersion in mineral oil, 59 mg, 1.48 mmol) and stirred for 20 minutes. Then iodomethane (0.25 mL, 3.94 mmol) was added and stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with $CH_2Cl_2$. The combined $CH_2Cl_2$ extract was washed with brine, dried ($MgSO_4$), filtered and concentrated. The residue was flash chromatographed on silica gel with 15% ethyl acetate/hexane to provide a light yellow oil 17A (79%, 116 mg). MS ($CI/NH_3$) m/e 299 $(M+H)^+$, 316 $(M+NH_4)^+$.

Then 5-[(S)-2-methylamino-1-butyloxy]-2-fluoro pyridine p-toluenesulfonic acid 17 was made as follows.

A solution of the product 17A (116 mg, 0.389 nunol) in $CH_2Cl_2$ (5 mL) was treated with p-toluenesulfonic acid monohydrate (81 mg, 0.426 mmol) and refluxed at 60° C. overnight. Then solvent was removed by bubbling nitrogen into the solution. Next, ethyl ether (30 mL) was added and stirred for 5 minutes. The ether was decanted and the procedure was repeated. It was then dried under vacuum to provide 17. MS ($CI/NH_3$) m/e 199 $(M+H)^+$, 216 $(M+NH_4)^+$; $^1H$ NMR ($D_2O$, 500 MHz) δ: 1.04 (t, J=7 Hz, 3H), 1.80–1.94 (m, 2H), 2.37 (s, 3H), 2.79 (s, 3H), 3.52 (m, 1H), 4.25 (dd, J=6, 11 Hz, 1H), 4.37 (dd, J=3, 11 Hz, 1H), 7.06 (dd, J=3, 9 Hz, 1H), 7.34 (d, J=8 Hz, 2H), 7.60 (m, 1H), 7.67 (d, J=8

Hz, 2H), 7.86 (dd, J=1, 3 Hz, 1H); Analysis calculated for $C_{10}H_{15}N_2FO·C_7H_8O_3S$: C, 55.12; H, 6.26; N, 7.56; Found: C, 54.73; H, 6.07; N, 7.20; $[\alpha]^{25}D$=+8.9° (c=1.2, MeOH).

EXAMPLE 18

5-[(S)-2-amino-1-butyloxy]-2-chloro-3-bromo pyridine p-toluenesulfonic acid 18 was synthesized according to the following procedure.

First, 5-[(S)-2-N-BOC-amino-1-butyloxy]-2-chloro-3-bromo pyridine 18A was prepared as follows.

A solution of the product 15B (3.16 g, 9.21 mmol) in DMF (40 mL) was treated with potassium hydroxide (1.29 g, 23.0 mmol) and 2-chloro-3-bromo-5-hydroxyl pyridine (2.40 g, 11.5 mmol), stirred at 85° C. overnight. Then DMF was removed under reduced pressure at 60° C. The residue was dissolved in a mixture of $H_2O$ and $CH_2Cl_2$. The organic layer was washed with water, and brine. It was then dried ($MgSO_4$), filtered and concentrated. The residue was flash chromatographed on silica gel with 15% ethyl acetate/hexane to provide a light yellow solid 18A (10%, 345 mg). MS ($CI/NH_3$) m/e 379 (M+H)+; $^1H$ NMR ($CDCl_3$, 300 MHz) δ: 0.99 (t, J=7 Hz, 3H), 1.45 (s, 9H), 1.59–1.78 (m, 2H), 3.85 (m, 1H), 4.01 (d, J=4 Hz, 2H), 4.67 (bs, 1H), 7.52 (d, J=3 Hz, 1H), 8.05 (d, J=3 Hz, 1H).

5-[(S)-2-amino-1-butyloxy]-2-chloro-3-bromo pyridine p-toluenesulfonic acid 18 was then prepared as follows.

A solution of the product 18A (52 mg, 0.137 mmol) in $CH_2Cl_2$ (5 mL) was treated with p-toluenesulfonic acid monohydrate (29 mg, 0.153 mmol) and refluxed at 60° C. overnight. Then solvent was removed by bubbling nitrogen into the solution. Ethyl ether (30 mL) was added and stirred for 5 minutes. The ether was decanted and the procedure was repeated. The residue was then dried under vacuum to provide a white solid 18. mp 141–143° C.; MS ($CI/NH_3$) m/e 279 (M+H)+; $^1H$ NMR ($D_2O$, 400 MHz) δ: 1.06 (t, J=8 Hz, 3H), 1.80–1.90 (m, 2H), 2.40 (s, 3H), 3.65 (m, 1H), 4.21 (dd, J=7, 11 Hz, 1H), 4.35 (dd, J=3, 10 Hz, 1H), 7.36 (d, J=8 Hz, 2H), 7.68 (d, J=8 Hz, 2H), 7.85 (d, J=3 Hz, 1H), 8.11 (d, J=3 Hz, 1H); Analysis calculated for $C_9H_{12}N_2BrClO·C_7H_8O_3S$: C, 42.54; H, 4.46; N, 6.20; Found: C, 42.62; H, 4.52; N, 6.14; $[\alpha]^{25}D$=+12.7° (c=0.30, MeOH).

EXAMPLE 19

5-[(S)-2-amino-1-butyloxy]-2-chloro-3-(4-vinylpyridinyl)pyridine di-p-toluenesulfonic acid 19 was synthesized as follows.

First, 5-[(S)-2-N-BOC-amino-1-butyloxy]-2-chloro-3-(4-vinylpyridinyl)pyridine 19A was made as follows.

A solution of the product 18A (285 mg, 0.751 mmol), 4-vinyl pyridine (0.12 mL, 1.13 mmol), palladium (II) acetate (17 mg, 0.075 mmol), tri-o-tolylphosphine (46 mg, 0.15 mmol), and triethylamine (0.37 mL, 2.70 mmol) in acetonitrile (10 mL) was refluxed at 100° C. overnight. The reaction mixture was then diluted with ethyl acetate, washed with saturated sodium carbonate, brine, dried ($MgSO_4$), filtered and concentrated. The residue was flash chromatographed with 30% ethyl acetate/hexane to provide 19A as a white solid (89%, 271 mg); MS ($CI/NH_3$) m/e 404 (M+H)+.

Then 5-[(S)-2-amino-1-butyloxy]-2-chloro-3-(4-vinylpyridinyl)pyridine di-p-toluenesulfonic acid 19 was prepared as follows.

A solution of the product 19A (111 mg, 0.273 mmol) in ethyl acetate (1 mL) was treated with p-toluenesulfonic acid monohydrate (110 mg, 0.579 mmol) and stirred for 5 minutes. Next, ethyl ether (30 mL) was added and stirred for an additional 5 minutes. The ether was decanted and the procedure was repeated. The residue was then dried under vacuum to provide 19 as a light yellow solid. mp 101–103° C.; MS ($CI/NH_3$) m/e 304 (M+H)+; $^1H$ NMR ($D_2O$, 400 MHz) δ: 1.08 (t, J=7 Hz, 3H), 1.82–1.91 (m, 2H), 2.33 (s, 3H), 3.68 (m, 1H), 4.24–4.27 (dd, J=7, 11 Hz, 1H), 4.39 (dd, J=3, 11 Hz, 1H), 7.23–7.31 (m, 4H), 7.61 (d, J=8 Hz, 4H), 7.72–7.78 (m, 2H), 8.05 (d, J=8 Hz, 4H), 8.63 (d, J=7 Hz, 2H); Analysis calculated for $C_{16}H_{18}N_3ClO·2.20C_7H_8O_3S·1.40H_2O$: C, 53.28; H, 5.47; N, 5.94; Found: C, 53.29; H, 5.37; N, 5.81; $[\alpha]^{25}D$=+3.3° (c=1.3, MeOH).

EXAMPLE 20

5-[(S)-2-N-dimethylamino-1-butyloxy]-2-chloro-3-(4-vinylpyridinyl)pyridine di-p-toluenesulfonic acid 20 was synthesized as follows.

First, 5-[(S)-2-N-dimethylamino-1-butyloxy]-2-chloro-3-(4-vinylpyridinyl)pyridine 20A was made as follows.

A solution of the product 19A (160 mg, 0.397 mmol) in a mixture of formaldehyde (37 wt. % in water, 7 mL) and formic acid (4 mL) was stirred at 65° C. overnight. The excess reagents were removed under reduced pressure at 45° C. Aqueous NaOH solution (1N) was added to the residue and extracted 3× with $CH_2Cl_2$. The combined $CH_2Cl_2$ extract was washed with brine, dried ($MgSO_4$), filtered, and concentrated. The residue was flash chromatographed on silica gel with 95/5 $CH_2Cl_2$/MeOH to provide 20A as a light yellow oil (63%, 83 mg). MS ($CI/NH_3$) m/e 332 (M+H)+.

Then 5-[(S)-2-N-dimethylamino-1-butyloxy]-2-chloro-3-(4-vinylpyridinyl)pyridine di-p-toluenesulfonic acid 20 was made as follows.

A solution of the product 20A (39 mg, 0.118 mmol) in ethyl acetate (1 mL) at room temperature was treated with p-toluenesulfonic acid monohydrate (47 mg, 0.247 mmol) and stirred for 5 minutes. Then ethyl ether (30 mL) was added and stirred for an additional 5 minutes. The ether was decanted and the procedure was repeated. The residue was then dried under vacuum to provide 20 as a light yellow solid. mp 73–75° C.; MS (ESI+) m/e 332 (M+H)+; $^1H$ NMR ($D_2O$, 400 MHz) δ: 1.09 (t, J=8 Hz, 3H), 1.80–2.00 (m, 2H), 2.34 (s, 3H), 2.93 (s, 3H), 2.99 (s, 3H), 3.68 (m, 1H), 4.39 (dd, J=7, 11 Hz, 1H), 4.52 (dd, J=3, 11 Hz, 1H), 7.27 (d, J=8 Hz, 4H), 7.31 (s, 1H), 7.62 (d, J=18 Hz, 4H), 7.76 (d, J=2 Hz, 1H), 7.79 (d, J=3 Hz, 2H), 8.08–8.10 (m, 2H), 8.65 (d, J=6 Hz, 2H); Analysis calculated for $C_{18}H_{22}N_3ClO·2.30C_7H_8O_3S·2.50H_2O$: C, 52.99; H, 5.92; N, 5.44; Found: C, 53.38; H, 5.89; N. 5.04; $[\alpha]^{25}D$=+0.6.4° (c=1.1, MeOH).

EXAMPLE 21

5-[(S)-2-amino-3-phenyl-1-propyloxy]-2-chloro-3-bromo pyridine p-toluenesulfonic acid 21 was synthesized according to the following procedure.

First, 2-[(S)-N-BOC]-3-phenyl-butanol 21A was made as follows.

A solution of N-(tert-butoxycarbonyl-L-phenylalanine (25.3 g, 95.5 mmol) in anhydrous THF (120 mL) at 0° C.

was treated with borane (1M solution in THF, 143 mL) over a period of 45 minutes. The ice bath was then removed and the reaction mixture was stirred at room temperature for 3 hours. Then saturated NaHCO$_3$ solution was added slowly to quench the reaction, and the resultant solution was stirred overnight. Next, solvent was removed under reduced pressure. The remaining water phase was extracted 4× with ethyl ether. The combined ether extract was washed with brine, dried (MgSO$_4$), filtered, and concentrated. The residue was flash chromatographed on silica gel with 30% ethyl acetate/hexane to provide a white solid 21A (43%, 9.80 g). MS (CI/NH$_3$) m/e 252 (M+H)$^+$, 269 (M+NH$_4$)$^+$; $^1$H NMR (CDCl$_3$, 300 MHz) δ: 1.42 (s, 9H), 2.85 (d, J=7 Hz, 2H), 3.56 (dd, J=5, 11 Hz, 1H), 3.68 (dd, J=4, 11 Hz, 1H), 3.86 (bs, 1H), 4.72 (bs, 1H), 7.16–7.33 (m, 5H).

Then 2-[(S)-N-BOC]-3-phenyl-propanol tosylate 21B was prepared as follows.

A solution of the product from Example 21A (9.80 g, 39.0 mmol) in CH$_2$Cl$_2$ (200 mL) at room temperature was treated with triethylamine (8.66 mL, 62.4 mmol) and p-toluenesulfonyl chloride (9.30 g, 48.8 mmol), and then stirred overnight. The reaction mixture was diluted with CH$_2$Cl$_2$ to 300 mL, washed with water, 5% NaHCO$_3$, and brine. It was then dried (MgSO$_4$), filtered and concentrated. The residue was flash chromatographed on silica gel with 20% ethyl acetate/hexane to provide a white solid 21B (63%, 10.0 g). MS (CI/NH$_3$) m/e 423 (M+NH$_4$)$^+$; $^1$H NMR (CDCl$_3$, 300 MHz) δ: 1.39 (s, 9H), 2.46 (s, 3H), 2.72–2.90 (bs, 2H), 3.84–4.05 (m, 3H), 4.72 (bs, 1H), 7.03–7.09 (m, 2H), 721–7.26 (m, 3H), 7.30 (d, J=8 Hz, 2H), 7.79 (d, J=7 Hz, 2H).

Next, 5-[(S)-2-N-BOC-amino-3-phenyl-1-propyloxy]-2-chloro-3-bromo pyridine 21C was prepared as follows.

A solution of the product 21B (3.53 g, 8.63 mmol) in DMF (40 mL) was treated with potassium hydroxide (1.21 g, 21.6 mmol) and 2-chloro-3-bromo-5-hydroxyl pyridine (2.25 g, 10.8 mmol), and then stirred at 85° C. overnight. DMF was removed under reduced pressure at 60° C. The residue was dissolved in a mixture of H$_2$O and CH$_2$Cl$_2$. The organic layer was washed with water, and brine. It was then dried (MgSO$_4$), filtered and concentrated. The residue was flash chromatographed on silica gel with 15% ethyl acetate/hexane to provide a white solid 21C (46%, 1.75 g). MS (CI/NH$_3$) m/e 441 (M+H)$^+$; $^1$H NMR (CDCl$_3$, 300 MHz) δ: 1.43 (s, 9H), 2.90–3.04 (m, 2H), 3.87–3.98 (m, 2H), 4.18 (bs, 1H), 4.82 (bs, 1H), 7.05–7.33 (m, 5H), 7.48 (d, J=3 Hz, 1H), 8.04 (d, J=3 Hz, 1H).

5-[(S)-2-amino-3-phenyl-1-propyloxy]-2-chloro-3-bromo pyridine p-toluenesulfonic acid 21 was then prepared as follows.

A solution of the product from Example 21C (137 mg, 0.310 mmol) in CH$_2$Cl$_2$ (5 mL) was treated with p-toluenesulfonic acid monohydrate (65 mg, 0.342 mmol) and refluxed at 60° C. overnight. Next, solvent was removed by bubbling nitrogen into the solution. Ethyl ether (30 mL) was added and stirred for 5 minutes. The ether was decanted and the procedure was repeated. It was then dried under vacuum to provide a white solid as 21. mp162–164° C.; MS (EST$^+$) m/e 341 (M+H)$^+$; $^1$H NMR (D$_2$O, 400 MHz) δ: 2.40 (s, 3H), 3.16 (d, J=8 Hz, 2H), 3.99 (m, 1H), 4.14 (dd, J=6, 11 Hz, 1H), 4.30 (dd, J=3, 12 Hz, 1H), 7.32–7.46 (m, 7H), 7.68–7.80 (m, 2H), 7.81 (d, J=3 Hz, 1H), 8.08 (d, J=3 Hz, 1H); Analysis calculated for C$_{14}$H$_{14}$N$_2$BrClO.C$_7$H$_8$O$_3$S: C, 49.09; H. 4.32; N, 5.45; Found: C, 49.10; H, 4.31; N, 5.35; [α]$^{25}$D=+30° (c=0.45, MeOH).

EXAMPLE 22

5-[(S)-2-dimethylamino-3-phenyl-1-propyloxy]-2-chloro-3-bromo pyridine p-toluenesulfonic acid 22 was synthesized as follows.

First, 5-[(S)-2-dimethylamino-3-phenyl-1-propyloxy]-2-chloro-3-bromo pyridine 22A was made as follows.

A solution of the product 21C (242 mg, 0.548 nunol) in a mixture of formaldehyde (37 wt. % in water, 7 mL) and formic acid (4 mL) was stirred at 65° C. overnight. The excess reagents were removed under reduced pressure at 45° C. Aqueous NaOH solution (1N) was added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 95/5 CH$_2$Cl$_2$/MeOH to provide 22A as a light yellow oil (84%, 170 mg). MS (CI/NH$_3$) m/e 369 (M+H)$^+$.

Then 5-[(S)-2-dimethylamino-3-phenyl-1-propyloxy]-2-chloro-3-bromo pyridine p-toluenesulfonic acid 22B was prepared as follows.

A solution of the product 22A (170 mg, 0.459 mmol) in ethyl acetate (1 mL) at room temperature was treated with p-toluenesulfonic acid monohydrate (96 mg, 0.505 mmol) and stirred for 5 minutes. Then ethyl ether (30 mL) was added and stirred for an additional 5 minutes. The ether was decanted and the procedure was repeated. The residue was then dried under vacuum to provide 22 as a white hygroscopic solid. mp 45–47° C.; MS (ESI$^+$) m/e 369 (M+H)$^+$; $^1$H NMR (D$_2$O, 300 MHz) δ: 2.39 (s, 3H), 3.06 (s, 6H), 3.13 (m, 1H), 3.37 (dd, J=5, 14 Hz, 1H), 4.02 (m, 1H), 4.18 (dd, J=6, 12 Hz, 1H), 4.30 (dd, J=3, 12 Hz, 1H), 7.30–7.43 (m, 7H), 7.68(d, J=8 Hz, 2H), 7.71 (d, J=3 Hz, 1H), 8.01 (d, J=3 Hz, 1H); Analysis calculated for C$_{16}$H$_{18}$N$_2$BrClO.1.15C$_7$H$_8$O$_3$S.0.60H$_2$O: C, 49.93; H, 4.95; N, 4.84; Found: C, 49.82; H, 4.88; N, 4.72; [α]$^{25}$D=+58° (c=3.0, MeOH).

EXAMPLE 23

5-[(S)-2-amino-3-phenyl-1-propyloxy]-2-chloro-3-(4-vinylpyridinyl)pyridine di-p-toluenesulfonic acid 23 was synthesized as follows.

First, 5-[(S)-2-N-BOC-amino-3-phenyl 1-propyloxy]-2-chloro-3-(4-vinylpyridinyl)pyridine 23A was prepared as follows.

A solution of the product 21A (670 mg, 1.52 mmol), 4-vinyl pyridine (0.25 mL, 2.28 mmol), palladium (TI) acetate (34 mg, 0.152 mmol), tri-o-tolylphosphine (92 mg, 0.304 mmol), and triethylamine (0.76 mL, 5.47 mmol) in acetonitrile (20 mL) was refluxed at 100° C. overnight. The reaction mixture was diluted with ethyl acetate, washed with saturated sodium carbonate, brine, dried (MgSO$_4$), filtered and concentrated. The residue was flash chromatographed with 30% ethyl acetate/hexane to provide 23A as a light yellow solid (80%, 565 mg); MS (CI/NH$_3$) m/e 466 (M+H)$^+$.

5-[(S)-2-amino-3-phenyl-1-propyloxy]-2-chloro-3-(4-vinylpyridinyl)pyridine di-p-toluenesulfonic acid 23 was then prepared as follows.

A solution of the product 23A (151 mg, 0.325 mmol) in ethyl acetate (1 mL) was treated with p-toluenesulfonic acid monohydrate (130 mg, 0.684 mmol) and stirred for 5 minutes. Next, ethyl ether (30 mL) was added and stirred for an additional 5 minutes. The ether was decanted and the procedure was repeated. The residue was then dried under vacuum to provide 23 as a light yellow solid. mp 229–231° C.; MS (ESI$^+$) m/e 366 (M+H)$^+$; $^1$H NMR (D$_2$O, 400 MHz) δ: 2.35 (s, 6H), 3.18 (d, J=8 Hz, 2H), 4.03 (m, 1H), 4.20 (dd, J=6, 10 Hz, 1H), 4.35 (dd, J=3, 11 Hz, 1H), 7.23–7.46 (m, 9H), 7.64 (d, J=8 Hz, 4H), 7.76 (m, 2H), 8.06 (t, J=3 Hz, 4H), 8.65 (d, J=7 Hz, 2H); Analysis calculated for C$_{21}$H$_{20}$N$_3$ClO.2C$_7$H$_8$O$_3$S: C, 59.19; H, 5.11; N, 5.92; Found: C, 58.98; H, 4.96; N, 5.85; [α]$^{25}$D=+18° (c=0.80, MeOH).

EXAMPLE 24

5-[(S)-2-N-dimethyl-amino-3-phenyl-1-propyloxy]-2-chloro-3-(4-vinylpyridinyl)pyridine di-p-toluenesulfonic acid 24 was synthesized according to the following procedure.

First, 5-[(S)-2-N-dimethyl-amino-3-phenyl-1-propyloxy]-2-chloro-3-(4-vinylpyridinyl)pyridine 24A was prepared as follows.

A solution of the product 23A (400 mg, 0.860 mmol) in a mixture of formaldehyde (37 wt. % in water, 14 mL) and formic acid (8 mL) was stirred at 65° C. overnight. Then the excess reagents were removed under reduced pressure at 45° C. Aqueous NaOH solution (1N) was added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 95/5 CH$_2$Cl$_2$/MeOH to provide 24A as a light yellow oil (67%, 226 mg). MS (CI/NH$_3$) m/e 394 (M+H)$^+$.

Then 5-[(S)-2-N-dimethyl-amino-3-phenyl-1-propyloxy]-2-chloro-3-(4-vinylpyridinyl)pyridine di-p-toluenesulfonic acid 24 was made as follows.

A solution of the product 24A (220 mg, 0.559 mmol) in ethyl acetate (1 mL) at room temperature was treated with p-toluenesulfonic acid monohydrate (224 mg, 1.18 mmol) and stirred for 5 minutes. Then ethyl ether (30 mL) was added and stirred for an additional 5 minutes. The ether was decanted and the io procedure was repeated. The residue was then dried under vacuum to provide 24 as a light yellow solid. mp 81–83° C.; MS (ESI$^+$) m/e 394 (M+H)$^+$; $^1$H NMR (D$_2$O, 300 MHz) δ: 2.31 (s, 6H), 3.07 (s, 3H), 3.10 (s, 3H), 3.35 (m, 2H), 4.02–4.37 (m, 3H), 7.12–7.40 (m, 10H), 7.6 (d, J=8 Hz, 4H), 7.70 (m, 1H), 7.98 (s, 1H), 8.04–8.06 (m, 3H), 8.64 (d, J=6 Hz, 2H); Analysis calculated for C$_{23}$H$_{24}$N$_3$ClO.2.20C$_7$H$_8$O$_3$S.1.45H$_2$O: C, 57.73; H, 5.61; N, 5.26; Found:C, 57.42; H, 5.64; N, 4.95; [α]$^{25}$D=+42° (c=1.8, MeOH).

EXAMPLE 25

5-[(S)-2-methylamino-3-phenyl-1-propyloxy]-2-chloro-3-(4-vinylpyridinyl)pyridine di-p-toluenesulfonic acid 25 was synthesized according to the following procedure.

First, 5-[(S)-2-N-BOC-methylamino-3-phenyl-1-propyloxy]-2-chloro-3-bromo pyridine 25A was made as follows.

A solution of the product 21C (670 mg, 1.52 mmol) in THF (20 mL) at room temperature was treated with sodium hydride (60% dispersion in mineral oil, 109 mg, 4.55 mmol) and stirred for 20 minutes. Iodomethane (0.76 mL, 12.2 mmol) was then added and stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with CH$_2$Cl$_2$. The combined CH$_2$Cl$_2$ extract was washed with brine, dried (MgSO$_4$), filtered and concentrated. The residue was flash chromatographed on silica gel with 10% ethyl acetate/hexane to provide a light yellow oil 25A (97%, 670 mg). MS (CUNH$_3$) m/e 455 (M+H)$^+$, 472 (M+NH$_4$)$^+$.

Next, 5-[(S)-2-N-BOC-methylamino-3-phenyl-1-propyloxy]-2-chloro-3-(4-vinylpyridinyl)pyridine 25B was prepared as follows.

A solution of the product 25A (560 mg, 1.23 mmol), 4-vinyl pyridine (0.20 mL, 1.84 runol), palladium (II) acetate (27 mg, 0.12 mmol), tri-o-tolylphosphine (75 mg, 0.24 mmol), and triethylamine (0.62 mL, 4.43 mmol) in acetonitrile (20 mL) was refluxed at 100° C. overnight. Next, the reaction mixture was diluted with ethyl acetate, washed with saturated sodium carbonate, brine, dried (MgSO$_4$), filtered and concentrated. The residue was flash chromatographed with 30% ethyl acetate/hexane to provide 25B (24%, 141 mg); MS (CI/NH$_3$) m/e 480 (M+H)$^+$.

Next, 5-[(S)-2-methylamino-3-phenyl-1-propyloxy]-2-chloro-3-(4-vinylpyridinyl)pyridine di-p-toluenesulfonic acid 25 was made as follows.

A solution of the product from 25B (138 mg, 0.288 mmol) in ethyl acetate (1 mL) was treated with p-toluenesulfonic acid monohydrate (115 mg, 0.605 ninol) and stirred for 5 minutes. Next, ethyl ether (30 mL) was added and stirred for an additional 5 minutes. The ether was decanted and the procedure was repeated. The residue was then dried under vacuum to 25 as a light yellow solid. mp 81–83° C.; MS (ESI$^+$) m/e 380 (M+H)$^+$; $^1$HNMR (D$_2$O, 400 MHz) δ: 2.32 (s, 6H), 2.87 (s, 3H), 3.07–3.13 (m, 2H), 3.91 (m, 1H), 4.16 (dd, J=4, 11 Hz, 1H), 4.36 (d, J=11 Hz, 1H), 7.22–7.42 (m, 10H), 7.60–7.78 (m, 5H), 8.04 (d, J=7 Hz, 4H), 8.64 (d, J=7 Hz, 2H); Analysis calculated for C$_{22}$H$_{22}$N$_3$ClO.2.1C$_7$H$_8$O$_3$S.1.3H$_2$O: C, 57.63; H, 5.46; N, 5.49; Found: C, 57.61; H, 5.63; N, 5.32; [α]$^{25}$D=+28° (c=1.4, MeOH).

EXAMPLE 26

5-[(S)-2-amino-1-propyloxy]-2-chloro pyridine p-toluenesulfonic acid 26 was synthesized according to the following procedure.

First, 2-[(S)-N-BOC]-propanol 26A was prepared as follows. A solution of N-(tert-butoxycarbonyl-D-alanine (25 g, 132 mmol) in anhydrous THF (150 mL) at 0° C. was treated with borane (1M solution in THF, 200 mL) over a period of 45 minutes. The ice bath was then removed and the reaction mixture was stirred at room temperature for 3 hours. Saturated NaHCO$_3$ solution was added slowly to quench the reaction. The resultant solution was then stirred overnight. Next, solvent was removed under reduced pressure. The remaining water phase was extracted 4× with ethyl ether. The combined ether extract was washed with brine, dried (MgSO$_4$), filtered, and concentrated. The residue was flash chromatographed on silica gel with 30% ethyl acetate/hexane to provide a white solid 26A (62%, 14.3 g). MS (CI/NH$_3$) m/e 176 (M+H)$^+$, 193 (M+NH$_4$)$^+$; $^1$H NMR (CDCl$_3$, 300 MHz) δ: 1.16 (d, J=6 Hz, 3H), 1.46 (s, 9H), 3.59 (bs, 1H), 3.70 (bs, 1H), 3.80 (bs, 1H).

Then 2-[(S)-N-BOC]-propanol tosylate 26B was made as follows.

A solution of the product from Example 26A (14.2 g, 81.1 mmol) in CH$_2$Cl$_2$ (300 mL) at room temperature was treated with triethylamine (18.0 mL, 130 numol) and p-toluenesulfonyl chloride (19.3 g, 101 mmol), and then stirred overnight. The reaction mixture was diluted with CH$_2$Cl$_2$ to 300 mL, washed with water, 5% NaHCO$_3$, and brine. The residue was then dried (MgSO$_4$), filtered and concentrated. The residue was flash chromatographed on silica gel with 30% ethyl acetate/hexane to provide a white solid 26B (72%, 19.3 g). MS (CI/NH$_3$) m/e 347 (M+NH$_4$)$^+$; $^1$H NMR (CDCl$_3$, 300 MHz) δ: 1.16 (d, J=7 Hz, 3H), 1.41 (s, 9H), 2.45 (s, 3H), 3.85–4.07 (m, 3H), 4.57 (bs, 1H), 7.35 (d, J=8 Hz, 2H), 7.79 (d, J=8 Hz, 2H).

Next, 5-[(S)-2-N-BOC-amino-1-propyloxy]-2-chloro pyridine 26C was prepared as follows.

A solution of the product 26B (700 mg, 2.13 mrnol) in DMF (10 mL) was treated with potassium hydroxide (298 mg, 5.32 mmol) and 2-chloro-5-hydroxyl pyridine (344 mg, 2.66 mmol), and then stirred at 85° C. overnight. Next, DMF was removed under reduced pressure at 60° C. The residue was dissolved in a mixture of H$_2$O and CH$_2$Cl$_2$. The organic layer was washed with water, and brine; then dried (MgSO$_4$), filtered and concentrated. The residue was flash chromatographed on silica gel with 20% ethyl acetate/hexane to provide a light yellow solid 26C (23%, 143 mg). MS (CI/NH$_3$) m/e 287 (M+H)$^+$, 304 (M+NH$_4$)$^+$; $^1$H NMR (CDCl$_3$, 300 MHz) δ: 1.30 (d, J=7 Hz, 3H), 1.45 (s, 9H), 3.93–4.08 (m, 3H), 4.68 (bs, 1H), 7.23 (d, J=2 Hz, 2H), 8.07 (m, 1H).

Then 5-[(S)-2-amino-1-propyloxy]-2-chloro pyridine 26D was prepared as follows.

A solution of the product 26C (730 mg, 2.55 mmol) in CH$_2$Cl$_2$ (10 mL) was treated with trifluoroacetic acid (4 mL) and stirred at room temperature overnight. Then solvent and excess reagent were removed under reduced pressure. The residue was dissolved in saturated sodium carbonate solution and extracted 3× with CH$_2$Cl$_2$; and the combined CH$_2$Cl$_2$ extract was dried (MgSO$_4$), filtered and concentrated. The residue was flash chromatographed on silica gel with 95/5/0.5 CH$_2$Cl$_2$/CH$_3$OH/NH$_4$OH to provide a light yellow oil 26D (72%, 340 mg). MS (CI/NH$_3$) m/e 187 (M+H)$^+$.

5-[(S)-2-amino-1-propyloxy]-2-chloro pyridine p-toluenesulfonic acid 26 was then made as follows.

A solution of the product 26D (80 mg, 0.429 mmol) in ethyl acetate (1 mL) was treated with p-toluenesulfonic acid monohydrate (86 mg, 0.452 mmol) and stirred for 5 minutes. Then ethyl ether (30 ml) was added and stirred for an additional 5 minutes. The ether was decanted and the procedure was repeated. The residue was then dried under vacuum to provide 26 as a white solid. mp 177–179° C.; MS (CI/NH$_3$) m/e 187 (M+H)$^+$; $^1$H NMR (D$_2$O, 300 MHz) δ: 1.24 (d, J=7 Hz, 3H), 2.21 (s, 3H), 3.66 (m, 1H), 3.94 (dd, J=7, 10 Hz, 1H), 4.14 (dd, J=4, 11 Hz, 1H), 7.18 (d, J=8 Hz, 2H), 7.25–7.35 (m, 2H), 7.50 (d, J=8 Hz, 2H), 7.91 (d, J=3 Hz, 1H). Analysis calculated for C$_8$H$_{11}$N$_2$ClO.C$_7$H$_8$O$_3$S: C, 50.20; H, 5.33; N, 7.80; Found: C, 50.01; H, 5.23; N, 7.49; [α]$^{25}$D=−2.8° (c=0.82, MeOH).

EXAMPLE 27

5-[(S)-2-dimethylamino-1-propyloxy]-2-chloro pyridine p-toluenesulfonic acid 27 was synthesized according to the following procedure.

First, 5-[(S)-2-dimethylamino-1-propyloxy]-2-chloro pyridine 27A was made as follows.

A solution of the product 26D (260 mg, 1.39 mmol) in a mixture of formaldehyde (37 wt. % in water, 8 mL) and formic acid (4.2 mL) was stirred at 65° C. overnight. The excess reagents were removed under reduced pressure at 45° C. Aqueous NaOH solution (1N) was added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 90/10/1 CH$_2$Cl$_2$/MeOH/NH$_4$OH to provide 27A (46%, 155 mg). MS (CI/NH$_3$) m/e 215 (M+H)$^+$.

Next, 5-[(S)-2-dimethylamino-1-propyloxy]-2-chloropyridine p-toluenesulfonic acid 27 was made as follows.

A solution of the product 27A (150 mg, 0.701 mmol) in ethyl acetate (1 mL) at room temperature was treated with p-toluenesulfonic acid monohydrate (140 mg, 0.736 mmol) and stirred for 5 minutes. Next, ethyl ether (30 mL) was added and stirred for an additional 5 minutes. The ether was decanted and the procedure was repeated. The residue was then dried under vacuum to provide 27 as a white hygroscopic solid. mp 80–82° C.; MS (CI/NH$_3$) m/e 215 (M+H)$^+$; $^1$H NMR (D$_2$O, 300 MHz) δ: 1.42 (d, J=7 Hz, 3H), 2.39 (s, 3H), 2.91 (d, J=1 Hz, 6H), 3.91 (m, 1H), 4.28 (dd, J=6, 11 Hz, 1H), 4.40 (dd, J=4, 12 Hz, 1H), 7.37 (d, J=8 Hz, 2H), 7.44–7.53 (m, 2H), 7.69 (d, J=8 Hz, 2H), 8.11 (d, J=3 Hz, 1H); Analysis calculated for C$_{10}$H$_{15}$N$_2$ClO.1.03C$_7$H$_8$O$_3$S.0.08H$_2$O: C, 52.53; H, 5.99; N, 7.11; Found: C, 52.93; H, 5.88; N, 6.71; [α]$^{25}$D=−3.3° (c=1.3, MeOH).

EXAMPLE 28

5-[(R)-2-methylamino-1-propyloxy]-2-chloropyridine p-toluenesulfonic acid 28 was synthesized in the following manner.

First, 5-[(R)-2-N-BOC-methylamino-1-propyloxy]-2-chloro pyridine 28A was prepared as follows.

A solution of the product 26C (180 mg, 0.628 mmol) in THF (8 mL) at room temperature was treated with sodium hydride (60% dispersion in mineral oil, 75 mg, 1.88 mmol) and stirred for 20 minutes. Iodomethane (0.31 mL, 5.02 mmol) was then added and stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with CH$_2$Cl$_2$. The combined CH$_2$Cl$_2$ extract was washed with brine, dried (MgSO$_4$), filtered and concentrated. The residue was flash chromatographed on silica gel with 15% ethyl acetate/hexane to provide a light yellow oil 28A (80%, 160 mg). MS (CI/NH$_3$) m/e 301 (M+H)$^+$, 318 (M+NH$_4$)$^+$; $^1$H NMR (CDCl$_3$, 300 MHz) δ: 1.25 (d, J=7 Hz, 3H), 1.46 (s, 9H), 2.80 (s, 3H), 3.89–4.03 (m, 2H), 4.56 (bs, 1H), 7.16–7.26 (m, 2H), 8.05 (d, J=3 Hz, 1H).

Then 5-[(R)-2-methylamino-1-propyloxy]-2-chloro pyridine p-toluenesulfonic acid 28 was prepared as follows.

A solution of the product from Example 28A (147 mg, 0.489 mmol) in CH$_2$Cl$_2$ (8 mL) was treated with p-toluenesulfonic acid monohydrate (102 mg, 0.536 mmol) and refluxed at 60° C. overnight. Next, solvent was removed by bubbling nitrogen into the solution. Ethyl ether (30 mL) was added and stirred for 5 minutes. The ether was decanted and the procedure was repeated. The residue was then dried under vacuum to provide 28 as a light yellow solid. mp 65–67° C.; MS (CI/NH$_3$) m/e 201 (M+H)$^+$; $^1$H NMR (D$_2$O, 500 MHz) δ: 1.45 (d, J=7 Hz, 3H), 2.39 (s, 3H), 2.78 (s, 3H), 3.74 (m, 1H), 4.20 (dd, J=7, 11 Hz, 1H), 4.37 (dd, J=3, 10 Hz, 1H), 7.36 (d, J=8 Hz, 2H), 7.44 (d, J=9 Hz, 1H), 7.50 (dd, J=3, 9 Hz, 1H), 7.69 (d, J=8, 2H), 8.09 (d, J=3 Hz, 1H); Analysis calculated for C$_9$H$_{13}$N$_2$ClO.1.2C$_7$H$_8$O$_3$S.0.2H$_2$O: C, 50.86; H, 5.64; N, 6.82 Found: C, 50.79; H, 5.37; N, 6.67; [α]$^{25}$D=–7.4° (c=1.4, MeOH).

EXAMPLE 29

5-[(R)-2-amino-1-propyloxy]-2-fluoro pyridine p-toluenesulfonic acid 29 was synthesized in the following manner.

First, 5-[(R)-2-N-BOC-amino-1-propyloxy]-2-fluoro pyridine 29A was prepared as follows.

A solution of the product 26B (605 mg, 1.84 mmol) in DMF (10 mL) was treated with potassium hydroxide (258 mg, 4.60 mmol) and 2-fluoro-5-hydroxyl pyridine (260 mg, 2.30 mmol), and stirred at 85° C. overnight. Then DMF was removed under reduced pressure at 60° C. The residue was dissolved in a mixture of H$_2$O and CH$_2$Cl$_2$. The organic layer was washed with water, and brine. It was then dried (MgSO$_4$), filtered and concentrated. The residue was flash chromatographed on silica gel with 20% ethyl acetate/hexane to provide a light yellow oil 26A (67%, 330 mg). MS (CI/NH$_3$) m/e 271 (M+H)$^+$, 288 (M+NH$_4$)$^+$; $^1$H NMR (CDCl$_3$, 300 MHz) δ: 1.31 (d, J=7 Hz, 3H), 1.46 (s, 9H), 3.97–4.23 (m, 3H), 4.68 (bs, 1H), 6.76 (m, 1H), 7.35 (m, 1H), 7.86 (s, 1H).

Next, 5-[(R)-2-amino-1-propyloxy]-2-fluoro pyridine 29B was prepared as follows.

A solution of the product from Example 29A (366 mg, 1.36 mmol) in CH$_2$Cl$_2$ (4 mL) was treated with trifluoroacetic acid (2 mL) and stirred at room temperature overnight. Next, solvent and excess reagent were removed under reduced pressure. The residue was dissolved in saturated sodium carbonate solution and extracted 3× with CH$_2$Cl$_2$ The combined CH$_2$Cl$_2$ extract was dried (MgSO$_4$), filtered and concentrated. The residue was flash chromatographed on silica gel with 95/5/0.5 CH$_2$Cl$_2$/CH$_3$OH/NH$_4$OH to provide a yellow oil 29B (72%, 166 mg). MS (CP/NH$_3$) m/e 171 (M+H)$^+$, 188 (M+NH$_4$)$^+$.

Then 5-[(R)-2-amino-1-propyloxy]-2-fluoro pyridine p-toluenesulfonic acid 29 was prepared as follows.

A solution of the product 29B (160 mg, 0.976 mmol) in ethyl acetate (1 mL) was treated with p-toluenesulfonic acid monohydrate (195 mg, 1.03 mmol) and stirred for 5 minutes. Then ethyl ether (30 ml) was added and stirred for an additional 5 minutes. The ether was decanted and the procedure was repeated. The residue was then dried under vacuum to provide 29 as a white solid. mp 159–161° C.; MS (CI/NH$_3$) m/e 171 (M+H)$^+$, 188 (M+NH$_4$)$^+$; $^1$H NMR (D$_2$O, 300 MHz) δ: 1.43 (d, J=7 Hz, 3H), 2.41 (s, 3H), 3.84 (m, 1H), 4.13 (dd, J=7, 10 Hz, 1H), 4.32 (dd, J=3, 10 Hz, 1H), 7.09 (dd, J=3, 9 Hz, 1H), 7.38 (d, J=8 Hz, 2H), 7.64 (m, 1H), 7.70 (d, J=8 Hz, 2H), 7.89 (m, 1H), Analysis calculated for C$_8$H$_{11}$N$_2$FO.1.1C$_7$H$_8$O$_3$S: C, 52.44; H, 5.55; N, 7.79; Found: C, 52.09; H, 5.48; N, 8.09; [α]$^{25}$D=–3.9° (c=0.73, MeOH).

EXAMPLE 30

5-[(R)-2-dimethylamino-1-propyloxy]-2-fluoro pyridine p-toluenesulfonic acid 30 was synthesized according to the following procedure.

First, 5-[(R)-2-dimethylamino-1-propyloxy]-2-fluoro pyridine 30A was synthesized as follows.

A solution of the product 29A (108 mg, 0.635 mmol) in the mixture of formaldehyde (37 wt. % in water, 4 mL) and formic acid (2.6 mL) was stirred at 65° C. overnight. The excess reagents were removed under reduced pressure at 45° C. Aqueous NaOH solution (1N) was added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 95/5/0.5 CH$_2$Cl$_2$/MeOH/NH$_4$OH to provide a light yellow oil 30A (53%, 67 mg). MS (CI/NH$_3$) m/e 199 (M+H)$^+$.

5-[(R)-2-dimethylamino-1-propyloxy]-2-fluoro pyridine p-toluenesulfonic acid 30 was then prepared as follows.

A solution of the product 30A (60 mg, 0.303 mmol) in ethyl acetate (1 mL) was treated with p-toluenesulfonic acid monohydrate (60 mg, 0.318 mmol) and stirred for 5 minutes. Then ethyl ether (30 mL) was added and stirred for an additional 5 minutes. The ether was decanted and the procedure was repeated. The residue was then dried under vacuum to provide 30 as a white solid. mp 107–109° C.; MS (APCI$^+$) m/e 199 (M+H)$^+$; $^1$H NMR (D$_2$O, 500 MHz) δ: 1.43 (d, J=7 Hz, 3H), 2.40 (s, 3H), 2.92 (s, 6H), 3.90 (m, 1H), 4.27 (dd, J=8, 11 Hz, 1H), 4.40 (dd, J=4, 12 Hz, 1H), 7.10 (m, 1H), 7.36–7.39 (m, 2H), 7.65 (m, 1H), 7.68–7.72 (m, 2H), 7.90 (dd, J=1, 3 Hz, 1H); Analysis calculated for C$_{10}$H$_{15}$N$_2$FO.C$_7$H$_8$O$_3$S: C, 55.12; H, 6.25; N, 7.56; Found: C, 54.88; H, 6.17; N, 7.29; [α]$^{25}$D=–10° (c=0.30, MeOH).

EXAMPLE 31

5-[(R)-2-methylamino-1-propyloxy]-2-fluoro pyridine p-toluenesulfonic acid 31 was synthesized according to the following procedure.

First, 5-[(R)-2-N-BOC-methylamino-1-propyloxy]-2-fluoro-pyridine 31A was made as follows.

A solution of the product 29A (320 mg, 1.19 mmol) in THF (15 mL) was treated with sodium hydride (60% dispersion in mineral oil, 142 mg, 3.56 mmol) and stirred for 20 minutes. Then, iodomethane (0.59 mL, 11.3 mmol) was added and stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with $CH_2Cl_2$. The combined $CH_2Cl_2$ extract was washed with brine, dried ($MgSO_4$), filtered and concentrated. The residue was flash chromatographed on silica gel with 15% ethyl acetate/hexane to provide a clear oil 31A (66%, 230 mg). MS ($CI/NH_3$) m/e 285 $(M+H)^+$, 302 $(M+NH_4)^+$; $^1H$ NMR ($CDCl_3$, 300 MHz) δ: 1.25 (d, J=7 Hz, 3H), 1.46 (s, 9H), 2.80 (s, 3H), 3.90–4.03 (m, 2H), 4.53 (br, 1H), 6.85 (dd, J=3, 9 Hz, 1H), 7.31 (m, 1H), 7.81 (s, 1H).

Then 5-[(R)-2-methylamino-1-propyloxy]-2-fluoro pyridine p-toluenesulfonic acid 31 was prepared as follows.

A solution of the product 31A (223 mg, 0.785 mmol) in $CH_2Cl_2$ (8 mL) was treated with p-toluenesulfonic acid monohydrate (164 mg, 0.863 mmol) and refluxed at 60° C. overnight. Next solvent was removed by bubbling nitrogen into the solution. Ethyl ether (30 mL) was added and stirred for 5 minutes. The ether was decanted and the procedure was repeated. The residue was then dried under vacuum to provide 31 as a white solid. mp 87–89° C.; MS ($CI/NH_3$) m/e 185 $(M+H)^+$, 202 $(M+NH_4)^+$; $^1H$ NMR ($D_2O$, 500 MHz) δ: 1.45 (d, J=7 Hz, 3H), 2.39 (s, 3H), 2.78 (s, 3H), 3.73 (m, 1H), 4.18 (dd, J=6, 10 Hz, 1H), 4.35 (dd, J=3, 10 Hz, 1H), 7.08 (dd, J=3, 9 Hz, 1H), 7.35 (d, J=8 Hz, 2H), 7.61 (m, 1H), 7.68 (d, J=8 Hz, 2H), 7.86 (d, J=2 Hz, 1H); Analysis calculated for $C_9H_{13}N_2FO.C_7H_8O_3S$: C, 53.92; H, 5.94; N, 7.86; Found: C, 53.69; H, 5.96; N, 7.72; $[α]^{25}D=-8.6°$ (c=1.0, MeOH).

EXAMPLE 32

5-[(R)-2-amino-1-propyloxy]-2-chloro-3-bromo pyridine p-toluenesulfonic acid 32 was synthesized according to the following procedure.

First, 5-[(R)-2-N-BOC-amino-1-propyloxy]-2-chloro-3-bromo pyridine 32A was prepared as follows.

A solution of the product 26B (3.14 g, 9.54 mmol) in DMF (40 mL) was treated with potassium hydroxide (1.33 g, 23.8 mmol) and 2-chloro-3-bromo-5-hydroxyl pyridine (2.49 g, 11.9 mmol) and then stirred at 85° C. overnight. DMF was removed under reduced pressure at 60° C. The residue was dissolved in a mixture of $H_2O$ and $CH_2Cl_2$. The organic layer was washed 2× with water, and 1× with brine, dried ($MgSO_4$), filtered, and concentrated. The residue was flash chromatographed on silica gel with 15% ethyl acetate/hexane to provide a white solid 32A (51%, 1.77 g). MS ($CI/NH_3$) m/e 365 $(M+H)^+$, 382 $(M+NH_4)^+$.

5-[(R)-2-amino-1-propyloxy]-2-chloro-3-bromo pyridine p-toluenesulfonic acid 32 was then prepared as follows.

A solution of the product 32A (103 mg, 0.282 mmol) in $CH_2Cl_2$ (8 mL) was treated with p-toluenesulfonic acid monohydrate (59 mg, 0.310 mmol) and refluxed at 60° C. overnight. Then solvent was removed by bubbling nitrogen into the solution. Ethyl ether (30 mL) was added and stirred for 5 minutes. The ether was decanted and the procedure was repeated. The residue was then dried under vacuum to provide 32 as a white solid. mp 159–161° C.; MS ($CI/NH_3$) m/e 265 $(M+H)^+$, 282 $(M+NH_4)^+$; $^1H$ NMR ($D_2O$, 500 MHz) δ: 1.44 (d, J=7 Hz, 3H), 2.40 (s, 3H), 3.85 (m, 1H), 4.14 (dd, J=7, 10 Hz, 1H), 4.32 (dd, J=3, 11 Hz, 1H), 7.36 (d, J=8 Hz, 2H), 7.69 (d, J=8 Hz, 2H), 7.85 (d, J=3 Hz, 1H), 8.09 (d, J=3 Hz, 1H); Analysis calculated for $C_8H_{10}N_2BrClO.C_7H_8O_3S.0.4H_2O$: C, 41.49; H, 4.26; N, 6.30; Found: C, 40.22; H, 3.90; N, 6.19; $[α]^{25}D=-6.6°$ (c=2.2, MeOH).

EXAMPLE 33

5-[(R)-2-dimethylamino-1-propyloxy]-2-chloro-3-bromo pyridine p-toluenesulfonic acid 33 was synthesized according to the following procedure.

First, 5-[(R)-2-dimethylamino-1-propyloxy]-2-chloro-3-bromo pyridine 33A was made as follows.

A solution of the product 32A (218 mg, 0.596 mmol) in a mixture of formaldehyde (37 wt. % in water, 7 mL) and formic acid (4 mL) was stirred at 65° C. overnight. The excess reagents were removed under reduced pressure at 45° C. Aqueous NaOH solution (1N) was added to the residue and extracted 3× with $CH_2Cl_2$. The combined $CH_2Cl_2$ extract was washed with brine, dried ($MgSO_4$), filtered, and concentrated. The residue was flash chromatographed on silica gel with 95/5/0.5 $CH_2Cl_2/MeOH/NH_4OH$ to provide 33A as a light yellow oil (58%, 102 mg). MS ($CI/NH_3$) m/e 293 $(M+H)^+$.

Then 5-[(R)-2-dimethylamino-1-propyloxy]-2-chloro-3-bromo pyridine p-toluenesulfonic acid 33 was prepared as follows.

A solution of the product 33A (102 mg, 0.349 mmol) in ethyl acetate (1 mL) at room temperature was treated with p-toluenesulfonic acid monohydrate (73 mg, 0.384 mmol) and stirred for 5 minutes. Then diethyl ether (30 mL) was added and stirred for an additional 5 minutes. The ether was decanted and the procedure was repeated. The residue was then dried under vacuum to provide 33 as a white hygroscopic solid. MS ($CI/NH_3$) m/e 293 $(M+H)^+$; $^1H$ NMR ($D_2O$, 500 MHz) δ: 1.43 (d, J=7 Hz, 3H), 2.38 (s, 3H), 2.91 (d, J=37 Hz, 6H), 3.90 (m, 1H), 4.26 (dd, J=8, 12 Hz, 1H), 4.38 (dd, J=4, 12 Hz, 1H), 7.34 (d, J=8 Hz, 2H), 7.67 (d, J=8 Hz, 2H), 7.84 (d, J=3 Hz, 1H), 8.08 (d, J=3 Hz, 1H); Analysis calculated for $C_{10}H_{14}N_2BrClO.1.1C_7H_8O_3S.0.2H_2O$: C, 43.69; H, 4.81; N, 5.76; Found: C, 43.66; H, 4.62; N, 5.47; $[α]^{25}D=-0.87°$ (c=0.69, MeOH).

EXAMPLE 34

5-[(R)-2-methylamino-1-propyloxy]-2-chloro-3-bromo pyridine p-toluenesulfonic acid 34 was synthesized according to the following procedure.

First, 5-[(R)-2-N-BOC-methylamino-1-propyloxy]-2-chloro-3-bromo pyridine 34A was synthesized as follows.

A solution of the product 32A (225 mg, 0.615 mmol) in THF (10 mL) at room temperature was treated with sodium hydride (60% dispersion in mineral oil, 74 mg, 1.85 mmol) and stirred for 20 minutes. Next, iodomethane (0.31 mL, 4.92 mmol) was added and stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with $CH_2Cl_2$. The combined $CH_2Cl_2$ extract was washed with brine, dried ($MgSO_4$), filtered and concentrated. The residue was flash chromatographed on silica gel with 10% ethyl acetate/hexane to provide a light yellow oil 34A (83%, 195 mg). MS ($CI/NH_3$) m/e 379 $(M+H)^+$, 396 $(M+NH_4)^+$; $^1H$ NMR ($CDCl_3$, 300 MHz) δ: 1.25 (d, J=6 Hz, 3H), 1.46 (s, 9H), 2.81 (s, 3H), 3.89–4.06 (m, 2H), 4.50 (bs, 1H), 7.49 (d, J=2 Hz, 1H), 8.03 (d, J=2, 1H).

Then 5-[(R)-2-methylamino-1-propyloxy]-2-chloro-3-bromo pyridine p-toluenesulfonic acid 34 was prepared as follows.

A solution of the product 34A (194 mg, 0.511 mmol) in $CH_2Cl_2$ (8 mL) was treated with p-toluenesulfonic acid monohydrate (107 mg, 0.563 mmol) and refluxed at 60° C. overnight. Then solvent was removed by bubbling nitrogen into the solution. Ethyl ether (30 mL) was added and stirred for 5 minutes. The ether was decanted and the procedure was repeated. The residue was then dried under vacuum to provide 34 as a hygroscopic white solid. mp 42–44° C.; MS ($CI/NH_3$) m/e 279 $(M+H)^+$, 296 $(M+NH_4)^+$; $^1H$ NMR ($D_2O$, 500 MHz) δ: 1.44 (d, J=7 Hz, 3H), 2.38 (s, 3H), 2.78 (s, 3H), 3.73 (m, 1H), 4.18 (dd, J=6, 10 Hz, 1H), 4.36 (dd, J=3, 10 Hz, 1H), 7.34 (d, J=8 Hz, 2H), 7.67 (d, J=8 Hz, 2H), 7.82 (d, J=3 Hz, 1H), 8.07 (d, J=3 Hz, 1H); Analysis calculated for $C_9H_{12}N_2BrClO.C_7H_8O_3S$: C, 42.54; H, 4.46; N, 6.20; Found: C, 42.61; H, 4.67; N, 5.98, $[α]^{25}D=-5.8°$ (c=0.65, MeOH).

EXAMPLE 35

5-[(R)-2-amino-l1-propyloxy]-2-chloro-3-methyl pyridine p-toluenesulfonic acid 35 was synthesized according to the following procedure.

First, 5-[(R)-2-N-BOC-amino-l1-propyloxy]-2-chloro-3-methyl pyridine 35A was prepared as follows.

A solution of the product 26B (1.32 g, 4.01 mmol) in DMF (20 mL) was treated with potassium hydroxide (561 mg, 10.0 mmol) and 2-chloro-3-methyl-5-hydroxyl pyridine (720 mg, 5.02 inmol), and then stirred at 85° C. overnight. DMF was removed under reduced pressure at 60° C. The residue was dissolved in a mixture of $H_2O$ and $CH_2Cl_2$. The organic layer was washed with water, and brine; then dried ($MgSO_4$), filtered and concentrated. The residue was flash chromatographed on silica gel with 20% ethyl acetate/hexane to provide a white solid 35A (35%, 424 mg). MS ($CI/NH_3$) m/e 301 $(M+H)^+$.

Then 5-[(R)-2-amino-1-propyloxy]-2-chloro-3-methyl pyridine p-toluenesulfonic acid 35 was prepared as follows.

A solution of the product 35A (76 mg, 0.253 mmol) in $CH_2Cl_2$ (8 mL) was treated with p-toluenesulfonic acid monohydrate (53 mg, 0.279 numol) and refluxed at 60° C. overnight. Next solvent was removed by bubbling nitrogen into the solution. Ethyl ether (30 mL) was added and stirred for 5 minutes. The ether was decanted and the procedure was repeated. The residue was then dried under vacuum to provide a white solid 35. mp 156–158° C.; MS ($CI/NH_3$) m/e 201 $(M+H)^+$; $^1H$ NMR ($D_2O$, 500 MHz) δ: 1.42 (d, J=7 Hz, 3H), 2.33 (s, 3H), 2.38 (s, 3H), 3.82 (m, 1H), 4.09 (dd, J=7, 12 Hz, 1H), 4.28 (dd, J=3, 10 Hz, 1H), 7.37(d, J=8 Hz, 2H), 7.40 (d, J=2 Hz, 1H), 7.67 (d, J=8 Hz, 2H), 7.92 (d, J=3 Hz, 1H); Analysis calculated for $C_9H_{13}N_2ClO.1.2C_7H_8O_3S.0.2H_2O$: C, 50.86; H, 5.64; N, 6.82; Found: C, 50.68; H, 5.53; N, 6.70; $[α]^{25}D=-4.4°$ (c=0.75, MeOH).

EXAMPLE 36

5-[(R)-2-dimethylamino-1-propyloxy]-2-chloro-3-methyl pyridine p-toluenesulfonic acid 36 was synthesized according to the following procedure.

First, 5-[(R)-2-dimethylamino-1-propyloxy]-2-chloro-3-methyl pyridine 36A was prepared as follows.

A solution of the product 35A (146 mg, 0.486 mmol) in a mixture of formaldehyde (37 wt. % in water, 7 mL) and formic acid (4 mL) was stirred at 65° C. overnight. The excess reagents were removed under reduced pressure at 45° C. Aqueous NaOH solution (1N) was added to the residue and extracted 3× with $CH_2Cl_2$. The combined $CH_2Cl_2$ extract was washed with brine, dried ($MgSO_4$), filtered, and concentrated. The residue was flash chromatographed on silica gel with 95/5/0.5 $CH_2Cl_2$/MeOH/$NH_4OH$ to provide 36A as a light yellow oil (54%, 60 mg). MS ($CI/NH_3$) m/e 229 $(M+H)^+$.

Then 5-[(R)-2-dimethylamino-1-propyloxy]-2-chloro-3-methyl pyridine p-toluenesulfonic acid 36 was prepared as follows.

A solution of the product 36A (60 mg, 0.263 mmol) in ethyl acetate (1 mL) at room temperature was treated with p-toluenesulfonic acid monohydrate (55 mg, 0.289 mmol) and stirred for 5 minutes. Next ethyl ether (30 mL) was added and stirred for an additional 5 minutes. The ether was decanted and the procedure was repeated. The residue was then dried under vacuum to provide 36 as a white solid. mp 87–89° C.; MS ($CI/NH_3$) m/e 229 $(M+H)^+$; $^1H$ NMR ($D_2O$, 300 MHz) δ: 1.43 (d, J=7 Hz, 3H), 2.35 (s, 3H), 2.39 (s, 3H), 2.91 (s, 6H), 3.90 (mn, 1H), 4.24 (dd, J=8, 12 Hz, 1H), 4.42 (dd, J=3, 11 Hz, 1H), 7.38(d, J=8 Hz, 2H), 7.44 (d, J=3 Hz, 1H), 7.68 (d, J=8 Hz, 2H), 7.93 (d, J=3 Hz, 1H); Analysis calculated for $C_{11}H_{17}N_2ClO.1.1C_7H_8O_3S.0.2H_2O$: C, 53.26; H, 6.26; N, 6.64; Found: C, 53.17; H, 6.27; N, 6.60; $[α]^{25}D=-4.6°$ (c=0.80, MeOH).

EXAMPLE 37

5-[(R)-2-methylamino-1-propyloxy]-2-chloro-3-methyl pyridine p-toluenesulfonic acid 37 was synthesized according to the following procedure.

First, 5-[(R)-2-N-BOC-methylamino-1-propyloxy]-2-chloro-3-methyl pyridine 37A was prepared as follows.

A solution of the product 35A (183 mg, 0.608 mmol) in THF (8 mL) at room temperature was treated with sodium hydride (60% dispersion in mineral oil, 73 mg, 1.83 mmol) and stirred for 20 minutes. Next, iodomethane (0.31 mL, 4.87 mmol) was added and stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with $CH_2Cl_2$. The combined $CH_2Cl_2$ extract was washed with brine, dried ($MgSO_4$), filtered and concentrated. The residue was flash chromatographed on silica gel with 15% ethyl acetate/hexane to provide a clear oil 37A (79%, 152 mg). MS (CI/NH$_3$) m/e 315 (M+H)$^+$, 332 (M+NH$_4$)$^+$; $^1$H NMR (CDCl$_3$, 300 MHz) δ: 1.25 (d, J=7 Hz, 3H), 1.46 (s, 9H), 2.35 (s, 3H), 2.80 (s, 3H), 3.89–4.03 (m, 2H), 4.51 (bs, 1H), 7.10 (bs, 1H), 7.89 (bs, 1H).

Then 5-[(R)-2-methylamino-1-propyloxy]-2-chloro-3-methyl pyridine p-toluenesulfonic acid 37 was prepared as follows.

A solution of the product 37A (152 mg, 0.483 mmol) in CH$_2$Cl$_2$ (10 mL) was treated with p-toluenesulfonic acid monohydrate (101 mg, 0.532 mmol) and refluxed at 60° C. overnight. Then solvent was removed by bubbling nitrogen into the solution. Ethyl ether (30 mL) was added and stirred for 5 minutes. The ether was decanted and the procedure was repeated. The residue was then dried under vacuum to provide 37 as a hygroscopic white solid. MS (CI/NH$_3$) m/e 215 (M+H)$^+$; $^1$H NMR (D$_2$O, 500 MHz) δ: 1.44 (d, J=7 Hz, 3H), 2.37 (s, 3H), 2.41 (s, 3H), 2.77 (s, 3H), 3.72 (m, 1H), 4.19 (dd, J=7, 11 Hz, 1H), 4.37 (dd, J=3, 10 Hz, 1H), 7.33 (d, J=8 Hz, 2H), 7.45 (d, J=3 Hz, 1H), 7.67 (d, J=8 Hz, 2H), 7.94 (d, J=3 Hz, 1H); Analysis calculated for C$_{10}$H$_{15}$N$_2$ClO.1.6C$_7$H$_8$O$_3$S.0.8H$_2$O: C, 50.46; H, 5.87; N, 5.55; Found: C, 50.74; H, 6.08; N, 5.28; [α]$^{25}$D=−4.9° (c=3.9, MeOH).

EXAMPLE 38

5-[(R)-2-amino-1-propyloxy]-2-chloro-3-(4-vinylpyridinyl)pyridine 10 p-toluenesulfonic acid 38 was synthesized according to the following procedure. First, 5-[(R)-2-N-BOC-amino-1-propyloxy]-2-chloro-3-(4-vinylpyridinyl)pyridine 38A was prepared as follows.

A solution of the product 32A (1.19 g, 3.25 mmol), 4-vinyl pyridine (0.44 mL, 4.07 mmol), palladium (II) acetate (29 mg, 0.130 mmol), tri-o-tolylphosphine (79 mg, 0.260 mmol), and triethylamine (1.62 mL, 11.7 mmol) in acetonitrile (10 mL) was refluxed at 100° C. for 2 days. Then the reaction mixture was diluted with ethyl acetate, washed with saturated sodium carbonate, brine, dried (MgSO$_4$), filtered and concentrated. The residue was flash chromatographed with 30% ethyl acetate/hexane to provide 38A as a white solid (48%, 610 mg); MS (CI/NH$_3$) m/e 390 (M+H)$^+$.

Next, 5-[(R)-2-amino-1-propyloxy]-2-chloro-3-(4-vinylpyridinyl)pyridine 38B was prepared as follows.

A solution of the product 38A (128 mg, 0.329 mmol) in CH$_2$Cl$_2$ (4 mL) was treated with trifluoroacetic acid (2 mL) and stirred at room temperature overnight. Then solvent and the excess reagent were removed under reduced pressure. The residue was dissolved in saturated sodium carbonate solution and extracted 3× with CH$_2$Cl$_2$ The combined CH$_2$Cl$_2$ extract was dried (MgSO$_4$), filtered and concentrated. The residue was flash chromatographed on silica gel with 95/5/0.5 CH$_2$Cl$_2$/CH$_3$OH/NH$_4$OH to provide a light yellow solid 38B (61%, 58 mg). MS (CU/NH$_3$) m/e 290 (M+H)$^+$.

Then 5-[(R)-2-amino-1-propyloxy]-2-chloro-3-(4-vinylpyridinyl)pyridine p-toluenesulfonic acid 38 was prepared as follows.

A solution of the product 38B (58 mg, 0.201 mmol) in ethyl acetate (1 mL) was treated with p-toluenesulfonic acid monohydrate (42 mg, 0.221 mmol) and stirred for 5 minutes. Next ethyl ether (30 mL) was added and stirred for an additional 5 minutes. The ether was decanted and the procedure was repeated. The residue was then dried under vacuum to provide 38 as a light yellow solid. mp 47–49° C.; MS (CI/NH$_3$) m/e 290 (M+H)$^+$; $^1$H NMR (D$_2$O, 500 MHz) δ: 1.48 (d, J=7 Hz, 3H), 2.35 (s, 3H), 3.87 (m, 1H), 4.14 (m, 1H), 4.31 (dd, J=4, 10 Hz, 1H), 7.10 (d, J=6 Hz, 2H), 7.29 (d, J=8 Hz, 2H), 7.45 (d, J=16 Hz, 2H), 7.64 (d, J=8 Hz, 2H), 7.68 (d, J=3 Hz, 1H), 7.93 (d, J=3 Hz, 1H), 8.45 (d, J=6 Hz, 2H); Analysis calculated for C$_{15}$H$_{16}$N$_3$ClO.1.19C$_7$H$_8$O$_3$S.0.95H$_2$O: C, 54.75; H, 5.40; N, 8.21; Found: C, 54.43; H, 5.36; N, 8.61; [α]$^{25}$D=−1.6° (c=0.55, MeOH).

EXAMPLE 39

5-[(R)-2-N-dimethylamino-1-propyloxy]-2-chloro-3-(4-vinylpyridinyl)pyridine p-toluenesulfonic acid 39 was synthesized according to the following procedure.

First 5-[(R)-2-N-dimethylamino-1-propyloxy]-2-chloro-3-(4-vinylpyridinyl)pyridine 39A was prepared as follows.

A solution of the product 38A (300 mg, 0.771 mmol) in a mixture of formaldehyde (37 wt. % in water, 7 mL) and formic acid (4 mL) was stirred at 65° C. overnight. The excess reagents were removed under reduced pressure at 45° C. Aqueous NaOH solution (1N) was then added to the residue and extracted 3× with CH$_2$Cl$_2$. The combined CH$_2$Cl$_2$ extract was washed with brine, dried (MgSO$_4$), filtered, and concentrated. The residue was flash chromatographed on silica gel with 95/5/0.5 CH$_2$Cl$_2$/MeOH/NH$_4$OH to provide 39A as a yellow oil (58%, 143 mg). MS (CI/NH$_3$) m/e 318 (M+H)$^+$.

Then 5-[(R)-2-N-dimethylamino-1-propyloxy]-2-chloro-3-(4-vinylpyridinyl)pyridine p-toluenesulfonic acid 39 was prepared as follows.

A solution of the product 39A (140 mg, 0.442 mmol) in ethyl acetate (1 mL) at room temperature was treated with p-toluenesulfonic acid monohydrate (88 mg, 0.462 mmol) and stirred for 5 minutes. Ethyl ether (30 mL) was added and stirred for an additional 5 minutes. The ether was decanted and the procedure was repeated. It was then dried under vacuum to provide 39 as a light yellow solid. mp 81–83° C.; MS (CI/NH$_3$) m/e 318 (M+H)$^+$; $^1$H NMR (D$_2$O, 500 MHz) δ: 1.47 (d, J=7 Hz, 3H), 2.31 (s, 3H), 2.95 (s, 6H), 3.89 (m, 1H), 4.22 (dd, J=8, 11 Hz, 1H), 4.33 (dd, J=3, 11 Hz, 1H), 6.98 (d, J=16 Hz, 1H), 7.24 (d, J=8 Hz, 2H), 7.27 (s, 1H), 7.42 (d, J=5 Hz, 2H), 7.56 (s, 1H), 7.63 (d, J=8 Hz, 2H), 7.87 (d, J=1 Hz, 1H), 8.34 (d, J=5 Hz, 1H),; Analysis calculated for C$_{17}$H$_{20}$N$_3$ClO.1.45C$_7$H$_8$O$_3$S.0.45H$_2$O: C, 56.65; H, 5.69; N, 7.30; Found: C, 56.36; H, 5.83; N, 7.50; [α]$^{25}$D=−2.80° (c=1.2, MeOH).

EXAMPLE 40

5-[(R)-2-methylamino-1-propyloxy]-2-chloro-3-(4-vinylpyridinyl)pyridine p-toluenesulfonic acid 40 was synthesized according to the following procedure.

First, 5-[(R)-2-N-BOC-methylamino-1-propyloxy]-2-chloro-3-bromo pyridine 40A was prepared as follows.

A solution of the product 34A (440 mg, 1.20 mmol) in THF (15 mL) at room temperature was treated with sodium hydride (60% dispersion in mineral oil, 144 mg, 3.61 mmol) and stirred for 20 minutes. Then iodomethane (0.60 mL, 9.60 mmol) was added and stirred at room temperature overnight. The reaction was quenched by adding saturated ammonium chloride solution (6 mL). Saturated sodium carbonate (10 mL) was also added. THF and the excess iodomethane were removed under reduced pressure. The water phase was extracted 3× with $CH_2Cl_2$. The combined $CH_2Cl_2$ extract was washed with brine, dried ($MgSO_4$), filtered and concentrated. The residue was flash chromatographed on silica gel with 10% ethyl acetate/hexane to provide a light yellow oil 40A (72%, 330 mg). MS ($CI/NH_3$) m/e 455 $(M+H)^+$, 472 $(M+NH_4)^+$.

Then 5-[(R)-2-N-BOC-methylamino-1-propyloxy]-2-chloro-3-(4-vinylpyridinyl)pyridine 40B was made as follows.

A solution of the product 40A (230 mg, 0.606 mmol), 4-vinyl pyridine (0.082 mL, 0.757 mmol), palladium (II) acetate (10 mg, 0.045 mmol), tri-o-tolylphosphine (42 mg, 0.138 mmol), and triethylamine (0.30 mL, 2.18 mmol) in acetonitrile (10 mL) was refluxed at 100° C. for 2 days. The reaction mixture was diluted with ethyl acetate, washed with saturated sodium carbonate, brine, dried ($MgSO_4$), filtered and concentrated. The residue was flash chromatographed with 30% ethyl acetate/hexane to provide 40B (34%, 84 mg); MS ($CI/NH_3$) m/e 404 $(M+H)^+$.

Then 5-[(R)-2-methylamino-1-propyloxy]-2-chloro-3-(4-vinylpyridinyl)pyridine di-p-toluenesulfonic acid 40 was made as follows.

A solution of the product 40B (71 mg, 0.176 mmol) in ethyl acetate (1 mL) was treated with p-toluenesulfonic acid monohydrate (70 mg, 0.368 mmol) and stirred for 5 minutes. Then ethyl ether (30 mL) was added and stirred for an additional 5 minutes. The ether was decanted and the procedure was repeated. The residue was then dried under vacuum to provide 40 as a light yellow solid. mp 66–68° C.; MS ($CI/NH_3$) m/e 304 $(M+H)^+$; $^1H$ NMR ($D_2O$, 400 MHz) δ: 1.49 (d, J=7 Hz, 3H), 2.33 (s, 6H), 2.82 (s, 3H), 3.77 (m, 1H), 4.24 (dd, J=6, 11 Hz, 1H), 4.41 (dd, J=3, 11 Hz, 1H), 7.26 (d, J=7 Hz, 4H), 7.61 (d, J=8 Hz, 4H), 7.68 (s, 1H), 7.73 (d, J=3 Hz, 2H), 7.99 (d, J=7Hz, 2H), 8.04 (d, J=2 Hz, 1H), 8.60 (d, J=8 Hz, 2H); Analysis calculated for $C_{16}H_{18}N_3ClO.2.1C_7H_8O_3S.1.4H_2O$: C, 53.39; H, 5.49; N, 6.08; Found: C, 53.38; H, 5.48; N, 6.01; $[α]^{25}D=-4.5°$ (c=1.1, MeOH).

EXAMPLE 41

5-[(R)-2-ethylamino-1-propyloxy]-2-chloro pyridine p-toluenesulfonic acid 41 was synthesized according to the following procedure.

First, 5-[(R)-2-N-BOC-ethylamino-1-propyloxy]-2-chloro pyridine 41A was made as follows.

A solution of the product 26C (298 mg, 1.04 mmol) in THF (20 mL) at room temperature was treated with sodium hydride (60% dispersion in mineral oil, 125 mg, 3.12 mmol) and stirred for 20 minutes. Iodoethane (0.67 mL, 8.32 mmol) was added and the solution was then stirred at room temperature overnight. The reaction was quenched by adding saturated ammonium chloride solution (6 mL). Saturated sodium carbonate (10 mL) was also added. THF and the excess iodoethane were removed under reduced pressure. The water phase was extracted 3× with $CH_2Cl_2$. The combined $CH_2Cl_2$ extract was washed with brine, dried ($MgSO_4$), filtered and concentrated. The residue was flash chromatographed on silica gel with 10% ethyl acetate/hexane to provide a clear oil 41A (54%, 178 mg). MS ($CI/NH_3$) m/e 315 $(M+H)^+$, 332 $(M+NH_4)^+$; $^1H$ NMR ($CDCl_3$, 300 MHz) δ: 1.12 (t, J=7 Hz, 3H), 1.31 (d, J=7 Hz, 3H), 1.46 (s, 9H), 3.22 (bs, 2H), 3.95 (m, 1H), 4.09 (m, 1H), 4.30 (bs, 1H), 7.18–7.26 (m, 2H), 8.04 (d, J=3 Hz, 1H).

Then 5-[(R)-2-ethylamino-1-propyloxy]-2-chloro pyridine p-toluenesulfonic acid 41 was made as follows.

A solution of the product 41A (177 mg, 0.563 mmol) in $CH_2Cl_2$ (8 mL) was treated with p-toluenesulfonic acid monohydrate (118 mg, 0.621 mmol) and refluxed at 60° C. overnight. Solvent was removed by bubbling nitrogen into the solution. Ethyl ether (30 mL) was added and stirred for 5 minutes. The ether was decanted and the procedure was repeated. It was then dried under vacuum to provide 41 as a white hygroscopic solid. MS ($ESI^+$) m/e 215 $(M+H)^+$; $^1H$ NMR ($D_2O$, 400 MHz) δ: 1.33 (t, J=7 Hz, 3H), 1.45 (d, J=7 Hz, 3H), 2.36 (s, 3H), 3.18 (m, 2H), 3.75 (m, 1H), 4.16 (dd, J=7, 11 Hz, 1H), 4.32 (dd, J=3, 11 Hz, 1H), 7.32 (d, J=8 Hz, 2H), 7.39 (d, J=9 Hz, 1H), 7.45 (dd, J=3, 9 Hz, 1H), 7.66 (d, J=8, 2H), 8.03 (d, J=3 Hz, 1H); Analysis calculated for $C_{10}H_{15}N_2ClO.1.2C_7H_8O_3S.0.3H_2O$: C, 51.79; H. 5.95; N, 6.56; Found: C, 51.86; H, 6.18; N, 6.53; $[α]^{25}D=-5.6°$ (c=1.5, MeOH).

EXAMPLE 42

5-[(R)-2-(1-propyl)amino-1-propyloxy]-2-chloro pyridine p-toluenesulfonic acid 42 was prepared according to the following procedure.

First, 5-[(R)-2-N-BOC-(1-propyl)amino-1-propyloxy]-2-chloro pyridine 42A was made as follows.

A solution of the product 26C (290 mg, 1.01 mmol) in THF (20 mL) at room temperature was treated with sodium hydride (60% dispersion in mineral oil, 122 mg, 3.04 mmol) and stirred for 20 minutes. 1-iodopropane (0.78 mL, 8.09 mmol) was added and stirred at room temperature overnight. The reaction was quenched by adding saturated ammonium chloride solution (6 mL). Saturated sodium carbonate (10 mL) was also added. THF and the excess reagent were removed under reduced pressure. The water phase was extracted 3× with $CH_2Cl_2$. The combined $CH_2Cl_2$ extract was washed with brine, dried ($MgSO_4$), filtered and concentrated. The residue was flash chromatographed on silica gel with 15% ethyl acetate/hexane to provide a clear oil 42A (39%, 130 mg). MS ($CI/NH_3$) m/e 329 $(M+H)^+$.

Then 5-[(R)-2-(1-propyl)amino-1-propyloxy]-2-chloro pyridine p-1(1 toluenesulfonic acid 42 was made as follows. A solution of the product 42A (127 mg, 0.387 mmol) in $CH_2Cl_2$ (10 mL) was treated with p-toluenesulfonic acid monohydrate (89 mg, 0.468 mmol) and refluxed at 60° C. overnight.

Solvent was removed by bubbling nitrogen into the solution. Next, ethyl ether (30 mL) was added and stirred for 5 minutes. The ether was decanted and the procedure was repeated. It was then dried under vacuum to provide 42 as a white hygroscopic solid. MS ($ESI^+$) m/e 229 $(M+H)^+$; $^1H$ NMR (D$_2$O, 400 MHz) δ: 0.95–1.00 (m, 3H), 1.45 (d, J=7 Hz, 3H), 1.67–1.77 (m, 2H), 2.37 (s, 3H), 3.02–3.12 (m, 2H), 3.76 (m, 1H), 4.17 (dd, J=6, 11 Hz, 1H), 4.34 (dd, J=3, 11 Hz, 1H), 7.33 (d, J=8 Hz, 2H), 7.44–7.48 (m, 2H), 7.67 (d, J=9 Hz, 2H), 8.06 (m, 1H); Analysis calculated for C$_{11}$H$_{17}$N$_2$ClO.1.25C$_7$H$_8$O$_3$S.0.4H$_2$O: C, 52.58; H, 6.21; N, 6.21; Found: C, 52.63; H, 6.30; N, 6.03; [α]$^{25}$D=+3.1° (c=0.16, MeOH).

EXAMPLE 43

5-(3-Amino-1-butyloxy)-2-fluoro pyridine p-toluenesulfonic acid 43 was synthesized according to the following procedure. 3-(N-(BOC)amino)butyric acid 43A was made as follows. A solution of 3-aminobutyric acid (2.0 g, 19.4 mnuol) in CH$_2$Cl$_2$ (40 mL) at room temperature was treated with triethylamine (13.4 mL, 97 mmol) and di-tert-butyl dicarbonate (4.44 g, 20.4 mmol), stirred overnight. THF (40 mL) was introduced and refluxed for 2 hours. The reaction mixture was then evaporated to provide the crude product 43A (110%, 4.35 g). MS (CI/MH$_3$) m/e 204 (M+H)$^+$.

Next, 3-(N-BOC)-butanol 43B was made as follows.

A solution of the product from 43A (4.30 g, 21.0 mmol) in anhydrous THF (15 mL) at 0° C. was treated with borane (1M solution in THF, 32 mL) over a period of 45 minutes. The ice bath was then removed and the reaction mixture was stirred at room temperature for 3 hours. Saturated NaHCO$_3$ solution was added slowly to quench the reaction. The resultant solution was then stirred overnight. Solvent was removed under reduced pressure. The remaining water phase was extracted 4× with ethyl ether. The combined ether extract was washed with brine, dried (MgSO$_4$), filtered, and concentrated. The residue was flash chromatographed on silica gel with 95/5 CH$_2$Cl$_2$/CH$_3$OH to provide a yellow oil 43B (25%, 980 mg). MS (CI/NH$_3$) m/e 190 (M+H)$^+$, 207 (M+NH$_4$)$^+$; $^1$H NMR (CDCl$_3$, 300 MHz) δ: 1.19 (d, J=6 Hz, 3H), 1.45 (s, 9H), 1.74–1.87 (m, 2H), 3.34 (bs, 1H), 3.62 (bs, 1H), 3.90 (bs, 1H), 4.41 (bs, 1H).

3-(N-(BOC)amino)butyl 4-methylbenzene sulfonate 43C was next made as follows.

A solution of the product 43B (970 mg, 5.13 mmol) in THF (10 mL) at room temperature was treated with sodium anhydride (246 mg, 6.16 mmol) and p-toluenesulfonyl chloride (1.08 g, 5.65 mmol), stirred overnight. The reaction mixture was diluted with CH$_2$Cl$_2$ to 50 mL, washed with water, 5% NaHCO$_3$, and brine. It was then dried (MgSO$_4$), filtered and concentrated. The residue was flash chromatographed on silica gel with 20% ethyl acetate/hexane to provide a white solid 43C (65%, 1.14 g). MS (CI/NH$_3$) m/e 344 (M+NH$_4$)$^+$; $^1$H NMR (CDCl$_3$, 300 MHz) δ: 1.12 (d, J=7 Hz, 3H), 1.41 (s, 9H), 1.75–1.86 (m, 2H), 2.45 (s, 3H), 3.68 (m, 1H), 4.08 (t, J=7 Hz, 2H), 4.32 (bs, 1H), 7.35 (d, J=8 Hz, 2H), 7.80 (d, J=10 Hz, 2H).

5-((3-(N-(BOC)amino)-1-butyloxy)-2-fluoro pyridine 43D was then made as follows.

A solution of the product 43C (990 mg, 2.89 mmol) in DMF (20 mL) was treated with potassium hydroxide (405 mg, 7.23 mmol) and 2-fluoro-5-hydroxyl pyridine (359 mg, 3.17 mmol), and then stirred at 85° C. overnight. DMF was removed under reduced pressure at 60° C. The residue was dissolved in a mixture of H$_2$O and CH$_2$Cl$_2$. The organic layer was washed with water, and brine. It was then dried (MgSO$_4$), filtered and concentrated. The residue was flash chromatographed on silica gel with 20% ethyl acetate/hexane to provide a light yellow solid 43D (34%, 280 mg). MS (CI/NH$_3$) m/e 285 (M+H)$^+$, 302 (M+NH$_4$)$^+$; $^1$H NMR (CDCl$_3$, 300 MHz) δ: 1.22 (d, J=7 Hz, 3H), 1.42 (s, 9H), 1.86–2.00 (m, 2H), 3.91 (m, 1H), 4.02–4.09 (m, 2H), 4.57 (bs, 1H), 6.85 (dd, J=3, 9 Hz, 1H), 7.32 (m, 1H), 7.82 (dd, J=2, 3 Hz, 1H).

Then 5-(3-N-BOC-amino-1-butyloxy]-2-fluoro pyridine 43E was made as follows.

A solution of the product from Example 43D (270 mg, 0.951 mmol) in CH$_2$Cl$_2$ (5 mL) was treated with trifluoroacetic acid (2 mL) and stirred at room temperature overnight. Solvent and excess reagent were removed under reduced pressure. The residue was dissolved in saturated sodium carbonate solution and extracted 3× with CH$_2$Cl$_2$ The combined CH$_2$Cl$_2$ extract was dried (MgSO$_4$), filtered and concentrated to provide a light yellow oil 43E (58%, 102 mg). MS (CI/NH$_3$) m/e 185 (M+H)$^+$.

Then 5-(3-amino-1-butyloxy)-2-fluoro pyridine p-toluenesulfonic acid 43 was made as follows.

A solution of the product 43E (34 mg, 0.185 mmol) in ethyl acetate (1 mL) was treated with p-toluenesulfonic acid monohydrate (37 mg, 0.195 mmol) and stirred for 5 minutes. Next ethyl ether (30 ml) was added and stirred for an additional 5 minutes. The ether was decanted and the procedure was repeated. The residue was then dried under vacuum to provide 43 as a white solid. mp 142–144° C.; MS (CI/NH$_3$) m/e 185 (M+H)$^+$; $^1$H NMR(D$_2$O, 300 MHz) δ: 1.39 (d, J=7 Hz, 3H), 2.08–2.25 (m, 2H), 2.41 (s, 3H), 3.68 (dd, J=7, 13 Hz, 1H), 4.20–4.30 (m, 2H), 4.14 (dd, J=4, 11 Hz, 1H), 7.08 (dd, J=3, 9 Hz, 1H), 7.38 (d, J=8 Hz, 2H), 7.61 (m, 1H), 7.70 (d, J=8 Hz, 2H), 7.87 (dd, J=1, 3 Hz, 1H). Analysis calculated for C$_9$H$_{13}$N$_2$FO.C$_7$H$_8$O$_3$S: C, 53.92; H, 5.94; N, 7.86; Found: C, 53.81; H, 5.89; N, 7.72.

EXAMPLE 44

5-(3-Amino-1-butyloxy)-2-chloropyridine p-toluenesulfonate 44 was synthesized according to the following procedure.

First, 5-(3-N-(BOC)-1-butyloxy)-2-chloropyridine 44A was synthesized as follows. A solution of the product 43C (320 mg, 0.93 mmol) in DMF (3 mL) was treated with potassium hydroxide (92 mg, 1.83 mmol) and 2-chloro-5-hydroxyl pyridine (130 mg, 1.03 mmol), and then stirred at 60° C. for 48 hours. DMF was removed under reduced pressure at 60° C. The residue was dissolved in a mixture of H$_2$O and CH$_2$Cl$_2$. The organic layer was washed with water, and brine; then dried (MgSO$_4$), filtered and concentrated. The residue was flash chromatographed on silica gel with 50% ethyl acetate/hexane to provide a light yellow solid 44A (43%, 120 mg). MS (CI/NH$_3$) m/e 301 (M+H)$^+$, 303 (M+NH$_4$)$^+$; $^1$H NMR (CDCl$_3$, 300 MHz) δ: 1.22 (d, J=7 Hz, 3H), 1.42 (s, 9H), 1.86–2.02 (m, 2H), 3.92 (m, 1H), 4.02–4.12 (m, 2H), 4.45 (bs, 1H), 7.19 (d, J=5.6 Hz, 1H), 7.22 (d, J=3 Hz, 1H), 8.04 (d, J=3 Hz, 1H).

5-(Amino-1-butyloxy]-2-fluoro pyridine p-toluenesulfonic acid 44 was prepared next as follows.

A solution of the product 44A (69 mg, 0.26 mmol) in CH$_2$Cl$_2$ (2 mL) was treated with p-toluenesulfonic acid (31 mg, 0.28 mmol) and stirred at reflux for 4 hours. Next, solvent was removed under reduced pressure. Ethyl ether (30 ml) was added and stirred for an additional 5 minutes. The ether was decanted and the procedure was repeated. The residue was then dried under vacuum to provide 44 as a white solid. mp 190–191° C.; MS (CI/NH$_3$) m/e 201 (M+H)$^+$; 218 (M+NH4)$^+$. $^1$H NMR (D$_2$O, 300 MHz) δ: 1.38 (d, J=7 Hz, 3H), 2.05–2.25 (m, 2H), 2.40 (s, 3H), 3.68 (dd, J=7, 13 Hz, 1H), 4.22–4.32 (m, 2H), 7.37 (d, J=8.5 Hz, 2H), 7.4–7.6 (m, 2H), 7.69 (d, J=8 Hz, 2H), 8.06 (d, J=3 Hz, 1H). Analysis calculated for C$_9$H$_{13}$N$_2$ClO.1.1C$_7$H$_8$O$_3$S: C, 51.42; H, 5.81; N, 7.11; Found: C, 51.06; H, 5.81; N, 7.11.

EXAMPLE 45

5-(3-Dimethylamino-1-butyloxy]-2-chloro pyridine p-toluenesulfonic acid 45 was synthesized according to the following procedure.

First, 5-(3-dimethylamino-1-butyloxy]-2-chloro pyridine 45A was made as follows.

A solution of the product 44A (120 mg, 0.44 mmol) in formic acid (2.5 mL) was treated with 37% formalin solution (5 mL) and the resultant mixture was heated at 60° C. for 5 hours. Solvent and excess reagent were removed under reduced pressure. The residue was dissolved in saturated sodium carbonate solution and extracted 3x with CH$_2$Cl$_2$ The combined CH$_2$Cl$_2$ extract was dried (MgSO$_4$), filtered and concentrated to provide a light yellow oil 45A (58%, 102 mg). MS (CI/NH$_3$) m/e 229 (N+H)$^+$, m/e 231 (M+NH$_4$)$^+$; $^1$H NMR (CDCl$_3$, 300 MHz) δ: 1.05 (d, J=6 Hz, 3H), 1.45–1.85 (m, 4H), 2.03 (m, 1H), 2.29 (s, 6H), 4.00–4.15 (m, 2H), 7.17–7.24 (m, 2H), 8.05 (d, J=1 Hz, 1H).

Next, 5-(3-dimethylamino-1-butyloxy]-2-chloro pyridine p-toluenesulfonic acid 45 was made as follows.

A solution of the product 45A (67 mg, 0.29 nmnol) in ethyl acetate (1 mL) was treated with p-toluenesulfonic acid monohydrate (32 mg, 0.30 mmol) and stirred for 5 minutes. Next, ethyl ether (30 ml) was added and stirred for an additional 5 minutes. The ether was decanted and the procedure was repeated. The residue was then dried under vacuum to provide 45 as a white solid. mp 100–102° C.; MS (CI/NH$_3$) m/e 229(M+H)$^+$. $^1$H NMR (D$_2$O, 300 MHz) δ: 1.39 (d, J=7 Hz, 3H), 2.08 (m, 1H), 2.34 (m, 1H), 2.41 (s, 3H), 2.8 (s, 6H), 3.70 (m, 1H), 4.15–4.32 (m, 2H), 7.38 (d, J=8 Hz, 2H), 7.42–7.51 (m, 2H), 7.69 (d, J=8 Hz, 2H), 8.06 (d, J=3 Hz, 1H). Analysis calculated for C$_{11}$H$_{17}$N$_2$ClO.1C$_7$H$_8$O$_3$S: C, 53.93; H, 6.24; N, 6.99; Found: C, 53.67; H, 6.24; N, 7.02.

EXAMPLE 46

5-(3-Dimethylamino-1-butyloxy)-2-chloro-3-bromopyridine p-toluenesulfonic acid 46 was synthesized according to the following procedure.

First, 5-(3-N-BOC-amino-1-butyloxy)-2-chloro-3-bromo pyridine 46A was made as follows. A solution of the product 43C (1.0 g, 2.9 mmol) in THF (4 mL) was treated with potassium hydroxide (290 mg, 5.8 mmol) and 2-chloro-3-bromo-5-hydroxyl pyridine (667 mg, 3.19 mmol), stirred at 70° C. for 16 hours. THF was removed under reduced pressure at 25° C. The residue was dissolved in a mixture of H$_2$O and CH$_2$Cl$_2$. The organic layer was washed with water, and brine; then dried (MgSO$_4$), filtered and concentrated. The residue was flash chromatographed on silica gel with 33% ethyl acetate/hexane to provide a light yellow solid 46A (37%, 412 mg). MS (CI/NH$_3$) m/e 381 (M+H)$^+$, 398 (M+NH$_4$)$^+$; $^1$H NMR (CDCl$_3$, 300 MHz) δ: 1.22 (d, J=7 Hz, 3H), 1.42 (s, 9H), 1.86–2.02 (m, 2H), 3.92 (m, 1H), 4.02–4.12 (m, 2H), 4.45 (bs, 1H), 7.22 (d, J=2 Hz, 1H), 8.03 (s, 1H).

Then 5-(dimethylamino-1-butyloxy]-2-chloro-3-bromo pyridine p-toluenesulfonic acid 46B was made as follows.

A solution of the product from Example 46A (84 mg, 0.22 mmol) in formic acid (2.5 mL) was treated with 37% formalin solution (5 mL) and the resultant mixture was heated at 60° C. for 5 hours. Solvent and excess reagent were removed under reduced pressure. The residue was dissolved in saturated sodium carbonate solution and extracted 3x with CH$_2$Cl$_2$ The combined CH$_2$Cl$_2$ extract was dried (MgSO$_4$), filtered and concentrated to provide a light yellow oil as the title compound. The residue was then purified on the column. Elution with ethyl acetate/methanol/ammonium hydroxide (10:1:0.1) gave the desired product 46B.(62%, 42 mg). MS (CI/NH$_3$) m/e 309 (M+H)$^+$, m/e 311 (M+NH$_4$)$^+$; $^1$H NMR (CDCl$_3$, 300 MHz) δ: 1.03 (d, J=6 Hz, 3H), 1.75 (m, 1H), 2.03 (m, 1H), 2.85 (bs, 1H), 2.28 (s, 6H), 4.00–4.16 (m, 2H), 7.53 (d, J=3 Hz, 1H), 8.04 (d, J=3 Hz, 1H).

5-(3-Dimethylamino-1-butyloxy]-2-chloro-3-bromopyridine p-toluenesulfonic acid 46 was then prepared as follows.

A solution of the product from Example 46B (42 mg, 0.14 mmol) in ethyl acetate (1 mL) was treated with p-toluenesulfonic acid monohydrate (26 mg, 0.15 mmol) and stirred for 5 minutes. Next, ethyl ether (30 ml) was added and stirred for an additional 5 minutes. The ether was decanted and the procedure was repeated. The residue was then dried under vacuum to provide 46 as a white solid. mp 95–97° C.; MS (CI/NH$_3$) m/e 307 (M+H)$^+$. $^1$H NMR (D$_2$O, 300 MHz) δ: 1.39 (d, J=7 Hz, 3H), 2.08 (m, 1H), 2.34 (m, 1H), 2.41 (s, 3H), 2.87 (s, 3H), 3.70 (m, 1H), 4.15–4.32 (m, 2H), 7.37 (d, J=8 Hz, 2H), 7.69 (d, J=8 Hz, 2H),7.84 (d, J=3 Hz, 1H), 8.07 (d, J=3 Hz, 1H). Analysis calculated for C$_{11}$H$_{16}$N$_2$BrClO.C$_7$H$_8$O$_3$S: C, 45.02; H, 5.00; N, 5.84; Found: C, 44.88; H, 5.15; N, 5.61.

EXAMPLE 47

5-(3-Amino-1-butyloxy)-2-chloro-3-bromo-pyridine p-toluenesulfonic acid 47 was synthesized according to the following procedure.

First, a solution of the product 46A (90 mg, 0.24 mmol) in CH$_2$Cl$_2$ (2 mL) was treated with trifluoroacetic acid (2 mL) and stirred at room temperature overnight. Solvent and excess reagent were removed under reduced pressure. The residue was dissolved in saturated sodium carbonate solution and extracted 3x with CH$_2$Cl$_2$ The combined CH$_2$Cl$_2$ extract was dried (MgSO$_4$), filtered and concentrated to provide a light yellow oil 5-(3-amino-1-butyloxy)-2-chloro-3-bromopyridine 47A. The residue was then purified on the column. Elution with ethyl acetate/methanol/ammonium hydroxide (10:1:0.1) gave the desired product.(58%, 39 mg).

MS (CI/NH$_3$) m/e 279 (M+H)$^+$; $^1$H NMR (CDCl$_3$, 300 MHz) δ: 1.19 (d, J=6 Hz, 3H), 1.60–2.00 (m, 3H), 3.20 (m, 1H), 4.05–4.20 (m, 2H), 7.53 (d, J=3 Hz, 1H), 8.04 (d, J=3 Hz, 1H).

Next, 5-(3-amino-1-butyloxy)-2-chloro-3-bromo-pyridine p-toluenesulfonic acid 47 was made as follows.

A solution of the product 47A (39 mg, 0.185 mmol) in ethyl acetate (1 mL) was treated with p-toluenesulfonic acid monohydrate (37 mg, 0.14 mmol) and stirred for 5 minutes. Ethyl ether (30 ml) was added and stirred for an additional 5 minutes. The ether was decanted and the procedure was repeated. The residue was then dried under vacuum to provide 47 as a white solid. mp 140–142° C.; MS (CI/NH$_3$) m/e 279 (M+H)$^+$; 311 (M+NH$_4$)$^+$ $^1$H NMR (D$_2$O, 300 MHz) δ: 1.38 (d, J=7 Hz, 3H), 2.08–2.25 (m, 2H), 2.41 (s, 3H), 3.65 (dd, J=7, 13 Hz, 1H), 4.20–4.32 (m, 2H), 7.38 (d, J=8 Hz, 2H), 7.69 (d, J=8 Hz, 2H), 7.87 (d, J=3 Hz, 1H), 8.09 (d, J=0.0 Hz, 1H). Analysis calculated for C$_9$H$_{12}$N$_2$BrClO.C$_7$H$_8$O$_3$S: C, 42.50; H, 4.43; N, 6.20; Found: C, 42.58; H, 4.60; N, 5.94.

EXAMPLE 48

5-(3-dimethylamino-1-butyloxy]-2-chloro-methylpyridine p-toluenesulfonic acid 48 was synthesized according to the following procedure.

First, 5-(3-(N-(BOC)amino-1-butyloxy)-2-choro-3-methylpyridine 48A was synthesized as follows. A solution of the product 43C (0.85 g, 2.48 mmol) in THF (6 mL) was treated with potassium hydroxide (373 mg, 7.4 mmol) and 2-chloro-3-methyl-5-hydroxyl pyridine (395 mg, 2.73 mmol), and then stirred at 80° C. for 16 hours. THF was removed under reduced pressure at 25° C. The residue was dissolved in a mixture of H$_2$O and CH$_2$Cl$_2$. The organic layer was washed with water, and brine; then dried (MgSO$_4$), filtered and concentrated. The residue was flash chromatographed on silica gel with 33% ethyl acetate/hexane to provide a light yellow solid 48A (39%, 270 mg). MS (CI/NH$_3$) m/e 315 (M+H)$^+$, 317 (M+NH$_4$)$^+$; $^1$H NMR (CDCl$_3$, 300 MHz) δ: 1.21 (d, J=7 Hz, 3H), 1.42 (s, 9H), 1.86–2.02 (m, 2H), 2.34 (s, 3H),3.92 (m, 1H), 4.02–4.12 (m, 2H), 4.45 (bs, 1H), 7.12 (bs, 1H), 7.89 (s, 1H).

Next, 5-(3-dimethylamino-1-butyloxy)-2-chloro-3-methyl pyridine 48B was made as follows.

A solution of the product 48A (57 mg, 0.18 mmol) in formic acid (1 mL) was treated with 37% formalin solution (2.5 mL) and the resultant mixture was heated at 70° C. for 5 hours. Solvent and excess reagent were removed under reduced pressure. The residue was dissolved in saturated sodium carbonate solution and extracted 3× with CH$_2$Cl$_2$ The combined CH$_2$Cl$_2$ extract was dried (MgSO$_4$), filtered and concentrated to provide a light yellow oil as the title compound. The residue was then purified on the column. Elution with ethyl acetate/methanol/ammonium hydroxide (10:1:0.1) gave 48B. (100%, 63 mg). MS (CI/NH$_3$) m/e 243 (M+H)$^+$; $^1$H NMR (CDCl$_3$, 300 MHz) δ: 1.09 (d, J=6 Hz, 3H), 1.78 (m, 1H), 2.03 (m, 1H), 2.35 (s, 6H), 2.93 (bs, 1H), 4.00–4.15 (m, 2H), 7.12 (d, J=3 Hz, 1H), 7.90 (d, J=3 Hz, 1H).

Then, 5-(3-dimethylamino-1-butyloxy)-2-chloro-methylpyridine p-toluenesulfonic acid 48 was made as follows.

A solution of the product 45A (63 mg, 0.26 mmol) in ethyl acetate (1 mL) was treated with p-toluenesulfonic acid monohydrate (49 mg, 0.27 mmol) and stirred for 5 minutes. Then ethyl ether (30 ml) was added and stirred for an additional 5 minutes. The ether was decanted and the procedure was repeated. The residue was then dried under vacuum to provide 48 as a white solid. MS (CI/NH$_3$) m/e 243(M+H)$^+$. $^1$H NMR (D$_2$O, 300 MHz) δ: 1.39 (d, J=7 Hz, 3H), 2.09 (m, 1H), 2.33 (m, 1H), 2.37 (s, 3H), 2.38 (s, 3H), 2.87 (s, 6H), 3.70 (m, 1H), 4.15–4.27 (m, 2H), 7.35 (d, J=8 Hz, 2H), 7.37 (d, J=4 Hz, 1H) 7.68 (d, J=8 Hz, 2H), 7.87 (d, J=3 Hz, 1H). Analysis calculated for C$_{12}$H$_{19}$N$_2$ClO.1.3C$_7$H$_8$O$_3$S.H$_2$O: C, 52.30; H, 6.53; N, 5.78; Found: C, 52.00; H, 6.33; N, 6.10

EXAMPLE 49

5-(3-Amino-1-butyloxy)-2-chloro-3-methyl-pyridine p-toluenesulfonic acid 49 was synthesized according to the following procedure.

A solution of the product 48A (99 mg, 0.36 mmol) in methylene chloride (5 mL) was treated with p-toluenesulfonic acid monohydrate (74 mg, 0.39 mmol) and stirred at reflux for 5 hours. After ethanol was reduced to a smaller volume, ethyl ether (30 ml) was added and stirred for an additional 5 minutes. The ether was decanted and the procedure was repeated. The residue was then dried under vacuum to provide 49 as a white solid. mp 163–165° C.; MS (CI/NH$_3$) m/e 215(M+H)$^+$., 232(M+NH$_4$)$^+$ $^1$H NMR (D$_2$O, 300 MHz) δ: 1.37 (d, J=7 Hz, 3H), 2.02–2.22 (m, 2H), 2.33 (s, 3H), 2.38 (s, 3H), 3.64 (m, 1H), 4.15–4.30 (m, 2H), 7.35 (d, J=8 Hz, 2H), 7.40 (d, J=3 Hz, 1H), 7.68(d, J=8 Hz, 1H), 7.87 (d, J=3 Hz, 1H). Analysis calculated for C$_{10}$H$_{15}$N$_2$ClO.1.3C$_7$H$_8$O$_3$S.0.5H$_2$O: C, 51.26; H, 5.95; N, 6.26; Found: C, 51.35; H, 5.85; N, 6.28.

EXAMPLE 50 in vitro

Compounds of the invention were subjected to in vitro assays against the nicotinic acetylcholine receptor as described below and were found to be effective binders to the receptor. The in vitro protocols for determination of nicotinic acetylcholine channel receptor binding potencies of ligands was determined as follows.

Binding of [$^3$H]-cytisine ([$^3$H]-CYT) to neuronal nicotinic acetylcholine receptors was accomplished using crude synaptic membrane preparations from whole rat brain (Pabreza et al., *Molecular Pharmacol.*, 1990, 39:9). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000×g for 15 minutes, the pellets were resuspended in 30 volumes of buffer.

The test compounds were dissolved in water to make 10 mM stock solutions. Each solution was then diluted (1:100) with buffer (as above) and further taken through seven serial log dilutions to produce test solutions from 10$^{-5}$, to 10$^{-11}$ M.

Homogenate (containing 125–150 μg protein) was added to triplicate tubes containing the range of concentrations of test compound described above and [$^3$H]-CYT (1.25 nM) in a final volume of 500 µL. Samples were incubated for 60 minutes at 4° C., then rapidly filtered through Whatman GF/B filters presoaked in 0.5% polyethyleneimine using 3×4 mL of ice-cold buffer. The filters are counted in 4 mL of Ecolume® (ICN). Nonspecific binding was determined in the presence of 10 µM (−)-nicotine and values were expressed as a percentage of total binding. $IC_{50}$ values were determined with a four-parameter non-linear regression and $IC_{50}$ values were converted to $K_1$ values using the Cheng and Prusoff correction ($K_1=IC_{50}/(1+[ligand]/K_d$ of ligand).

The results are detailed in Tables 1 and 2. Each Example number corresponds to the synthetic Examples described above. Examples 1–49 in these tables are the compounds of the present invention. The lower the $K_1$ value, the more affinity for neuronal nicotinic acetylcholine receptors.

in vivo

An in vivo protocol was utilized to determine the effectiveness of nicotinic acetylcholine receptor ligands as analgesic agents in the mouse hot plate paradigm.

Separate groups of mice, (n=8/group) were utilized for each dose group. All drugs were administered by the intraperitoneal route of administration. Test drugs were dissolved in water to make a 6.2 mM stock solution. Animals were dosed with this solution (10 mL/kg body weight) for a 62 micromol/kg dose. Lower doses were administered similarly, following serial dilution of the stock solution in half-log increments. Animals were dosed 30 minutes prior to testing in the hot plate. The hot-plate utilized was an automated analgesia monitor (Model #AHP16AN, Omnitech Electronics, Inc. of Columbus, Ohio). The temperature of the hot plate was maintained at 55° C. and a cut-off time of 180 seconds was utilized. A control was run against each compound tested. Latency until the tenth jump was recorded as the dependent measure. An increase in the tenth jump latency relative to the control was considered a significant effect.

Tables 1 and 2 below illustrates the results obtained by following the above procedures.

Table 1 also shows the minimally effective dose (MED), among the doses tested, at which a significant effect, as defined above, was observed for the present compounds in the column labelled dosage. The lower the dosage at which the significant effect is observed, the more effective the compound. The data shows that selected compounds of the invention show a significant antinociceptive effect at doses ranging from 6.2 to 62 µmol/kg.

TABLE 1

| Example | * (Stereochem) | $R^1$, $R^2$, $R^3$ | $X^1$, $X^2$ | $K_1$ (nM) | Analgesic MED (µmol/kg) |
|---|---|---|---|---|---|
| 1 | S | H, H, Me | 2-Cl | 4.51 | 62 |
| 2 | S | Me, Me, Me | 2-Cl | 42.0 | 62 |
| 3 | S | H, Me, Me | 2-Cl | 40.6 | 62 |
| 4 | S | H, H, Me | 2-F | 8.69 | 6.2 |
| 5 | S | Me, Me, Me | 2-F | 100 | * |
| 6 | S | H, Me, Me | 2-F | 68.9 | * |
| 7 | S | H, H, Me | 2-Cl, 3-Br | 1.55 | * |
| 8 | S | Me, Me, Me | 2-Cl, 3-Br | 30.8 | 62 |
| 9 | S | H, Me, Me | 2-Cl, 3-Br | 10.9 | ** |
| 10 | S | H, H, Me | 2-Cl, 3-Me | 0.525 | 62 |
| 11 | S | Me, Me, Me | 2-Cl, 3-Me | 9.60 | * |
| 12 | S | H, Me, Me | 2-Cl, 3-Me | 5.47 | 62 |
| 13 | S | H, H, Me | 2-Cl, 3-(4-vinylpyridinyl) | 0.0761 | * |
| 14 | S | Me, Me, Me | 2-Cl, 3-(4-vinylpyridinyl) | 0.367 | * |
| 15 | S | H, H, Et | 2-Cl | 14.7 | * |
| 16 | S | H, H, Et | 2-F | 39.5 | N/T |
| 17 | S | H, Me, Et | 2-F | 225 | N/T |
| 18 | S | H, H, Et | 2-Cl, 3-Br | 14.8 | * |
| 19 | S | H, H, Et | 2-Cl, 3-(4-vinylpyridinyl) | 0.180 | N/T |
| 20 | S | Me, Me, Et | 2-Cl, 3-(4-vinylpyridinyl) | 3.61 | N/T |
| 21 | S | H, H, benzyl | 2-Cl, 3-Br | 102 | N/T |
| 22 | S | Me, Me, benzyl | 2-Cl, 3-Br | 319 | N/T |
| 23 | S | H, H, benzyl | 2-Cl, 3-(4- | 9.89 | * |

TABLE 1-continued

![Structure with R1R2N-C*(R3)-CH2-O-pyridine(X1,X2)]

| Example | *(Stereochem) | $R^1, R^2, R^3$ | $X^1, X^2$ | $K_1$ (nM) | Analgesic MED ($\mu$mol/kg) |
|---|---|---|---|---|---|
| 24 | S | Me, Me, benzyl | 2-Cl, 3-(4-vinylpyridinyl) | 4.63 | * |
| 25 | S | H, Me, benzyl | 2-Cl, 3-(4-vinylpyridinyl) | 2.61 | N/T |
| 26 | R | H, H, Me | 2-Cl | 5.34 | 62 |
| 27 | R | Me, Me, Me | 2-Cl | 42.1 | * |
| 28 | R | H, Me, Me | 2-Cl | 5.87 | 62 |
| 29 | R | H, H, Me | 2-F | 6.60 | 62 |
| 30 | R | Me, Me, Me | 2-F | 70.2 | * |
| 31 | R | H, Me, Me | 2-F | 11.4 | 62 |
| 32 | R | H, H, Me | 2-Cl, 3-Br | 1.54 | 62 |
| 33 | R | Me, Me, Me | 2-Cl, 3-Br | 11.9 | N/T |
| 34 | R | H, Me, Me | 2-Cl, 3-Br | 1.48 | * |
| 35 | R | H, H, Me | 2-Cl, 3-Me | 0.985 | 62 |
| 36 | R | Me, Me, Me | 2-Cl, 3-Me | 7.20 | * |
| 37 | R | H, Me, Me | 2-Cl, 3-Me | 0.565 | * |
| 38 | R | H, H, Me | 2-Cl, 3-(4-vinylpyridinyl) | 0.0809 | N/T |
| 39 | R | Me, Me, Me | 2-Cl, 3-(4-vinylpyridinyl) | 0.103 | * |
| 40 | R | H, Me, Me | 2-Cl, 3-(4-vinylpyridinyl) | 0.0757 | N/T |
| 41 | R | H, Et, Me | 2-Cl | 2313 | N/T |
| 42 | R | H, Pr, Me | 2-Cl | 7529 | N/T |

*no effect at 62;
**no effect at 6.2
N/T = not tested

TABLE 2

![Structure with R1R2N-CH(Me)-CH2CH2-O-pyridine(X1,X2)]

| Example | $R_1, R_2$ | $X_1, X_2$ | $K_1$ (nm) | Analgesia MED ($\mu$mol/kg) |
|---|---|---|---|---|
| 43 | H, H | 2-Fl | 122 | N/T |
| 44 | H, H | 2-Cl | 20 | N/T |
| 45 | Me, Me | 2-Cl | 18 | N/T |
| 46 | Me, Me | 2-Cl, 3-Br | 3.1 | N/T |
| 47 | H, H | 2-Cl, 3-Br | 31 | N/T |
| 48 | Me, Me | 2-Cl, 3-Me | 1.3 | N/T |
| 49 | H, H | 2-Cl, 3-Me | 25 | N/T |

All references cited are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

1. A compound of the structure

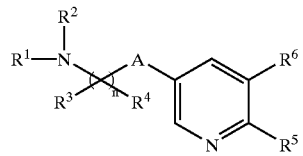

wherein n is an integer of 1 to 4;

$R^1$ and $R^2$ are independently selected from the group consisting of hydrogen, lower alkyl, alkenyl, alkynyl, aralkyl and cyanomethyl;

$R^3$, at each occurrence, is selected from the group consisting of hydrogen, haloalkyl and lower alkyl;

$R^4$, at each occurrence, is independently selected from the group consisting of hydrogen, lower alkyl, lower alkenyl, lower alkynyl, and aralkyl;

$R^5$ is selected from the group consisting of hydrogen, halogen, lower alkyl, nitro, lower alkylamino and lower alkoxy;

$R^6$ is selected from the group consisting of hydrogen, halogen, hydroxyl, lower alkyl, lower alkenyl, lower alkynyl, lower alkoxy, alkenoxy, —$CF_3$, carboxaldahyde, —CH=NOH, aryl, heterocyclyl, wherein the heterocyclyl is unsubstituted pyridinyl or pyridinyl substituted with alkenyl, and aralkenyl; and A is selected from the group consisting of —O—, —S—, —N($R^1$)—, —$SO_2$N($R^1$)— and —$NR^1SO_2$—; and pharmaceutically acceptable salts thereof; with the proviso that when A=O at least one of $R^5$ or $R^6$ is halogen; and with the further proviso that when $R^3$ and $R^4$ are attached to a carbon which is alpha to a heteroatom, $R^4$ is not halogen, hydroxyl or amino.

2. A compound of claim 1 of the structure

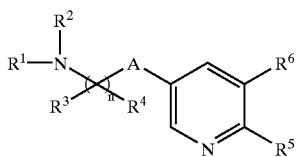

wherein n is an integer of 1 to 4;

$R^1$ and $R^2$ are independently selected from the group consisting of hydrogen, lower alkyl, alkenyl, alkynyl, aralkyl and cyanomethyl;

$R^3$, at each occurrence, is selected from the group consisting of hydrogen, haloalkyl and lower alkyl;

$R^4$, at each occurrence, is independently selected from the group consisting of hydrogen, lower alkyl, lower alkenyl, lower alkynyl, and aralkyl;

$R^5$ is selected from the group consisting of hydrogen, halogen, lower alkyl, nitro, lower alkylamino and lower alkoxy; and $R^6$ is selected from the group consisting of hydrogen, halogen, hydroxyl, lower alkyl, lower alkenyl, lower alkynyl, lower alkoxy, alkenoxy, —$CF_3$, carboxaldahyde, —CH=NOH, -aryl, heterocyclyl, wherein the heterocyclyl is unsubstituted pyridinyl or pyridinyl substitutes with alkenyl, and aralkenyl; and pharmaceutically acceptable salts thereof; with the proviso that when $R^3$ and $R^4$ are attached to a carbon which is alpha to a heteroatom, $R^4$ is not halogen, hydroxyl or amino, and with further proviso that at least one of $R^5$ or $R^6$ is halogen.

3. A compound of claim 2 wherein n=2, $R^5$ is halogen and $R^6$ is selected from the group consisting of hydrogen, lower alkyl and halogen.

4. A compound of claim 1 of the structure

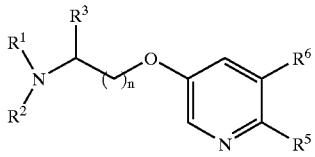

wherein n is an integer of 1 to 4;

$R^1$ and $R^2$ are independently selected from the group consisting of hydrogen and lower alkyl;

$R^3$ is selected from the group consisting of hydrogen, haloalkyl and lower alkyl;

$R^5$ is selected from the group consisting of hydrogen, halogen, lower alkyl, nitro, lower alkylamino and lower alkoxy; and $R^6$ is selected from the group consisting of hydrogen, halogen, hydroxyl, lower alkyl, lower alkenyl, lower alkynyl, lower alkoxy, alkenoxy, —$CF_3$, carboxaldahyde, aryl, heterocyclyl, wherein the heterocyclyl is unsubstituted pyridinyl or pyridinyl substituted with alkenyl and aralkenyl; and pharmaceutically acceptable salts thereof; with the proviso that at least one of $R^5$ or $R^6$ is halogen.

5. The compound of claim 4 wherein $R^5$ and $R^6$ are each independently selected from the group consisting of lower alkyl, —F, —Cl and —Br; n is 1 and $R^3$ is selected from the group consisting of haloalkyl and lower alkyl.

6. The compound of claim 4 wherein $R^5$ and $R^6$ are each independently selected from the group consisting of lower alkyl, —F, —Cl and —Br; n is 2 and $R^3$ is selected from the group consisting of haloalkyl and lower alkyl.

7. The compound according to claim 2 selected from the group consisting of 5-[(S)-2-amino-1-propyloxy]-2-chloro pyridine, 5-[(S)-2-methylamino-1-propyloxy]-2-chloro pyridine, 5-[(S)-2-amino-1-propyloxy]-2-fluoro pyridine, 5-[(S)-2-methylamino-1-propyloxy]-2-fluoro pyridine, 5-[(S)-2-methylamino-1-propyloxy]-2-chloro-3-bromo pyridine, 5-[(S)-2-methylamino-1-propyloxy]-2-chloro-3-methyl pyridine and pharmaceutically acceptable salts thereof.

8. A method for controlling pain, Alzheiner's disease, Parkinson's disease, memory dysfunction, Tourette's syndrome, sleep disorders, attention deficit, hyperactivity disorder, neurodegeneration, inflammation, neuroprotection, amyotrophic atral sclerosis, anziety, depression, mania, schizophrenia, anorexia and other eating disorders, AIDS-induced dementia, epilepsy, urinary incontinence, Crohn's disease, migraine, PMS, erectile dysfunction, substance abuse, smoking cessation and, inflammatory bowel syndrome, in a mammal comprising administering to said mammal a therapeutically effective amount of a compound of claim 1.

9. A pharmaceutical composition comprising;

a compound of claim 1 and pharmaceutically acceptable salts thereof; in a pharmaceutically acceptable carrier.

10. A method for controlling pain in a mammal comprising administering to said mammal a therapeutically effective amount of a compound of claim 1.

* * * * *

UNITED STATES PATENT AND TRADEMARK OFFICE
CERTIFICATE OF CORRECTION

PATENT NO.    : 6,656,958 B2  
DATED         : December 2, 2003  
INVENTOR(S)   : Nan-Horng Lin et al.

Page 1 of 1

It is certified that error appears in the above-identified patent and that said Letters Patent is hereby corrected as shown below:

<u>Column 61,</u>  
Line 21, replace " 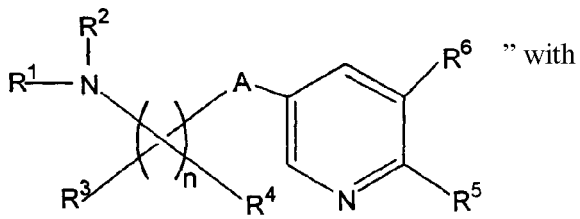 " with

-- 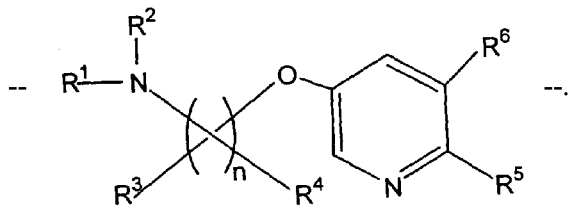 --.

Signed and Sealed this

Eleventh Day of April, 2006

JON W. DUDAS  
*Director of the United States Patent and Trademark Office*